United States Patent
Nielsen et al.

(10) Patent No.: US 11,091,753 B2
(45) Date of Patent: Aug. 17, 2021

(54) XYLOSE FERMENTING YEAST STRAINS AND PROCESSES THEREOF FOR ETHANOL PRODUCTION

(71) Applicant: Novozymes A/S, Bagsvaerd (DK)

(72) Inventors: Michael Lynge Nielsen, Bagsvaerd (DK); Nicholas Jochumsen, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/617,430

(22) PCT Filed: May 31, 2018

(86) PCT No.: PCT/EP2018/064347
§ 371 (c)(1),
(2) Date: Nov. 26, 2019

(87) PCT Pub. No.: WO2018/220116
PCT Pub. Date: Dec. 6, 2018

(65) Prior Publication Data
US 2020/0172937 A1 Jun. 4, 2020

Related U.S. Application Data

(60) Provisional application No. 62/513,266, filed on May 31, 2017.

(51) Int. Cl.
| | |
|---|---|
| *C12N 9/90* | (2006.01) |
| *C12P 7/06* | (2006.01) |
| *C12P 7/10* | (2006.01) |
| *C12N 1/20* | (2006.01) |
| *C12N 1/14* | (2006.01) |
| *C12N 9/92* | (2006.01) |
| *C12N 1/16* | (2006.01) |
| *C12N 15/81* | (2006.01) |

(52) U.S. Cl.
CPC .............. *C12N 9/92* (2013.01); *C12N 1/16* (2013.01); *C12N 15/81* (2013.01); *C12P 7/06* (2013.01); *C12P 7/10* (2013.01); *C12Y 503/01005* (2013.01)

(58) Field of Classification Search
CPC ................. C12N 9/90; C12P 7/10; C12P 7/06
See application file for complete search history.

(56) References Cited

U.S. PATENT DOCUMENTS 9,090,889 B2 * 7/2015 Nunn, Jr. ................. C12N 9/90
2012/0225452 A1 9/2012 Bao et al.

FOREIGN PATENT DOCUMENTS

| WO | 2003062430 A1 | 7/2003 | |
|---|---|---|---|
| WO | 2009017441 A1 | 2/2009 | |
| WO | 2010059095 A1 | 5/2010 | |
| WO | 2010074577 A1 | 7/2010 | |
| WO | 2011006126 A2 | 1/2011 | |
| WO | 2012097091 A2 | 7/2012 | |
| WO | 2012113120 A1 | 8/2012 | |
| WO | 2012135110 A1 | 10/2012 | |
| WO | 2014018552 A1 | 1/2014 | |
| WO | WO-2014018552 A1 * | 1/2014 | ............... C12P 7/56 |

OTHER PUBLICATIONS

Studer. Residue mutations and their impact on protein structure and function: detecting beneficial and pathogenic changes. Biochem. J. (2013) 449, 581-594.*
Hou et al, 2011, EBI Accession No. JF496707.
Hou et al, 2014, BMC Biotechnology 14(1), 13.
Kim et al, 2013, Biotechnol Adv 31, 851-861.
Qi et al, 2015, Frontiers in microbiology 6, 1-12.
Shen et al, 2012, Appl Biochem Biotechnol 96(4), 1079-1091.

* cited by examiner

*Primary Examiner* — Yong D Pak
(74) *Attorney, Agent, or Firm* — Eric Fechter

(57) ABSTRACT

Provided herein are recombinant host cells having a heterologous polynucleotide encoding a xylose isomerase, wherein the cells are capable of improved growth on xylose. Also described are processes of fermenting saccharified material using the recombinant cells to produce ethanol at higher yields.

24 Claims, 16 Drawing Sheets

Specification includes a Sequence Listing.

SEQUENCE LISTING

```
<160> NUMBER OF SEQ ID NOS: 187

<210> SEQ ID NO 1
<211> LENGTH: 1329
<212> TYPE: DNA
<213> ORGANISM: Unknown
<220> FEATURE:
<223> OTHER INFORMATION: Artificial DNA Sequence

<400> SEQUENCE: 1
atggctatta cccttggtgc aactgagtac ttcaaaggta taggtgccat ctcatatgaa      60
ggtcctaaaa cagacaatcc attggcattt agatggtatg acgcaaaccg tcaagtgtct     120
ggtaaaacta tgaaagaatg gttgagattt gcctgtgcct actggcattc cttcaatggt     180
tccggagcag acccgttcgg tgagccaact caccttttc cttgggatga gtcttcagac     240
ccattgacaa gggctagggc taaggccgat gctgcctttg aattcatgac caagatgggt     300
ttaccctact attgttttca tgatgtcgat gttgtagact atggtaacga tgtggcagaa     360
aatgacagaa gattacaggc aatgacttcc tacctagccg aaaaacaaaa agagtctggt     420
attcaattgt tgtgggggac cgcaaactta ttcagttcta gaaggtatat gaacggtgct     480
gctacaaacc cagactttca ggttttggct catgcaggag cacaggtcaa agctgcacta     540
gacgcaacta ttcaattagg tggtcagaac tatgttttct ggggaggtag ggaaggttac    600
atgtcactgt tgaatacaaa cacaaaacgt gagaagagc atttggctag gttttgcag     660
```

```
acggcaaggg attatgcaag gagacaaggc ttcaaaggca agttttcat cgaaccgaaa      720 ccatgtgagc ctagcaagca ccaatacgat tatgactcag aaaccgtaat cggcttctta      780
agacaatatg atctactgtc agacttcagc ctgaacattg aggttaatca cgctacatta      840
gctggtcata cttttcaaca tgaattgcaa atggctgcag atgccggttt actgggctcc      900
attgatgcaa atagaggcga ttatcagaat ggttgggata cagatcaatt tcccaacaat      960
gtccctgaat tagctgaagc aatgttggtg atcttggagg ctggtgggtt tggggggtgt    1020
ggcatcaact ttgatgctaa gataagaagg aactccaccg atcccgaaga cctgttctat    1080
gcacatattg gtggtatgga cgctttcgcc agagccttgt tagttgcaga cgcagttctt    1140
catcagtccg attacaagaa aatcagaact gagagatacg catcttttga ttctggtgcc    1200
ggtaaagagt ttgaggaagg taaacttacc ctagagaact tgagggaatt agcaattcag    1260
catggtgagc ctgcaccaag atccggtaaa caggagttgt tggagaacat attgaactat    1320
ttcattaa                                                                                     1329
```

<210> SEQ ID NO 2
<211> LENGTH: 442
<212> TYPE: PRT
<213> ORGANISM: Unknown
<220> FEATURE:
<223> OTHER INFORMATION: Artificial DNA Sequence

<400> SEQUENCE: 2

```
Met Ala Ile Thr Leu Gly Ala Thr Glu Tyr Phe Lys Gly Ile Gly Ala
1               5                   10                  15

Ile Ser Tyr Glu Gly Pro Lys Thr Asp Asn Pro Leu Ala Phe Arg Trp
            20                  25                  30

Tyr Asp Ala Asn Arg Gln Val Ser Gly Lys Thr Met Lys Glu Trp Leu
        35                  40                  45

Arg Phe Ala Cys Ala Tyr Trp His Ser Phe Asn Gly Ser Gly Ala Asp
    50                  55                  60

Pro Phe Gly Glu Pro Thr His Leu Phe Pro Trp Asp Glu Ser Ser Asp
65                  70                  75                  80

Pro Leu Thr Arg Ala Arg Ala Lys Ala Asp Ala Ala Phe Glu Phe Met
                85                  90                  95

Thr Lys Met Gly Leu Pro Tyr Tyr Cys Phe His Asp Val Asp Val Val
            100                 105                 110

Asp Tyr Gly Asn Asp Val Ala Glu Asn Asp Arg Arg Leu Gln Ala Met
        115                 120                 125

Thr Ser Tyr Leu Ala Glu Lys Gln Lys Glu Ser Gly Ile Gln Leu Leu
    130                 135                 140

Trp Gly Thr Ala Asn Leu Phe Ser Ser Arg Arg Tyr Met Asn Gly Ala
145                 150                 155                 160

Ala Thr Asn Pro Asp Phe Gln Val Leu Ala His Ala Gly Ala Gln Val
                165                 170                 175

Lys Ala Ala Leu Asp Ala Thr Ile Gln Leu Gly Gly Gln Asn Tyr Val
            180                 185                 190

Phe Trp Gly Gly Arg Glu Gly Tyr Met Ser Leu Leu Asn Thr Asn Thr
        195                 200                 205

Lys Arg Glu Lys Glu His Leu Ala Arg Phe Leu Gln Thr Ala Arg Asp
    210                 215                 220

Tyr Ala Arg Arg Gln Gly Phe Lys Gly Lys Phe Phe Ile Glu Pro Lys
225                 230                 235                 240
```

```
Pro Cys Glu Pro Ser Lys His Gln Tyr Asp Tyr Asp Ser Glu Thr Val
                245                 250                 255

Ile Gly Phe Leu Arg Gln Tyr Asp Leu Leu Ser Asp Phe Ser Leu Asn
            260                 265                 270

Ile Glu Val Asn His Ala Thr Leu Ala Gly His Thr Phe Gln His Glu
        275                 280                 285

Leu Gln Met Ala Ala Asp Ala Gly Leu Leu Gly Ser Ile Asp Ala Asn
    290                 295                 300

Arg Gly Asp Tyr Gln Asn Gly Trp Asp Thr Asp Gln Phe Pro Asn Asn
305                 310                 315                 320

Val Pro Glu Leu Ala Glu Ala Met Leu Val Ile Leu Glu Ala Gly Gly
                325                 330                 335

Phe Gly Gly Gly Gly Ile Asn Phe Asp Ala Lys Ile Arg Arg Asn Ser
            340                 345                 350

Thr Asp Pro Glu Asp Leu Phe Tyr Ala His Ile Gly Gly Met Asp Ala
        355                 360                 365

Phe Ala Arg Ala Leu Leu Val Ala Asp Ala Val Leu His Gln Ser Asp
    370                 375                 380

Tyr Lys Lys Ile Arg Thr Glu Arg Tyr Ala Ser Phe Asp Ser Gly Ala
385                 390                 395                 400

Gly Lys Glu Phe Glu Glu Gly Lys Leu Thr Leu Glu Asn Leu Arg Glu
                405                 410                 415

Leu Ala Ile Gln His Gly Glu Pro Ala Pro Arg Ser Gly Lys Gln Glu
            420                 425                 430

Leu Leu Glu Asn Ile Leu Asn Tyr Phe Ile
        435                 440

<210> SEQ ID NO 3
<211> LENGTH: 1323
<212> TYPE: DNA
<213> ORGANISM: Burkholderia cenocepacia

<400> SEQUENCE: 3
atgtcctatt tcgaacacat tccagccatt agatatgaag gtccacaatc cgacaaccct      60
cttgcctacc atcattacga tccagacaaa agagtcctag gtaagacttt ggctgaacac     120
ctgagaattg ctgtctgtta ctggcatacc tttgtatggc caggacatga catctttggt     180
caagccgctt tcaggagacc ctggcagcaa cctggtgacg cattagaaag agcccgtatg     240
aaagcagacg ctgcttttga gttctttact aagttaggca ccccattcta caccttccac     300
gacacagacg tcgctccgga aggtgactct ttgagagagt atgcagccaa tttcgctaga     360
atggtcgact acttaggtga aagacagcag gcctcaggcg tcagattgtt gtggggcacc     420
gccaacttgt tttcacatcc aagattcgct gccggtgccg caacaaaccc aaatcccgat     480
gtatttgctt gggctgcaac ccaagtttgt catgccttag atgccactca tagactagga     540
ggtgagaatt acgtcttatg ggtggtaggg gaaggttacg aaacactatt gaatacggat     600
ctgaagagag aacgtgacca gtttgcaaga tttctgtcta tggtagtcga acacaaacat     660
aggattggct tcaaaggagc attgttgatc gaacctaagc ctcaagaacc cacaaaacat     720
caatatgact acgatgtcgc tacggttcat ggcttcttag ttcagtatgg tctacaaaat     780
gagattagag tcaacattga ggcaaaccac gctactcttg caggccactc atttcatcat     840
gaaattgcaa atgccttcgc actaggtgta ttcggaagtg ttgatgcaaa cagaggtgat     900
ccacaaaacg gatgggatac agatcagttt ccgaactcag ttgaagaatt gacattagcc     960
```

-continued

```
ttctatgaaa tactacgtca tggaggtttc accacaggcg gtatgaactt tgatgcaaaa      1020
gtgcgtagac agtcaattga ccctgaagat ttgttctatg ccatgttgg tgctattgat       1080 gtgttggcct tggcattaga aagagctgcc gtactagtgg aaaatgatag attggatgca      1140
ttgagacgtc aaagatacgc tcagtgggat gatgcttttg gtaggaaaat cctagcagga     1200 ggatataccct tggaatcttt agctgccgac gctcttgcta ggggagtgga cccacaacat    1260
gcatctggtg cacaggaaag actggaaaac atcgtcaatc aagcaatcta tggtttaagg    1320
taa                                                                    1323
```

<210> SEQ ID NO 4
<211> LENGTH: 440
<212> TYPE: PRT
<213> ORGANISM: Burkholderia cenocepacia

<400> SEQUENCE: 4

```
Met Ser Tyr Phe Glu His Ile Pro Ala Ile Arg Tyr Glu Gly Pro Gln
1               5                   10                  15

Ser Asp Asn Pro Leu Ala Tyr His Tyr Asp Pro Asp Lys Arg Val
            20                  25                  30

Leu Gly Lys Thr Leu Ala Glu His Leu Arg Ile Ala Val Cys Tyr Trp
        35                  40                  45

His Thr Phe Val Trp Pro Gly His Asp Ile Phe Gly Gln Ala Ala Phe
    50                  55                  60

Arg Arg Pro Trp Gln Gln Pro Gly Asp Ala Leu Glu Arg Ala Arg Met
65                  70                  75                  80

Lys Ala Asp Ala Ala Phe Glu Phe Phe Thr Lys Leu Gly Thr Pro Phe
                85                  90                  95

Tyr Thr Phe His Asp Thr Asp Val Ala Pro Glu Gly Asp Ser Leu Arg
            100                 105                 110

Glu Tyr Ala Ala Asn Phe Ala Arg Met Val Asp Tyr Leu Gly Glu Arg
        115                 120                 125

Gln Gln Ala Ser Gly Val Arg Leu Leu Trp Gly Thr Ala Asn Leu Phe
    130                 135                 140

Ser His Pro Arg Phe Ala Ala Gly Ala Ala Thr Asn Pro Asn Pro Asp
145                 150                 155                 160

Val Phe Ala Trp Ala Ala Thr Gln Val Cys His Ala Leu Asp Ala Thr
                165                 170                 175

His Arg Leu Gly Gly Glu Asn Tyr Val Leu Trp Gly Gly Arg Glu Gly
            180                 185                 190

Tyr Glu Thr Leu Leu Asn Thr Asp Leu Lys Arg Glu Arg Asp Gln Phe
        195                 200                 205

Ala Arg Phe Leu Ser Met Val Val Glu His Lys His Arg Ile Gly Phe
    210                 215                 220

Lys Gly Ala Leu Leu Ile Glu Pro Lys Pro Gln Glu Pro Thr Lys His
225                 230                 235                 240

Gln Tyr Asp Tyr Asp Val Ala Thr Val His Gly Phe Leu Val Gln Tyr
                245                 250                 255

Gly Leu Gln Asn Glu Ile Arg Val Asn Ile Glu Ala Asn His Ala Thr
            260                 265                 270

Leu Ala Gly His Ser Phe His His Glu Ile Ala Asn Ala Phe Ala Leu
        275                 280                 285

Gly Val Phe Gly Ser Val Asp Ala Asn Arg Gly Asp Pro Gln Asn Gly
    290                 295                 300
```

| Trp | Asp | Thr | Asp | Gln | Phe | Pro | Asn | Ser | Val | Glu | Glu | Leu | Thr | Leu | Ala |
| 305 | | | | 310 | | | | | 315 | | | | | 320 | |

| Phe | Tyr | Glu | Ile | Leu | Arg | His | Gly | Gly | Phe | Thr | Thr | Gly | Gly | Met | Asn |
| | | | | 325 | | | | | 330 | | | | | 335 | |

| Phe | Asp | Ala | Lys | Val | Arg | Arg | Gln | Ser | Ile | Asp | Pro | Glu | Asp | Leu | Phe |
| | | | 340 | | | | | 345 | | | | | 350 | | |

| Tyr | Gly | His | Val | Gly | Ala | Ile | Asp | Val | Leu | Ala | Leu | Ala | Leu | Glu | Arg |
| | | 355 | | | | | 360 | | | | | 365 | | | |

| Ala | Ala | Val | Leu | Val | Glu | Asn | Asp | Arg | Leu | Asp | Ala | Leu | Arg | Arg | Gln |
| | 370 | | | | | 375 | | | | | 380 | | | | |

| Arg | Tyr | Ala | Gln | Trp | Asp | Asp | Ala | Phe | Gly | Arg | Lys | Ile | Leu | Ala | Gly |
| 385 | | | | 390 | | | | | 395 | | | | | 400 | |

| Gly | Tyr | Thr | Leu | Glu | Ser | Leu | Ala | Ala | Asp | Ala | Leu | Ala | Arg | Gly | Val |
| | | | | 405 | | | | | 410 | | | | | 415 | |

| Asp | Pro | Gln | His | Ala | Ser | Gly | Ala | Gln | Glu | Arg | Leu | Glu | Asn | Ile | Val |
| | | | 420 | | | | | 425 | | | | | 430 | | |

| Asn | Gln | Ala | Ile | Tyr | Gly | Leu | Arg |
| | | | 435 | | | | 440 |

<210> SEQ ID NO 5
<211> LENGTH: 1332
<212> TYPE: DNA
<213> ORGANISM: Bacillus sp-18312

<400> SEQUENCE: 5

```
atggcttact tgagacggt caacaagata caatttgaag gagcaagtag taccaaccct      60
tttgctttca agtattacaa tccagaagag gttgtcaatg gtcagaaaat ggaggagtta     120
ttgaggttta gcgttgctta ctggcatact tttacagcag atggtacaga tcccttcggt     180
gccggaacag ccattcgttc ttgggatcac ttccaaggta tggacctggc caaagcaagg     240
gttgaagctg ccttcgaatt gttcgaaaag cttaatgtgc cgttcttcgc attccatgac     300
gtcgatatcg ctccagaggg tagaacacta aagaaacaa atgaaaatca agatgagatt     360
gtaggaatga tcaaagagta catgaaaaacc agtaaagcca atttgctttg gaacactgcc     420
aatatgttta caaatccgag atacgttcac ggtggagcca cttctcccaa tgcagatgtt     480
tttgcttaca gtgctgctaa agttaagaaa gctctggaag ttgcaaagga attaggggct     540
gagaactatg tcttctgggg aggtagagaa ggttatgaga ctttgctgaa tacggacatg     600
aaacttgagc aggacaattt ggctaggttc tttcatatgg cagtcgatta tgcaaaagaa     660
attggcttaa acgttccatt cttgatagag cctaagccaa aggaaccaac aaaacatcaa     720
tacgatttcg atgtggctac tggtttagct tttctacaga aatacgattt gaccgactac     780
ttcaagttta acatagaggc caatcatgcc acacttgccg acatacatt tgaacatgaa     840
ttgcgtaccg caaggatcaa tggcatgctt ggttctgttg acgcaaatca aggtgatacc     900
ttattgggtt gggataccga tgagttccct acagacttgt attcaaatac attggctatg     960
tatgaaatct tgaagaatgg tggcttaggc aaaggtggct tgaatttcga tgccaaggta    1020
aggagaggta gttttgaagc agatgactta ttccatgctc atattgctgg tatggatgcc    1080
tttgcaattg gtctaaaggt ggcaagtcgt atgattgaag atagagtttt agatggtttc    1140
gttgaagaaa gatacagttc atacaatgaa ggtattggtc ttgacatagt agaaggtagg    1200
gcagacttta aaagctgga ggctcacgca cttcaactga aggagatcaa aaacacttct    1260
ggtaggactg aaaggttaaa ggccgtcatc aatcaatact tattggaaac cttgacatcc    1320
```
gtgaaggctt aa                                                              1332

<210> SEQ ID NO 6
<211> LENGTH: 443
<212> TYPE: PRT
<213> ORGANISM: Bacillus sp-18312

<400> SEQUENCE: 6

```
Met Ala Tyr Phe Glu Thr Val Asn Lys Ile Gln Phe Glu Gly Ala Ser
1               5                   10                  15

Ser Thr Asn Pro Phe Ala Phe Lys Tyr Tyr Asn Pro Glu Glu Val Val
                20                  25                  30

Asn Gly Gln Lys Met Glu Glu Leu Leu Arg Phe Ser Val Ala Tyr Trp
            35                  40                  45

His Thr Phe Thr Ala Asp Gly Thr Asp Pro Phe Gly Ala Gly Thr Ala
        50                  55                  60

Ile Arg Ser Trp Asp His Phe Gln Gly Met Asp Leu Ala Lys Ala Arg
65                  70                  75                  80

Val Glu Ala Ala Phe Glu Leu Phe Glu Lys Leu Asn Val Pro Phe Phe
                85                  90                  95

Ala Phe His Asp Val Asp Ile Ala Pro Glu Gly Arg Thr Leu Lys Glu
            100                 105                 110

Thr Asn Glu Asn Gln Asp Glu Ile Val Gly Met Ile Lys Glu Tyr Met
        115                 120                 125

Lys Thr Ser Lys Ala Asn Leu Leu Trp Asn Thr Ala Asn Met Phe Thr
130                 135                 140

Asn Pro Arg Tyr Val His Gly Gly Ala Thr Ser Pro Asn Ala Asp Val
145                 150                 155                 160

Phe Ala Tyr Ser Ala Ala Lys Val Lys Lys Ala Leu Glu Val Ala Lys
                165                 170                 175

Glu Leu Gly Ala Glu Asn Tyr Val Phe Trp Gly Gly Arg Glu Gly Tyr
            180                 185                 190

Glu Thr Leu Leu Asn Thr Asp Met Lys Leu Glu Gln Asp Asn Leu Ala
        195                 200                 205

Arg Phe Phe His Met Ala Val Asp Tyr Ala Lys Glu Ile Gly Leu Asn
210                 215                 220

Val Pro Phe Leu Ile Glu Pro Lys Pro Lys Glu Pro Thr Lys His Gln
225                 230                 235                 240

Tyr Asp Phe Asp Val Ala Thr Gly Leu Ala Phe Leu Gln Lys Tyr Asp
                245                 250                 255

Leu Thr Asp Tyr Phe Lys Phe Asn Ile Glu Ala Asn His Ala Thr Leu
            260                 265                 270

Ala Gly His Thr Phe Glu His Glu Leu Arg Thr Ala Arg Ile Asn Gly
        275                 280                 285

Met Leu Gly Ser Val Asp Ala Asn Gln Gly Asp Thr Leu Leu Gly Trp
290                 295                 300

Asp Thr Asp Glu Phe Pro Thr Asp Leu Tyr Ser Asn Thr Leu Ala Met
305                 310                 315                 320

Tyr Glu Ile Leu Lys Asn Gly Gly Leu Gly Lys Gly Gly Leu Asn Phe
                325                 330                 335

Asp Ala Lys Val Arg Arg Gly Ser Phe Glu Ala Asp Leu Phe His
            340                 345                 350

Ala His Ile Ala Gly Met Asp Ala Phe Ala Ile Gly Leu Lys Val Ala
        355                 360                 365
```

Ser Arg Met Ile Glu Asp Arg Val Leu Asp Gly Phe Val Glu Arg
    370                 375                 380

Tyr Ser Ser Tyr Asn Glu Gly Ile Gly Leu Asp Ile Val Glu Gly Arg
385                 390                 395                 400

Ala Asp Phe Arg Lys Leu Glu Ala His Ala Leu Gln Leu Lys Glu Ile
                405                 410                 415

Lys Asn Thr Ser Gly Arg Thr Glu Arg Leu Lys Ala Val Ile Asn Gln
            420                 425                 430

Tyr Leu Leu Glu Thr Leu Thr Ser Val Lys Ala
        435                 440

<210> SEQ ID NO 7
<211> LENGTH: 1302
<212> TYPE: DNA
<213> ORGANISM: Roseinatronobacter monicus

<400> SEQUENCE: 7
atgacagact tctttgctgg cattccacaa ttgacttacc aaggcacgga tgctacttca      60
gattttgctt ttaggcacta caagccggat gaagttgtgt tgggtaggag aatggaagac     120
catctaagat ttgctgtttg ctactggcac aatttcgctt ggccaggtaa cgatcctttt     180
ggtggacaaa cttttcaaag accctggttt ggcgatacaa tggaacacgc taagttgaag     240
gcagatgttg ctttcgagat gtttaggata ttgaataccc ctactttgt tttccatgac     300 gccgatatgc gtcccgaggg cgactcattc gcacaaaaca caagaaactt ggaagaaatg     360
acagactaca ttgcagccaa aatggaggct ggtggaccca agttactttg ggggacagcc     420
aacttgtttt ctcataggag gtacatgtca ggtgcagcta caaatccgga tccggatatc     480
tttgcattct ctgctgccac tgtcaaaact tgtatggacg ccactcatag gttaaacggt     540
gaaaactatg tcttatgggg aggtcgtgaa ggctatgaaa ccctttgaa cacagatcta     600 tcaaaagagt tggatcacat gggtaggttt tgagtatgg tcgttgacta caaacacaag     660
attggattca aaggtgccat tttgattgaa ccaaaacctc aggaaccaac caaacaccag     720
tacgactatg acgtagctac agttttgga ttcctacaaa gattcggttt ggaaaaagaa     780
gttaaggtca acatagaaca aggccatgcc atattggctg gcatagctt cgaacatgag     840 atagccctgg cagcttcatt aggcatcttt ggtagcatag atatgaatag aaacgactac     900
caatctggtt gggatacaga tcaattcccc aacaatacac ctgaagtcgc tctggcctac     960
tatgagatat tgagagcagg aggttttaca acaggaggga ccaactttga cgcaaaactt    1020
agacgtcagt ctttggacgc agaggactta atcttagctc acgcaggagc tatggacgta    1080
tgcgctagag gtttgaaagc tgccgctgcc atgttagaag atggcaagct tgaagcagcc    1140
agagctgcta gatatgctgg atgggatacg ccagaagcac aagccatgtt acattccaat    1200
ttggatagaa tcgcagaaga tgtattgaac catgatgtta atcccaaccc gagaagtggt    1260
aggcaagagc gtttggaaaa tctagtcaat agatacttgt aa                       1302

<210> SEQ ID NO 8
<211> LENGTH: 433
<212> TYPE: PRT
<213> ORGANISM: Roseinatronobacter monicus

<400> SEQUENCE: 8

Met Thr Asp Phe Phe Ala Gly Ile Pro Gln Leu Thr Tyr Gln Gly Thr
1               5                   10                  15

Asp Ala Thr Ser Asp Phe Ala Phe Arg His Tyr Lys Pro Asp Glu Val

```
                20                  25                  30
Val Leu Gly Arg Arg Met Glu Asp His Leu Arg Phe Ala Val Cys Tyr
            35                  40                  45
Trp His Asn Phe Ala Trp Pro Gly Asn Asp Pro Phe Gly Gly Gln Thr
        50                  55                  60
Phe Gln Arg Pro Trp Phe Gly Asp Thr Met Glu His Ala Lys Leu Lys
65                  70                  75                  80
Ala Asp Val Ala Phe Glu Met Phe Arg Ile Leu Asn Thr Pro Tyr Phe
                85                  90                  95
Cys Phe His Asp Ala Asp Met Arg Pro Glu Gly Asp Ser Phe Ala Gln
            100                 105                 110
Asn Thr Arg Asn Leu Glu Glu Met Thr Asp Tyr Ile Ala Ala Lys Met
        115                 120                 125
Glu Ala Gly Gly Pro Lys Leu Leu Trp Gly Thr Ala Asn Leu Phe Ser
130                 135                 140
His Arg Arg Tyr Met Ser Gly Ala Ala Thr Asn Pro Asp Pro Asp Ile
145                 150                 155                 160
Phe Ala Phe Ser Ala Ala Thr Val Lys Thr Cys Met Asp Ala Thr His
                165                 170                 175
Arg Leu Asn Gly Glu Asn Tyr Val Leu Trp Gly Arg Glu Gly Tyr
            180                 185                 190
Glu Thr Leu Leu Asn Thr Asp Leu Ser Lys Glu Leu Asp His Met Gly
        195                 200                 205
Arg Phe Leu Ser Met Val Val Asp Tyr Lys His Lys Ile Gly Phe Lys
210                 215                 220
Gly Ala Ile Leu Ile Glu Pro Lys Pro Gln Glu Pro Thr Lys His Gln
225                 230                 235                 240
Tyr Asp Tyr Asp Val Ala Thr Val Phe Gly Phe Leu Gln Arg Phe Gly
                245                 250                 255
Leu Glu Lys Glu Val Lys Val Asn Ile Glu Gln Gly His Ala Ile Leu
            260                 265                 270
Ala Gly His Ser Phe Glu His Glu Ile Ala Leu Ala Ala Ser Leu Gly
        275                 280                 285
Ile Phe Gly Ser Ile Asp Met Asn Arg Asn Asp Tyr Gln Ser Gly Trp
290                 295                 300
Asp Thr Asp Gln Phe Pro Asn Asn Thr Pro Glu Val Ala Leu Ala Tyr
305                 310                 315                 320
Tyr Glu Ile Leu Arg Ala Gly Gly Phe Thr Thr Gly Gly Thr Asn Phe
                325                 330                 335
Asp Ala Lys Leu Arg Arg Gln Ser Leu Asp Ala Glu Asp Leu Ile Leu
            340                 345                 350
Ala His Ala Gly Ala Met Asp Val Cys Ala Arg Gly Leu Lys Ala Ala
        355                 360                 365
Ala Ala Met Leu Glu Asp Gly Lys Leu Glu Ala Arg Ala Ala Arg
370                 375                 380
Tyr Ala Gly Trp Asp Thr Pro Glu Ala Gln Ala Met Leu His Ser Asn
385                 390                 395                 400
Leu Asp Arg Ile Ala Glu Asp Val Leu Asn His Asp Val Asn Pro Asn
                405                 410                 415
Pro Arg Ser Gly Arg Gln Glu Arg Leu Glu Asn Leu Val Asn Arg Tyr
            420                 425                 430

Leu
```

<210> SEQ ID NO 9
<211> LENGTH: 1317
<212> TYPE: DNA
<213> ORGANISM: Burkholderia glathei

<400> SEQUENCE: 9

```
atgtcttact tcgagcattt accagccgtt agatacgagg gtcctcagtc agacaatcct      60
tttgcttata gacattacga tcgtgataag ttggtgttgg gcaagagaat ggaagaccac     120
ttgagattgg cagtctgtta ctggcacact tttgtttggc ctggagtcga tatgtttggt     180
caaggtactt ttcatcgtcc ctggcagcaa ccaggtgacg ctattgaacg tgctcacgtc     240
aaagcagata gcgcattcga gttttctca aacttggtg ctccctacta tacgtttcat      300
gatacagatg ttgccctga aggtgattcc attaagcatt atgtcaacaa ctttaagggt     360
gtcacagact atttggctgc caaacaggag caaacaggca taaagcttct gtggggtaca     420
gcaaacttgt tcagtcatcc aagatacgca gctggagccg ctacaaatcc aaacccagaa     480
gttttcgcat tcgcagcaac ccaagtcttc aagcattag aagccactca caggctaggc      540
ggtgagaact atgtactgtg gggtggaaga gaaggatatg atactctgtt gaacacagat     600
ttgaaaagag aacgtgatca attgggaaga ttcctgaata tggtcgttga acataaacac     660
aaaactgggt tcaaaggtgc cttgttaatc gagccaaagc tcaagaacc aactaagcat      720
caatatgatt acgatgtggc aactgttcat ggcttcttag cacagtttgg actacaaaac     780
gagattagag tcaacattga agcaaaccat gccactctgg ctggacattc ttttcaccat     840
gagattgcta cggcttacgc cttgggtatc tttggtagtg tggacgcaaa cagaggcgac     900
ccacagaatg gatgggatac cgaccaattc ccaaattctg tagaagaatt gacattggcc     960
ttgtatgaga tactacgtca tggcggtttt tctactgggg gtatgaactt tgacgcaaag    1020
gttcgtcgtc agtcagtggc accggaagat tgttctttg gccatattgg agcaatagat    1080
gtcattgctt tggcttttgga aagagctgct actatggttg aaaatgacaa attggcagag    1140
ttcaagactc aaagatacgt aggatgggat actgagttcg gaaggaagat attgtccgga    1200
ggttattctt tagaatctct agcaatggac gcactgggta aagggtgaa tccacaacac     1260
gtgtccggtc aacaggaatt gttggagaac atagttaatc gtgccatcta caaataa      1317
```

<210> SEQ ID NO 10
<211> LENGTH: 438
<212> TYPE: PRT
<213> ORGANISM: Burkholderia glathei

<400> SEQUENCE: 10

```
Met Ser Tyr Phe Glu His Leu Pro Ala Val Arg Tyr Glu Gly Pro Gln
1               5                   10                  15

Ser Asp Asn Pro Phe Ala Tyr Arg His Tyr Asp Arg Asp Lys Leu Val
            20                  25                  30

Leu Gly Lys Arg Met Glu Asp His Leu Arg Leu Ala Val Cys Tyr Trp
        35                  40                  45

His Thr Phe Val Trp Pro Gly Val Asp Met Phe Gly Gln Gly Thr Phe
    50                  55                  60

His Arg Pro Trp Gln Gln Pro Gly Asp Ala Ile Glu Arg Ala His Val
65                  70                  75                  80

Lys Ala Asp Ser Ala Phe Glu Phe Phe Ser Lys Leu Gly Ala Pro Tyr
                85                  90                  95

Tyr Thr Phe His Asp Thr Asp Val Ala Pro Glu Gly Asp Ser Ile Lys
```

His Tyr Val Asn Asn Phe Lys Gly Val Thr Asp Tyr Leu Ala Ala Lys
                100                 105                 110

Gln Glu Gln Thr Gly Ile Lys Leu Leu Trp Gly Thr Ala Asn Leu Phe
    115                 120                 125

Ser His Pro Arg Tyr Ala Ala Gly Ala Ala Thr Asn Pro Asn Pro Glu
145                 150                 155                 160

Val Phe Ala Phe Ala Ala Thr Gln Val Phe Gln Ala Leu Glu Ala Thr
                165                 170                 175

His Arg Leu Gly Gly Glu Asn Tyr Val Leu Trp Gly Gly Arg Glu Gly
            180                 185                 190

Tyr Asp Thr Leu Leu Asn Thr Asp Leu Lys Arg Glu Arg Asp Gln Leu
        195                 200                 205

Gly Arg Phe Leu Asn Met Val Val Glu His Lys His Lys Thr Gly Phe
    210                 215                 220

Lys Gly Ala Leu Leu Ile Glu Pro Lys Pro Gln Glu Pro Thr Lys His
225                 230                 235                 240

Gln Tyr Asp Tyr Asp Val Ala Thr Val His Gly Phe Leu Ala Gln Phe
                245                 250                 255

Gly Leu Gln Asn Glu Ile Arg Val Asn Ile Glu Ala Asn His Ala Thr
            260                 265                 270

Leu Ala Gly His Ser Phe His His Glu Ile Ala Thr Ala Tyr Ala Leu
        275                 280                 285

Gly Ile Phe Gly Ser Val Asp Ala Asn Arg Gly Asp Pro Gln Asn Gly
    290                 295                 300

Trp Asp Thr Asp Gln Phe Pro Asn Ser Val Glu Glu Leu Thr Leu Ala
305                 310                 315                 320

Leu Tyr Glu Ile Leu Arg His Gly Gly Phe Ser Thr Gly Gly Met Asn
                325                 330                 335

Phe Asp Ala Lys Val Arg Arg Gln Ser Val Ala Pro Glu Asp Leu Phe
            340                 345                 350

Phe Gly His Ile Gly Ala Ile Asp Val Ile Ala Leu Ala Leu Glu Arg
        355                 360                 365

Ala Ala Thr Met Val Glu Asn Asp Lys Leu Ala Glu Phe Lys Thr Gln
    370                 375                 380

Arg Tyr Val Gly Trp Asp Thr Glu Phe Gly Arg Lys Ile Leu Ser Gly
385                 390                 395                 400

Gly Tyr Ser Leu Glu Ser Leu Ala Met Asp Ala Leu Gly Arg Arg Val
                405                 410                 415

Asn Pro Gln His Val Ser Gly Gln Gln Glu Leu Leu Glu Asn Ile Val
            420                 425                 430

Asn Arg Ala Ile Tyr Lys
        435

<210> SEQ ID NO 11
<211> LENGTH: 1323
<212> TYPE: DNA
<213> ORGANISM: Herbaspirillum rhizosphaerae

<400> SEQUENCE: 11
atgtcctatt tcgaacacat tccaccgatt cattatgaag gtccagattc cgacaaccct         60 cttgccttc atcattacga caaaaccaag aaagtcctag gtaagacttt ggaagctcac        120
ctgagaattg ctgtctgtta ctggcatacc tttgtatggc caggagcaga tgttttggt        180

```
catgggcctt tcaggagacc ctggcacgaa cctggtgacg caatggaaag agccaagcag    240
aaagcagacg ctgcttttga gttgttttct aagttaggca ccccatacta caccttccac    300
gacacagacg cagctccgga aggtaggaat ttgaaagagt attcagagaa tttcgctaga    360
atggtcgact acttagctag aaaacagcag gactcaggcg tcggtttgtt gtggggcacc    420
gccaacttgt tttcacatcc aagatacgct gccggtgccg caacaaaccc aaatcccgaa    480
gtatttgctt tgctgcagc ccaagttaga catgccttag atgccactca tcaactagga     540
ggtgagaatt acgtcttatg gggtggtagg gaaggttacg atacactatt gaatacggaa    600
ctgagcagag aacgtgagca gtttgcaaga tttctgcata tggtagtcga acacgctcat    660
aggattggct tcaaaggaac cttgttgatc gaacctaagc ctcaagaacc cacaaaacat    720
caatatgact acgatgtcgc tagcgttcat ggcttcttaa ctcagtatgg tctacaaaat    780
gagattagag tcaacattga ggcaaaccac gctactcttg caggccactc atttcatcat    840
gaaattgcta ctgccttcgc actaggtgta ttcggaagtg ttgatgcaaa cagaggtgat    900
ccacaaaacg gatgggatac agatcagttt ccgaactcag ttgaagaatt gacattagcc    960
ttctatgaaa tactacgtca tggaggtttc accacaggcg gtatgaactt tgatgcaaaa   1020
gtgcgtagac agtcaattga cgcagaagat ttgttctatg ccatattggt gctattgat    1080
aacttggcct tggcagttga agagctgcc aaattgatcg aacatgatag attggaacag    1140
tttagacagc aaagatacgc tggctgggat acagaatttg gtaggaaaat cctagcagga    1200
ggatatagtt tgacatcttt gactgccgac gctcttgcta ggggactgga cccacaacat    1260
gcatctggta gacaggaata tctggaaagc gtggtcaatc aagcaatcta tggtggaagg    1320
taa                                                                  1323
```

<210> SEQ ID NO 12
<211> LENGTH: 440
<212> TYPE: PRT
<213> ORGANISM: Herbaspirillum rhizosphaerae

<400> SEQUENCE: 12

Met Ser Tyr Phe Glu His Ile Pro Pro Ile His Tyr Glu Gly Pro Asp
1               5                   10                  15

Ser Asp Asn Pro Leu Ala Phe His His Tyr Asp Lys Thr Lys Lys Val
            20                  25                  30

Leu Gly Lys Thr Leu Glu Ala His Leu Arg Ile Ala Val Cys Tyr Trp
        35                  40                  45

His Thr Phe Val Trp Pro Gly Ala Asp Val Phe Gly His Gly Ala Phe
    50                  55                  60

Arg Arg Pro Trp His Glu Pro Gly Asp Ala Met Glu Arg Ala Lys Gln
65                  70                  75                  80

Lys Ala Asp Ala Ala Phe Glu Leu Phe Ser Lys Leu Gly Thr Pro Tyr
                85                  90                  95

Tyr Thr Phe His Asp Thr Asp Ala Ala Pro Glu Gly Arg Asn Leu Lys
            100                 105                 110

Glu Tyr Ser Glu Asn Phe Ala Arg Met Val Asp Tyr Leu Ala Arg Lys
        115                 120                 125

Gln Gln Asp Ser Gly Val Gly Leu Leu Trp Gly Thr Ala Asn Leu Phe
    130                 135                 140

Ser His Pro Arg Tyr Ala Ala Gly Ala Ala Thr Asn Pro Asn Pro Glu
145                 150                 155                 160

Val Phe Ala Phe Ala Ala Ala Gln Val Arg His Ala Leu Asp Ala Thr

```
                165                 170                 175
His Gln Leu Gly Gly Glu Asn Tyr Val Leu Trp Gly Gly Arg Glu Gly
            180                 185                 190

Tyr Asp Thr Leu Leu Asn Thr Glu Leu Ser Arg Glu Arg Glu Gln Phe
        195                 200                 205

Ala Arg Phe Leu His Met Val Val Glu His Ala His Arg Ile Gly Phe
    210                 215                 220

Lys Gly Thr Leu Leu Ile Glu Pro Lys Pro Gln Glu Pro Thr Lys His
225                 230                 235                 240

Gln Tyr Asp Tyr Asp Val Ala Ser Val His Gly Phe Leu Thr Gln Tyr
                245                 250                 255

Gly Leu Gln Asn Glu Ile Arg Val Asn Ile Glu Ala Asn His Ala Thr
            260                 265                 270

Leu Ala Gly His Ser Phe His His Glu Ile Ala Thr Ala Phe Ala Leu
        275                 280                 285

Gly Val Phe Gly Ser Val Asp Ala Asn Arg Gly Asp Pro Gln Asn Gly
    290                 295                 300

Trp Asp Thr Asp Gln Phe Pro Asn Ser Val Glu Glu Leu Thr Leu Ala
305                 310                 315                 320

Phe Tyr Glu Ile Leu Arg His Gly Gly Phe Thr Thr Gly Gly Met Asn
                325                 330                 335

Phe Asp Ala Lys Val Arg Arg Gln Ser Ile Asp Ala Glu Asp Leu Phe
            340                 345                 350

Tyr Gly His Ile Gly Ala Ile Asp Asn Leu Ala Leu Ala Val Glu Arg
        355                 360                 365

Ala Ala Lys Leu Ile Glu His Asp Arg Leu Glu Gln Phe Arg Gln Gln
    370                 375                 380

Arg Tyr Ala Gly Trp Asp Thr Glu Phe Gly Arg Lys Ile Leu Ala Gly
385                 390                 395                 400

Gly Tyr Ser Leu Thr Ser Leu Thr Ala Asp Ala Leu Ala Arg Gly Leu
                405                 410                 415

Asp Pro Gln His Ala Ser Gly Arg Gln Glu Tyr Leu Glu Ser Val Val
            420                 425                 430

Asn Gln Ala Ile Tyr Gly Gly Arg
        435                 440

<210> SEQ ID NO 13
<211> LENGTH: 1323
<212> TYPE: DNA
<213> ORGANISM: Viridibacillus arvi

<400> SEQUENCE: 13
atgtcctact tgaacatat  ccctactatt agatacgagg gtcctcaatc agataatcca      60
ttggcatatc accactatga tagatctaag agagttctag gtaaaactct agaagaacac     120
ttaaggattg ccgtgtgtta ctggcatact tttgtgtggc caggtgttga catttttcggt    180 cagggcacat ttgaaagacc atggcaacaa ccaggcgacg ccatggagag agctcaccag    240
aaagcagatg cagcatttga attgttttcc aaacttggta ccccatacta caccttccac    300
gatacagacg ttgctccgga aggttcatca ttgaaagaat actctgaaaa ctttgctaga    360
atctcagatt acttagccag aaaacaacag gatactggag tcaagctttt gtggggaca     420 gccaacttgt tttcccaccc aagatatgct ggtggtgctg ctacctcccc caatcccgag    480
gtttttgctt ttgctgccac tcaagtttgt cacgctctag atgccactca agattagga    540
```

```
ggagaaaact acgttttgtg gggagggagg gaaggttatg atactttgct gaacacagat    600
ctaggaagag aaagggaaca attcgctaga ttcttgaata tggtggtaga acacgcacat    660
aagattggct ttaagggtac tctgttgatt gaaccaaaac ctcaagaacc aactaaacat    720
caatatgatt acgacgttgc cgcagttcat ggcttttga  cccaatatgg attgcaaaac    780
gacattaggg taaacattga agcaaatcat gctacactag ccggtcacag tttccaccac    840
gaaatcgctt ctgcatttgc tttaggcatc tttggttctg ttgatgcaaa tagggggtgat    900 cctcaaaacg gttgggacac cgaccaattt ccaaattccg tcgaagaact tactttagcc    960
ttttacgaga tattgaagca tggtggattc actacaggtg gtatgaactt tgacgccaaa   1020
gtcagaaggc agtccgtgga tgctgaagat ttgttctatg gtcacatatc tgcaatcgac   1080
aacttagcct tagcagtgga aagagcagct gttttgattg aaaacgatag gcttgaacag   1140
ttcaaaagag aacgttatgc tggctgggag acagatttcg gaagaaagat tttgagtggt   1200
ggctactctt tgtcttccct ggccacagat gccttggaca gaggtttgaa ccccaagcac   1260
agctctggac aacaagaaag acttgaaggt gtggtaaacc aagccatcta tggtcttcgt   1320
taa                                                                 1323

<210> SEQ ID NO 14
<211> LENGTH: 440
<212> TYPE: PRT
<213> ORGANISM: Viridibacillus arvi

<400> SEQUENCE: 14

Met Ser Tyr Phe Glu His Ile Pro Thr Ile Arg Tyr Glu Gly Pro Gln
1               5                   10                  15

Ser Asp Asn Pro Leu Ala Tyr His His Tyr Asp Arg Ser Lys Arg Val
            20                  25                  30

Leu Gly Lys Thr Leu Glu Glu His Leu Arg Ile Ala Val Cys Tyr Trp
        35                  40                  45

His Thr Phe Val Trp Pro Gly Val Asp Ile Phe Gly Gln Gly Thr Phe
    50                  55                  60

Glu Arg Pro Trp Gln Gln Pro Gly Asp Ala Met Glu Arg Ala His Gln
65                  70                  75                  80

Lys Ala Asp Ala Ala Phe Glu Leu Phe Ser Lys Leu Gly Thr Pro Tyr
                85                  90                  95

Tyr Thr Phe His Asp Thr Asp Val Ala Pro Glu Gly Ser Ser Leu Lys
            100                 105                 110

Glu Tyr Ser Glu Asn Phe Ala Arg Ile Ser Asp Tyr Leu Ala Arg Lys
        115                 120                 125

Gln Gln Asp Thr Gly Val Lys Leu Leu Trp Gly Thr Ala Asn Leu Phe
    130                 135                 140

Ser His Pro Arg Tyr Ala Gly Gly Ala Ala Thr Ser Pro Asn Pro Glu
145                 150                 155                 160

Val Phe Ala Phe Ala Ala Thr Gln Val Cys His Ala Leu Asp Ala Thr
                165                 170                 175

Gln Arg Leu Gly Gly Glu Asn Tyr Val Leu Trp Gly Gly Arg Glu Gly
            180                 185                 190

Tyr Asp Thr Leu Leu Asn Thr Asp Leu Gly Arg Glu Arg Glu Gln Phe
        195                 200                 205

Ala Arg Phe Leu Asn Met Val Val Glu His Ala His Lys Ile Gly Phe
    210                 215                 220

Lys Gly Thr Leu Leu Ile Glu Pro Lys Pro Gln Glu Pro Thr Lys His
```

```
                    225                 230                 235                 240
Gln Tyr Asp Tyr Asp Val Ala Ala Val His Gly Phe Leu Thr Gln Tyr
                245                 250                 255

Gly Leu Gln Asn Asp Ile Arg Val Asn Ile Glu Ala Asn His Ala Thr
            260                 265                 270

Leu Ala Gly His Ser Phe His Glu Ile Ala Ser Ala Phe Ala Leu
            275                 280                 285

Gly Ile Phe Gly Ser Val Asp Ala Asn Arg Gly Asp Pro Gln Asn Gly
        290                 295                 300

Trp Asp Thr Asp Gln Phe Pro Asn Ser Val Glu Glu Leu Thr Leu Ala
305                 310                 315                 320

Phe Tyr Glu Ile Leu Lys His Gly Gly Phe Thr Thr Gly Gly Met Asn
                325                 330                 335

Phe Asp Ala Lys Val Arg Arg Gln Ser Val Asp Ala Glu Asp Leu Phe
            340                 345                 350

Tyr Gly His Ile Ser Ala Ile Asp Asn Leu Ala Leu Ala Val Glu Arg
        355                 360                 365

Ala Ala Val Leu Ile Glu Asn Asp Arg Leu Glu Gln Phe Lys Arg Glu
    370                 375                 380

Arg Tyr Ala Gly Trp Glu Thr Asp Phe Gly Arg Lys Ile Leu Ser Gly
385                 390                 395                 400

Gly Tyr Ser Leu Ser Ser Leu Ala Thr Asp Ala Leu Asp Arg Gly Leu
                405                 410                 415

Asn Pro Lys His Ser Ser Gly Gln Gln Glu Arg Leu Glu Gly Val Val
            420                 425                 430

Asn Gln Ala Ile Tyr Gly Leu Arg
        435                 440

<210> SEQ ID NO 15
<211> LENGTH: 1323
<212> TYPE: DNA
<213> ORGANISM: Enterobacter aerogenes

<400> SEQUENCE: 15
atgcaaacat actttgatca attagacaga gtaagatacg aaggacctaa aagtacaaac      60
ccattggcct tccgtcatta caatccagat gaattagtac taggtaagag gatggaagat     120
cacctgagat ttgctgcctg ctattggcac acttttttgct ggaatggtgc cgatatgttc    180
ggtgtgggta gttttgatag accatggcag caacctggag aggctttaga aatggctaaa    240
agaaaagctg aggttgcttt tgaattcttc cataagctta atgtaccata ctactgcttt    300
catgacgtag acgttagtcc tgagggagcc agcttgaaag aatactcaaa caactttgcc    360
caaatggttg atgtttttagt ggagaaacag caacaatcag gtgtaaagtt gttgtggggt    420
actgcaaatt gttttacaaa tccaagatac ggagcaggtg ctgccacaaa tccagatcca    480
gaagtgtttt catgggctgc aacacaggta gtaactgcaa tgaacgcaac tcacaagtta    540
ggtggtgaaa actacgttct atggggtggc cgtgaggggt acgagacctt attgaataca    600
gacttgaggc aagaaagaga gcaaatcggg aggtttatgc agctagtcgt cgagcataaa    660
cacaaaatcg gctttcaagg aactctgttg attgagccaa agccacaaga acctactaaa    720
catcagtacg attacgatgc ttctacagta tatggctttc ttaagcaatt tggtttagaa    780
aaagagatca aactaaacat tgaagcaaac cacgccacat tagctggcca ttctttccat    840
catgaaatcg caactgctat tgccttaggc ttattcggtt ctgttgatgc caatagagga    900
```

```
gatgcacaat tgggttggga cacagatcaa ttcccaaatt ctgtcgagga aaatgctctg      960
gtgatgtacg aaatcttgaa agccggtggt ttcacgactg gtggcttgaa tttcgacgca     1020
aaagtaagaa gacagagtac agacaaatac gatttgttct atggacatat cggtgccatg     1080
gataccatgg ctttgagtct taaagtcgct gctagaatga ttgaagatgg agaactagat     1140
aagagagtcg ctaaaagata tgcaggttgg aacggtgaat taggccaaca gatcttaact     1200
ggtcaaatga cattgacgga tatcgcccat tatgctacac agcataatct agctccccag     1260
catcattccg gtcaccagga actattggag aatttggtaa atcactattt gtttgataaa     1320
taa                                                                  1323

<210> SEQ ID NO 16
<211> LENGTH: 440
<212> TYPE: PRT
<213> ORGANISM: Enterobacter aerogenes

<400> SEQUENCE: 16
```

Met Gln Thr Tyr Phe Asp Gln Leu Asp Arg Val Arg Tyr Glu Gly Pro
1               5                   10                  15

Lys Ser Thr Asn Pro Leu Ala Phe Arg His Tyr Asn Pro Asp Glu Leu
            20                  25                  30

Val Leu Gly Lys Arg Met Glu Asp His Leu Arg Phe Ala Ala Cys Tyr
        35                  40                  45

Trp His Thr Phe Cys Trp Asn Gly Ala Asp Met Phe Gly Val Gly Ser
    50                  55                  60

Phe Asp Arg Pro Trp Gln Gln Pro Gly Glu Ala Leu Glu Met Ala Lys
65                  70                  75                  80

Arg Lys Ala Glu Val Ala Phe Glu Phe Phe His Lys Leu Asn Val Pro
                85                  90                  95

Tyr Tyr Cys Phe His Asp Val Asp Val Ser Pro Glu Gly Ala Ser Leu
            100                 105                 110

Lys Glu Tyr Ser Asn Asn Phe Ala Gln Met Val Asp Val Leu Val Glu
        115                 120                 125

Lys Gln Gln Gln Ser Gly Val Lys Leu Leu Trp Gly Thr Ala Asn Cys
    130                 135                 140

Phe Thr Asn Pro Arg Tyr Gly Ala Gly Ala Ala Thr Asn Pro Asp Pro
145                 150                 155                 160

Glu Val Phe Ser Trp Ala Ala Thr Gln Val Val Thr Ala Met Asn Ala
                165                 170                 175

Thr His Lys Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
        195                 200                 205

Ile Gly Arg Phe Met Gln Leu Val Val Glu His Lys His Lys Ile Gly
    210                 215                 220

Phe Gln Gly Thr Leu Leu Ile Glu Pro Lys Pro Gln Glu Pro Thr Lys
225                 230                 235                 240

His Gln Tyr Asp Tyr Asp Ala Ser Thr Val Tyr Gly Phe Leu Lys Gln
                245                 250                 255

Phe Gly Leu Glu Lys Glu Ile Lys Leu Asn Ile Glu Ala Asn His Ala
            260                 265                 270

Thr Leu Ala Gly His Ser Phe His His Glu Ile Ala Thr Ala Ile Ala
        275                 280                 285

Leu Gly Leu Phe Gly Ser Val Asp Ala Asn Arg Gly Asp Ala Gln Leu

```
                290                 295                 300
Gly Trp Asp Thr Asp Gln Phe Pro Asn Ser Val Glu Glu Asn Ala Leu
305                 310                 315                 320

Val Met Tyr Glu Ile Leu Lys Ala Gly Gly Phe Thr Thr Gly Gly Leu
                325                 330                 335

Asn Phe Asp Ala Lys Val Arg Arg Gln Ser Thr Asp Lys Tyr Asp Leu
                340                 345                 350

Phe Tyr Gly His Ile Gly Ala Met Asp Thr Met Ala Leu Ser Leu Lys
                355                 360                 365

Val Ala Ala Arg Met Ile Glu Asp Gly Glu Leu Asp Lys Arg Val Ala
                370                 375                 380

Lys Arg Tyr Ala Gly Trp Asn Gly Glu Leu Gly Gln Gln Ile Leu Thr
385                 390                 395                 400

Gly Gln Met Thr Leu Thr Asp Ile Ala His Tyr Ala Thr Gln His Asn
                405                 410                 415

Leu Ala Pro Gln His His Ser Gly His Gln Glu Leu Leu Glu Asn Leu
                420                 425                 430

Val Asn His Tyr Leu Phe Asp Lys
                435                 440

<210> SEQ ID NO 17
<211> LENGTH: 1323
<212> TYPE: DNA
<213> ORGANISM: Burkholderia sediminicola

<400> SEQUENCE: 17
atgtcctatt tcgaacacat tcccgagatt agatatgaag gtccacaatc cgacaaccct        60
cttgcctaca gacattacga caaatccaaa agagtcctag gtaagacttt ggaagaacac       120
ctgagaattg ctgtctgtta ctggcatacc tttgtatggc caggagtaga catctttggt       180
cagggaactt tcaggagacc ctggcagcaa gcaggtgacg caatggaaag agcccagcag       240
aaagcagact ctgcttttga gttctttttct aagttaggca ccccatacta caccttccac      300
gacacagacg tcgctccgga aggtgactct ttgaaagcat attcagagaa tttcactaga       360
attgccgact acttagctag aaaacagcag gacacaggcg tcaaattgtt gtggggcacc       420
gccaacttgt tttcacatcc aagatacgct gccggtgccg caacaagccc agatcccgag       480
atctttgctt ttgctgcaac ccaagttaga catgccttag atgccactca atgctagga       540 ggtgagaatt acgtcttatg gggtggtagg aaggttacg atacactatt gaatacggat       600
ctggtgagag aacgtgacca gttggcaaga tttctgcata tggtagtcga acacaaacat       660
aaggttggct caaaggagc attgttgatc gaacctaagc ctcaagaacc cacaaaacat       720
caatttgact acgatgtcgc tacggttcat ggcttcttat tgcagtatgg tctagaaaaa       780
gagattagag tcaacattga ggcaaaccac gctactcttg caggccactc atttcatcat       840
gaaattgcta ctgcctacgc actaggcata ttcggaagtg ttgatgcaaa cagaggtgat       900
caacaaaacg gatgggatac agatcagttt ccgaactcag ttgaagaatt gacattagcc       960
ttctatgaaa tactaaagca tggaggtttc accacaggcg gtatgaactt tgatgcaaaa      1020
gtgcgtagac agtcagttga cgcagaagat tgttctttg ccatattgg tgctattgat       1080 aacttggcct tggcagttga aagagctgcc acattgatcg aaaatgatag attggaagcc      1140
ttcaaacgtc aaagatacgc tggctgggaa tccgaatttg gtcacaaaat cctaaaagga      1200
gactatagtt tgtccacttt agctgccgac gctcttacta ggggactgaa cccacaacat      1260
```

-continued gcatctggta gacaggaaca actggaaaac gtggtcaatc aagcaatcta ttctagaagg    1320
taa                                                                  1323

<210> SEQ ID NO 18
<211> LENGTH: 440
<212> TYPE: PRT
<213> ORGANISM: Burkholderia sediminicola

<400> SEQUENCE: 18

Met Ser Tyr Phe Glu His Ile Pro Glu Ile Arg Tyr Glu Gly Pro Gln
1               5                   10                  15

Ser Asp Asn Pro Leu Ala Tyr Arg His Tyr Asp Lys Ser Lys Arg Val
            20                  25                  30

Leu Gly Lys Thr Leu Glu Glu His Leu Arg Ile Ala Val Cys Tyr Trp
        35                  40                  45

His Thr Phe Val Trp Pro Gly Val Asp Ile Phe Gly Gln Gly Thr Phe
    50                  55                  60

Arg Arg Pro Trp Gln Gln Ala Gly Asp Ala Met Glu Arg Ala Gln Gln
65                  70                  75                  80

Lys Ala Asp Ser Ala Phe Glu Phe Phe Ser Lys Leu Gly Thr Pro Tyr
                85                  90                  95

Tyr Thr Phe His Asp Thr Asp Val Ala Pro Glu Gly Asp Ser Leu Lys
            100                 105                 110

Ala Tyr Ser Glu Asn Phe Thr Arg Ile Ala Asp Tyr Leu Ala Arg Lys
        115                 120                 125

Gln Gln Asp Thr Gly Val Lys Leu Leu Trp Gly Thr Ala Asn Leu Phe
    130                 135                 140

Ser His Pro Arg Tyr Ala Ala Gly Ala Ala Thr Ser Pro Asp Pro Glu
145                 150                 155                 160

Ile Phe Ala Phe Ala Ala Thr Gln Val Arg His Ala Leu Asp Ala Thr
                165                 170                 175

Gln Met Leu Gly Gly Glu Asn Tyr Val Leu Trp Gly Gly Arg Glu Gly
            180                 185                 190

Tyr Asp Thr Leu Leu Asn Thr Asp Leu Val Arg Glu Arg Asp Gln Leu
        195                 200                 205

Ala Arg Phe Leu His Met Val Val Glu His Lys His Lys Val Gly Phe
    210                 215                 220

Lys Gly Ala Leu Leu Ile Glu Pro Lys Pro Gln Glu Pro Thr Lys His
225                 230                 235                 240

Gln Phe Asp Tyr Asp Val Ala Thr Val His Gly Phe Leu Leu Gln Tyr
                245                 250                 255

Gly Leu Glu Lys Glu Ile Arg Val Asn Ile Glu Ala Asn His Ala Thr
            260                 265                 270

Leu Ala Gly His Ser Phe His His Glu Ile Ala Thr Ala Tyr Ala Leu
        275                 280                 285

Gly Ile Phe Gly Ser Val Asp Ala Asn Arg Gly Asp Gln Gln Asn Gly
    290                 295                 300

Trp Asp Thr Asp Gln Phe Pro Asn Ser Val Glu Glu Leu Thr Leu Ala
305                 310                 315                 320

Phe Tyr Glu Ile Leu Lys His Gly Gly Phe Thr Thr Gly Gly Met Asn
                325                 330                 335

Phe Asp Ala Lys Val Arg Arg Gln Ser Val Asp Ala Glu Asp Leu Phe
            340                 345                 350

Phe Gly His Ile Gly Ala Ile Asp Asn Leu Ala Leu Ala Val Glu Arg

Ala Ala Thr Leu Ile Glu Asn Asp Arg Leu Glu Ala Phe Lys Arg Gln
                370                 375                 380

Arg Tyr Ala Gly Trp Glu Ser Glu Phe Gly His Lys Ile Leu Lys Gly
385                 390                 395                 400

Asp Tyr Ser Leu Ser Thr Leu Ala Ala Asp Ala Leu Thr Arg Gly Leu
                405                 410                 415

Asn Pro Gln His Ala Ser Gly Arg Gln Glu Gln Leu Glu Asn Val Val
            420                 425                 430

Asn Gln Ala Ile Tyr Ser Arg Arg
        435                 440

<210> SEQ ID NO 19
<211> LENGTH: 1323
<212> TYPE: DNA
<213> ORGANISM: Trichoderma koningiopsis

<400> SEQUENCE: 19

| | | |
|---|---|---|
| atgtcctatt tcgaacacat tcccgagatt agatatgaag gtccacaatc cgacaaccct | 60 |
| cttgcctaca gacattacga caaaaacaga agagtcctag gtaagacttt ggaagaacac | 120 |
| ctgagattag ctgtctgtta ctggcatacc tttgtatggc caggagtaga catctttggt | 180 |
| caggggactt tcaggagacc ctggcagcaa gcaggtgacg caatggaaag agcccagcag | 240 |
| aaagcagacg ctgcttttga gttctttggt aagttaggca ccccatacta caccttccac | 300 |
| gacacagacg tcgctccgga aggtaccaat ttgaaagagt attcagagaa tttcactaga | 360 |
| attgccgact acttagctag aaaacagcag gacacaggca tcaaattgtt gtggggcacc | 420 |
| gccaacttgt tttcacatcc aagatacgct gccggtgccg caacaagccc agatcccgaa | 480 |
| gtatttgctt tgctgcaac ccaagttaga catgccttag atgccactga agactagga | 540 |
| ggtgagaatt acgtcttatg gggtggtagg gaaggttacg atacactatt gaatacggat | 600 |
| ctggtgagag aacgtgacca gttggcaaga tttctgcata tggtagtcga tcacgctcat | 660 |
| aagattggct tcaaaggagc attgttgatc gaacctaagc ctcaagaacc cacaaaacat | 720 |
| caatatgact acgatgtcgc tagcgttcat ggcttcttat tgcagtatgg tctagaaaaa | 780 |
| gagatttgtg tcaacattga ggcaaaccac gctactcttg caggccactc atttcatcat | 840 |
| gaaattgcta ctgcctacgc actaggcata ttcggaagtg ttgatgcaaa cagaggtgat | 900 |
| ccacaaaacg gatgggatac agatcagttt ccgaactcag ttgaagaatt gacattagcc | 960 |
| ttctatgaaa tactaaagca tggaggtttc accacaggcg gtatgaactt tgatagtaaa | 1020 |
| gtgcgtagac agtcagttga ccctgaagat ttgttccatg gccatattgg tgctattgat | 1080 |
| aacttggcct tggcagttga agagctgcc gtattgatcg aaaatgatag attggaacag | 1140 |
| ttcaaacgtc aaagatactc tggctgggat gcagaattag gtaggaaaat cctagcagga | 1200 |
| gactatagtt tgtccacttt agctgccgac gctatgacta ggggagtgaa cccacaacat | 1260 |
| gcatctggtc aacaggaaag aatggaaaac atcgtcaatc aagcaatcta ttctggaagg | 1320 |
| taa | 1323 |

<210> SEQ ID NO 20
<211> LENGTH: 440
<212> TYPE: PRT
<213> ORGANISM: Trichoderma koningiopsis

<400> SEQUENCE: 20

-continued

```
Met Ser Tyr Phe Glu His Ile Pro Glu Ile Arg Tyr Glu Gly Pro Gln
1               5                   10                  15

Ser Asp Asn Pro Leu Ala Tyr Arg His Tyr Asp Lys Asn Arg Arg Val
            20                  25                  30

Leu Gly Lys Thr Leu Glu Glu His Leu Arg Leu Ala Val Cys Tyr Trp
        35                  40                  45

His Thr Phe Val Trp Pro Gly Val Asp Ile Phe Gly Gln Gly Thr Phe
50                  55                  60

Arg Arg Pro Trp Gln Gln Ala Gly Asp Ala Met Glu Arg Ala Gln Gln
65                  70                  75                  80

Lys Ala Asp Ala Ala Phe Glu Phe Phe Gly Lys Leu Gly Thr Pro Tyr
                85                  90                  95

Tyr Thr Phe His Asp Thr Asp Val Ala Pro Glu Gly Thr Asn Leu Lys
            100                 105                 110

Glu Tyr Ser Glu Asn Phe Thr Arg Ile Ala Asp Tyr Leu Ala Arg Lys
            115                 120                 125

Gln Gln Asp Thr Gly Ile Lys Leu Leu Trp Gly Thr Ala Asn Leu Phe
    130                 135                 140

Ser His Pro Arg Tyr Ala Ala Gly Ala Ala Thr Ser Pro Asp Pro Glu
145                 150                 155                 160

Val Phe Ala Phe Ala Ala Thr Gln Val Arg His Ala Leu Asp Ala Thr
                165                 170                 175

Glu Arg Leu Gly Gly Glu Asn Tyr Val Leu Trp Gly Gly Arg Glu Gly
            180                 185                 190

Tyr Asp Thr Leu Leu Asn Thr Asp Leu Val Arg Glu Arg Asp Gln Leu
            195                 200                 205

Ala Arg Phe Leu His Met Val Val Asp His Ala His Lys Ile Gly Phe
    210                 215                 220

Lys Gly Ala Leu Leu Ile Glu Pro Lys Pro Gln Glu Pro Thr Lys His
225                 230                 235                 240

Gln Tyr Asp Tyr Asp Val Ala Ser Val His Gly Phe Leu Leu Gln Tyr
                245                 250                 255

Gly Leu Glu Lys Glu Ile Cys Val Asn Ile Glu Ala Asn His Ala Thr
            260                 265                 270

Leu Ala Gly His Ser Phe His His Glu Ile Ala Thr Ala Tyr Ala Leu
            275                 280                 285

Gly Ile Phe Gly Ser Val Asp Ala Asn Arg Gly Asp Pro Gln Asn Gly
    290                 295                 300

Trp Asp Thr Asp Gln Phe Pro Asn Ser Val Glu Glu Leu Thr Leu Ala
305                 310                 315                 320

Phe Tyr Glu Ile Leu Lys His Gly Gly Phe Thr Thr Gly Gly Met Asn
                325                 330                 335

Phe Asp Ser Lys Val Arg Arg Gln Ser Val Asp Pro Glu Asp Leu Phe
            340                 345                 350

His Gly His Ile Gly Ala Ile Asp Asn Leu Ala Leu Ala Val Glu Arg
            355                 360                 365

Ala Ala Val Leu Ile Glu Asn Asp Arg Leu Glu Gln Phe Lys Arg Gln
    370                 375                 380

Arg Tyr Ser Gly Trp Asp Ala Glu Leu Gly Arg Lys Ile Leu Ala Gly
385                 390                 395                 400

Asp Tyr Ser Leu Ser Thr Leu Ala Ala Asp Ala Met Thr Arg Gly Val
                405                 410                 415

Asn Pro Gln His Ala Ser Gly Gln Gln Glu Arg Met Glu Asn Ile Val
```

```
                    420                 425                 430
Asn Gln Ala Ile Tyr Ser Gly Arg
        435                 440

<210> SEQ ID NO 21
<211> LENGTH: 1311
<212> TYPE: DNA
<213> ORGANISM: Unknown
<220> FEATURE:
<223> OTHER INFORMATION: Artificial DNA Sequence

<400> SEQUENCE: 21
atgaaggaat actttcctca gataggtaag atacaattcg aaggcaaaga ttccaagaat      60
ccaatggctt ttcattacta tgatgccgaa aaggtcataa tgggtaagcc tatgaaggag     120
tggctgaggt ttgctatggc ttggtggcat acattatgtg ccgagggatc cgaccagttt     180
ggcccaggta ccaaaacatt cccgtggaat gagggtgccg acgctattga aaggccaag      240 aacaaagccg acgctggttt tgagattatg accaagcttg gttttcccta tttctgcttc     300
catgatgttg atttgattgc cgagggcaac acagtagaag aatacgaatc aaacttagcc     360
gcaataacgg actacttgaa agagaaaatg gatgctaccg gtatcaagtt gttatggtct     420
acagcaaatg ttttttggtaa cgctaggtat atgaatggcg catcaacgaa cccagacttt     480
gacgttgtcg ctagagcaat tgtccagatc aagaatgcta tagacgcagg catcaaattg     540
ggagccgaga actatgtctt tgggggtgga agggagggat acatgtcctt attgaataca     600
gatcagaaac gtgagaagga acacatggct acaatgctga ggatggcaag agattatgca     660
agaagtaaag gatttactgg aaccttcttg attgagccaa aacccatgga accaagtaaa     720
catcagtatg acgttgacac agagacagtc atcggcttct taagagccca tggtttggat     780
aaagacttta aggtcaacat tgaagttaac catgctacct agctggaca tacctttgag     840 catgaactag catgcgctgt ggatgctggc atgttaggtt ctattgatgc aaacaggggt     900
gactatcaaa atggctggga tacagatcag tttcctatcg atcaattcga tcttgttcag     960
gcctggatgg agatcttaag aggaggggt ttgggaacag gtgggaccaa tttcgacgct    1020
aaaactagaa gaaattctac cgacttggaa gacatcttct tagcacacat atccggtatg    1080
gatgccatgg ctcgtgccct ggaatctgcc gcaaagcttc tggaggaatc ccccatcaaa    1140
cagatgaaag cagaccgtta tgcttcattt gatagcggtt taggcaaaaa gtttgaaaat    1200
ggagaaatga ctttagaaga agcctatgag tatggtaaac aagtcggcga acctaaacag    1260
acatccggca agcaagagtt gtatgaagct atcgtagcaa tgtattgtta a             1311

<210> SEQ ID NO 22
<211> LENGTH: 436
<212> TYPE: PRT
<213> ORGANISM: Unknown
<220> FEATURE:
<223> OTHER INFORMATION: Artificial DNA Sequence

<400> SEQUENCE: 22

Met Lys Glu Tyr Phe Pro Gln Ile Gly Lys Ile Gln Phe Glu Gly Lys
1               5                   10                  15

Asp Ser Lys Asn Pro Met Ala Phe His Tyr Tyr Asp Ala Glu Lys Val
            20                  25                  30

Ile Met Gly Lys Pro Met Lys Glu Trp Leu Arg Phe Ala Met Ala Trp
        35                  40                  45

Trp His Thr Leu Cys Ala Glu Gly Ser Asp Gln Phe Gly Pro Gly Thr
```

```
                50                  55                  60
Lys Thr Phe Pro Trp Asn Glu Gly Ala Asp Ala Ile Glu Lys Ala Lys
 65                  70                  75                  80

Asn Lys Ala Asp Ala Gly Phe Glu Ile Met Thr Lys Leu Gly Phe Pro
                 85                  90                  95

Tyr Phe Cys Phe His Asp Val Asp Leu Ile Ala Glu Gly Asn Thr Val
            100                 105                 110

Glu Glu Tyr Glu Ser Asn Leu Ala Ala Ile Thr Asp Tyr Leu Lys Glu
            115                 120                 125

Lys Met Asp Ala Thr Gly Ile Lys Leu Leu Trp Ser Thr Ala Asn Val
130                 135                 140

Phe Gly Asn Ala Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
            180                 185                 190

Gly Tyr Met Ser Leu Leu Asn Thr Asp Gln Lys Arg Glu Lys Glu His
            195                 200                 205

Met Ala Thr Met Leu Arg Met Ala Arg Asp Tyr Ala Arg Ser Lys Gly
210                 215                 220

Phe Thr Gly Thr Phe Leu Ile Glu Pro Lys Pro Met Glu Pro Ser Lys
225                 230                 235                 240

His Gln Tyr Asp Val Asp Thr Glu Thr Val Ile Gly Phe Leu Arg Ala
                245                 250                 255

His Gly Leu Asp Lys Asp Phe Lys Val Asn Ile Glu Val Asn His Ala
            260                 265                 270

Thr Leu Ala Gly His Thr Phe Glu His Glu Leu Ala Cys Ala Val Asp
            275                 280                 285

Ala Gly Met Leu Gly Ser Ile Asp Ala Asn Arg Gly Asp Tyr Gln Asn
            290                 295                 300

Gly Trp Asp Thr Asp Gln Phe Pro Ile Asp Gln Phe Asp Leu Val Gln
305                 310                 315                 320

Ala Trp Met Glu Ile Leu Arg Gly Gly Leu Gly Thr Gly Gly Thr
                325                 330                 335

Asn Phe Asp Ala Lys Thr Arg Arg Asn Ser Thr Asp Leu Glu Asp Ile
            340                 345                 350

Phe Leu Ala His Ile Ser Gly Met Asp Ala Met Ala Arg Ala Leu Glu
            355                 360                 365

Ser Ala Ala Lys Leu Leu Glu Glu Ser Pro Ile Lys Gln Met Lys Ala
370                 375                 380

Asp Arg Tyr Ala Ser Phe Asp Ser Gly Leu Gly Lys Lys Phe Glu Asn
385                 390                 395                 400

Gly Glu Met Thr Leu Glu Glu Ala Tyr Glu Tyr Gly Lys Gln Val Gly
                405                 410                 415

Glu Pro Lys Gln Thr Ser Gly Lys Gln Glu Leu Tyr Glu Ala Ile Val
            420                 425                 430

Ala Met Tyr Cys
            435

<210> SEQ ID NO 23
<211> LENGTH: 1308
<212> TYPE: DNA
<213> ORGANISM: Unknown
```

<220> FEATURE:
<223> OTHER INFORMATION: Artificial DNA Sequence

<400> SEQUENCE: 23

```
atggcttact tcacagacat tcccaagatt acttatcaag gtccaaagag caaagatcca    60
ttgtccttca aacactacaa tccagacgaa gttatagaag caaaacgat gagggaacat    120
ttacgttttg gtgctgctta ttggcacgta atgagaaatg cattaggtga tccttttgga   180
ggaggaaccg cattgatgcc atgggacgac ggaacggatt ctgtcaacaa tgcaaagaaa   240
agggcagacg ttttcttcga gttcttagag aagatcgata ttgacttcta ttgcttccac   300
gaccgtgatg ttgcacctga gttgggcgat ttcaagaaaa gcagcgatgc attacgtcaa   360
gttacagctc atttgggtga attgcagaaa gcttctggta agaagctact atggggtaca   420
gcttgcctgt tctcacatcc cagatactct cagggtgccg aaccagccc agatttacgt    480
gttttcacat atgccgctgc ccaagttaaa gaagccatgg atagtactca tgctttagga   540
ggcttgggtt atacttttg gggaggtaga aaaggttatg cttccttgtt aaacacggac    600
atgaaaagag aattagatca cttagcagca ttgctacata tggcagtagc ttacaaaaag   660
gaaattggct ttggtggtca gttttacata gaacctaaac caagggagcc gagcacccac   720
caatatgact cagatagcgc tgcatgcttg aatttcttgc gtgagtacgg tttgctagaa   780
cacttcaagt tgaatcttga aaccaaccat gcaaccttag ccggacatac catggagcat   840
gaaatgaccg ttgcaattgg tgccgatgcc ttaggttctg tagatgcaaa ccaaggcgat   900
accttattgg ttgggatac agatcaattc cctacagaca tttacgggac ggccaaaatc    960
atgttgaaag tcttggaaat gggtggattt actactggcg gattgaattt cgatgctaaa  1020
agacgtagag aatcacatga acctattgac ttattccatg ctcatatcgg aggtatggat  1080
gcctttgcta gagggctgaa gatagctgcc gctgttcgtg cagatggccg tattggcgac  1140
tttgtaaagg caagatattc atcatgggac agtgatcttg gtgccaagat agaatcagga  1200
aaagccacac ttgctgaact agctgaattg gccagtactg gaggtgaacc acaattggca  1260
tctggaagac aagaattgat ggagaacatc ttgaatgaat tgatataa               1308
```

<210> SEQ ID NO 24
<211> LENGTH: 435
<212> TYPE: PRT
<213> ORGANISM: Unknown
<220> FEATURE:
<223> OTHER INFORMATION: Artificial DNA Sequence

<400> SEQUENCE: 24

```
Met Ala Tyr Phe Thr Asp Ile Pro Lys Ile Thr Tyr Gln Gly Pro Lys
1               5                   10                  15

Ser Lys Asp Pro Leu Ser Phe Lys His Tyr Asn Pro Asp Glu Val Ile
            20                  25                  30

Glu Gly Lys Thr Met Arg Glu His Leu Arg Phe Gly Ala Ala Tyr Trp
        35                  40                  45

His Val Met Arg Asn Ala Leu Gly Asp Pro Phe Gly Gly Gly Thr Ala
    50                  55                  60

Leu Met Pro Trp Asp Asp Gly Thr Asp Ser Val Asn Asn Ala Lys Lys
65                  70                  75                  80

Arg Ala Asp Val Phe Phe Glu Phe Leu Glu Lys Ile Asp Ile Asp Phe
                85                  90                  95

Tyr Cys Phe His Asp Arg Asp Val Ala Pro Glu Leu Gly Asp Phe Lys
            100                 105                 110
```

```
Lys Ser Ser Asp Ala Leu Arg Gln Val Thr Ala His Leu Gly Glu Leu
        115                 120                 125

Gln Lys Ala Ser Gly Lys Lys Leu Leu Trp Gly Thr Ala Cys Leu Phe
130                 135                 140

Ser His Pro Arg Tyr Ser Gln Gly Ala Gly Thr Ser Pro Asp Leu Arg
145                 150                 155                 160

Val Phe Thr Tyr Ala Ala Ala Gln Val Lys Glu Ala Met Asp Ser Thr
                165                 170                 175

His Ala Leu Gly Gly Leu Gly Tyr Thr Phe Trp Gly Arg Glu Gly
        180                 185                 190

Tyr Ala Ser Leu Leu Asn Thr Asp Met Lys Arg Glu Leu Asp His Leu
        195                 200                 205

Ala Ala Leu Leu His Met Ala Val Ala Tyr Lys Lys Glu Ile Gly Phe
210                 215                 220

Gly Gly Gln Phe Tyr Ile Glu Pro Lys Pro Arg Glu Pro Ser Thr His
225                 230                 235                 240

Gln Tyr Asp Ser Asp Ser Ala Ala Cys Leu Asn Phe Leu Arg Glu Tyr
                245                 250                 255

Gly Leu Leu Glu His Phe Lys Leu Asn Leu Glu Thr Asn His Ala Thr
        260                 265                 270

Leu Ala Gly His Thr Met Glu His Glu Met Thr Val Ala Ile Gly Ala
        275                 280                 285

Asp Ala Leu Gly Ser Val Asp Ala Asn Gln Gly Asp Thr Leu Leu Gly
290                 295                 300

Trp Asp Thr Asp Gln Phe Pro Thr Asp Ile Tyr Gly Thr Ala Lys Ile
305                 310                 315                 320

Met Leu Lys Val Leu Glu Met Gly Gly Phe Thr Thr Gly Gly Leu Asn
                325                 330                 335

Phe Asp Ala Lys Arg Arg Arg Glu Ser His Glu Pro Ile Asp Leu Phe
        340                 345                 350

His Ala His Ile Gly Gly Met Asp Ala Phe Ala Arg Gly Leu Lys Ile
        355                 360                 365

Ala Ala Ala Val Arg Ala Asp Gly Arg Ile Gly Asp Phe Val Lys Ala
370                 375                 380

Arg Tyr Ser Ser Trp Asp Ser Asp Leu Gly Ala Lys Ile Glu Ser Gly
385                 390                 395                 400

Lys Ala Thr Leu Ala Glu Leu Ala Glu Leu Ala Ser Thr Gly Gly Glu
                405                 410                 415

Pro Gln Leu Ala Ser Gly Arg Gln Glu Leu Met Glu Asn Ile Leu Asn
        420                 425                 430

Glu Leu Ile
        435

<210> SEQ ID NO 25
<211> LENGTH: 591
<212> TYPE: PRT
<213> ORGANISM: Saccharomyces cerevisiae

<400> SEQUENCE: 25

Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
                20                  25                  30

Leu Lys Cys Leu Ala Ile Asn Gln Asp Leu Lys Ile Val His Ser Glu
```

```
            35                  40                  45
Thr Val Glu Phe Glu Lys Asp Leu Pro His Tyr His Thr Lys Lys Gly
 50                  55                  60

Val Tyr Ile His Gly Asp Thr Ile Glu Cys Pro Val Ala Met Trp Leu
 65                  70                  75                  80

Gly Ala Leu Asp Leu Val Leu Ser Lys Tyr Arg Glu Ala Lys Phe Pro
                 85                  90                  95

Leu Asn Lys Val Met Ala Val Ser Gly Ser Cys Gln Gln His Gly Ser
                100                 105                 110

Val Tyr Trp Ser Ser Gln Ala Glu Ser Leu Leu Glu Gln Leu Asn Lys
            115                 120                 125

Lys Pro Glu Lys Asp Leu Leu His Tyr Val Ser Ser Val Ala Phe Ala
130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Glu Lys Met Ala Gln Leu
                165                 170                 175

Thr Gly Ser Arg Ala His Phe Arg Phe Thr Gly Pro Gln Ile Leu Lys
                180                 185                 190

Ile Ala Gln Leu Glu Pro Glu Ala Tyr Glu Lys Thr Lys Thr Ile Ser
            195                 200                 205

Leu Val Ser Asn Phe Leu Thr Ser Ile Leu Val Gly His Leu Val Glu
210                 215                 220

Leu Glu Glu Ala Asp Ala Cys Gly Met Asn Leu Tyr Asp Ile Arg Glu
225                 230                 235                 240

Arg Lys Phe Met Tyr Glu Leu Leu His Leu Ile Asp Ser Ser Ser Lys
                245                 250                 255

Asp Lys Thr Ile Arg Gln Lys Leu Met Arg Ala Pro Met Lys Asn Leu
                260                 265                 270

Ile Ala Gly Thr Ile Cys Lys Tyr Phe Ile Glu Lys Tyr Gly Phe Asn
            275                 280                 285

Thr Asn Cys Lys Val Ser Pro Met Thr Gly Asp Asn Leu Ala Thr Ile
290                 295                 300

Cys Ser Leu Pro Leu Arg Lys Asn Asp Val Leu Val Ser Leu Gly Thr
305                 310                 315                 320

Ser Thr Thr Val Leu Leu Val Thr Asp Lys Tyr His Pro Ser Pro Asn
                325                 330                 335

Tyr His Leu Phe Ile His Pro Thr Leu Pro Asn His Tyr Met Gly Met
                340                 345                 350

Ile Cys Tyr Cys Asn Gly Ser Leu Ala Arg Glu Arg Ile Arg Asp Glu
            355                 360                 365

Leu Asn Lys Glu Arg Glu Asn Tyr Glu Lys Thr Asn Asp Trp Thr
370                 375                 380

Leu Phe Asn Gln Ala Val Leu Asp Asp Ser Glu Ser Ser Glu Asn Glu
385                 390                 395                 400

Leu Gly Val Tyr Phe Pro Leu Gly Glu Ile Val Pro Ser Val Lys Ala
                405                 410                 415

Ile Asn Lys Arg Val Ile Phe Asn Pro Lys Thr Gly Met Ile Glu Arg
            420                 425                 430

Glu Val Ala Lys Phe Lys Asp Lys Arg His Asp Ala Lys Asn Ile Val
            435                 440                 445

Glu Ser Gln Ala Leu Ser Cys Arg Val Arg Ile Ser Pro Leu Leu Ser
450                 455                 460
```

```
Asp Ser Asn Ala Ser Ser Gln Gln Arg Leu Asn Glu Asp Thr Ile Val
465                 470                 475                 480

Lys Phe Asp Tyr Asp Glu Ser Pro Leu Arg Asp Tyr Leu Asn Lys Arg
                485                 490                 495

Pro Glu Arg Thr Phe Phe Val Gly Gly Ala Ser Lys Asn Asp Ala Ile
            500                 505                 510

Val Lys Lys Phe Ala Gln Val Ile Gly Ala Thr Lys Gly Asn Phe Arg
            515                 520                 525

Leu Glu Thr Pro Asn Ser Cys Ala Leu Gly Gly Cys Tyr Lys Ala Met
            530                 535                 540

Trp Ser Leu Leu Tyr Asp Ser Asn Lys Ile Ala Val Pro Phe Asp Lys
545                 550                 555                 560

Phe Leu Asn Asp Asn Phe Pro Trp His Val Met Glu Ser Ile Ser Asp
                565                 570                 575

Val Asp Asn Glu Asn Trp Ile Ala Ile Ile Pro Arg Leu Ser Pro
            580                 585                 590

<210> SEQ ID NO 26
<211> LENGTH: 541
<212> TYPE: PRT
<213> ORGANISM: Saccharomyces cerevisiae

<400> SEQUENCE: 26

Met Ser Glu Phe Ala Thr Ser Gly Val Glu Ser Gly Ser Gln Gln Thr
1               5                   10                  15

Ser Ile His Ser Thr Pro Ile Val Gln Lys Leu Glu Thr Asp Glu Ser
                20                  25                  30

Pro Ile Gln Thr Lys Ser Glu Tyr Thr Asn Ala Glu Leu Pro Ala Lys
            35                  40                  45

Pro Ile Ala Ala Tyr Trp Thr Val Ile Cys Leu Cys Leu Met Ile Ala
        50                  55                  60

Phe Gly Gly Phe Val Phe Gly Trp Asp Thr Gly Thr Ile Ser Gly Phe
65                  70                  75                  80

Val Asn Gln Thr Asp Phe Lys Arg Arg Phe Gly Gln Met Lys Ser Asp
                85                  90                  95

Gly Thr Tyr Tyr Leu Ser Asp Val Arg Thr Gly Leu Ile Val Gly Ile
            100                 105                 110

Phe Asn Ile Gly Cys Ala Ile Gly Gly Leu Thr Leu Gly Arg Leu Gly
        115                 120                 125

Asp Met Tyr Gly Arg Arg Ile Gly Leu Met Cys Val Val Leu Val Tyr
    130                 135                 140

Ile Val Gly Ile Val Ile Gln Ile Ala Ser Ser Asp Lys Trp Tyr Gln
145                 150                 155                 160

Tyr Phe Ile Gly Arg Ile Ile Ser Gly Met Gly Val Gly Gly Ile Ala
                165                 170                 175

Val Leu Ser Pro Thr Leu Ile Ser Glu Thr Ala Pro Lys His Ile Arg
            180                 185                 190

Gly Thr Cys Val Ser Phe Tyr Gln Leu Met Ile Thr Leu Gly Ile Phe
        195                 200                 205

Leu Gly Tyr Cys Thr Asn Tyr Gly Thr Lys Asp Tyr Ser Asn Ser Val
    210                 215                 220

Gln Trp Arg Val Pro Leu Gly Leu Asn Phe Ala Phe Ala Ile Phe Met
225                 230                 235                 240

Ile Ala Gly Met Leu Met Val Pro Glu Ser Pro Arg Phe Leu Val Glu
```

245                 250                 255
Lys Gly Arg Tyr Glu Asp Ala Lys Arg Ser Leu Ala Lys Ser Asn Lys
            260                 265                 270

Val Thr Ile Glu Asp Pro Ser Ile Val Ala Glu Met Asp Thr Ile Met
        275                 280                 285

Ala Asn Val Glu Thr Glu Arg Leu Ala Gly Asn Ala Ser Trp Gly Glu
    290                 295                 300

Leu Phe Ser Asn Lys Gly Ala Ile Leu Pro Arg Val Ile Met Gly Ile
305                 310                 315                 320

Met Ile Gln Ser Leu Gln Gln Leu Thr Gly Asn Asn Tyr Phe Phe Tyr
                325                 330                 335

Tyr Gly Thr Thr Ile Phe Asn Ala Val Gly Met Lys Asp Ser Phe Gln
            340                 345                 350

Thr Ser Ile Val Leu Gly Ile Val Asn Phe Ala Ser Thr Phe Val Ala
        355                 360                 365

Leu Tyr Thr Val Asp Lys Phe Gly Arg Arg Lys Cys Leu Leu Gly Gly
    370                 375                 380

Ser Ala Ser Met Ala Ile Cys Phe Val Ile Phe Ser Thr Val Gly Val
385                 390                 395                 400

Thr Ser Leu Tyr Pro Asn Gly Lys Asp Gln Pro Ser Ser Lys Ala Ala
                405                 410                 415

Gly Asn Val Met Ile Val Phe Thr Cys Leu Phe Ile Phe Phe Phe Ala
            420                 425                 430

Ile Ser Trp Ala Pro Ile Ala Tyr Val Ile Val Ala Glu Ser Tyr Pro
        435                 440                 445

Leu Arg Val Lys Asn Arg Ala Met Ala Ile Ala Val Gly Ala Asn Trp
    450                 455                 460

Ile Trp Gly Phe Leu Ile Gly Phe Phe Thr Pro Phe Ile Thr Ser Ala
465                 470                 475                 480

Ile Gly Phe Ser Tyr Gly Tyr Val Phe Met Gly Cys Leu Val Phe Ser
                485                 490                 495

Phe Phe Tyr Val Phe Phe Phe Val Cys Glu Thr Lys Gly Leu Thr Leu
            500                 505                 510

Glu Glu Val Asn Glu Met Tyr Val Glu Gly Val Lys Pro Trp Lys Ser
        515                 520                 525

Gly Ser Trp Ile Ser Lys Glu Lys Arg Val Ser Glu Glu
    530                 535                 540

<210> SEQ ID NO 27
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 27
agcaacaatt ctggaagcct c                                          21

<210> SEQ ID NO 28
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 28
cagaagcacg cttatcgctc                                            20

<210> SEQ ID NO 29
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 29
aagagtggta cccatttttgt aattaaaact tagattagat tgctatg    47

<210> SEQ ID NO 30
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 30
atgggtacca ctcttgacga    20

<210> SEQ ID NO 31
<211> LENGTH: 17
<212> TYPE: DNA
<213> ORGANISM: Artificial Sequence
<220> FEATURE:
<223> OTHER INFORMATION: Artificial DNA Primer

<400> SEQUENCE: 31
gattaggggc agggcat    17

<210> SEQ ID NO 32
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 32
gccctgcccc taatcgaaag ggaaccttt acaac    35

<210> SEQ ID NO 33
<211> LENGTH: 73
<212> TYPE: DNA
<213> ORGANISM: Artificial Sequence
<220> FEATURE:
<223> OTHER INFORMATION: Artificial DNA Primer

<400> SEQUENCE: 33
tttccatcga gcataccatg gataacttcg tatagcatac attatacgaa gttatggatc    60
ccccacaagt gat    73

<210> SEQ ID NO 34
<211> LENGTH: 76
<212> TYPE: DNA
<213> ORGANISM: Artificial Sequence
<220> FEATURE:
<223> OTHER INFORMATION: Artificial DNA Primer

<400> SEQUENCE: 34
cagcgcacgc gctaggccgg ccataacttc gtatagcata cattatacga agttatgccc    60
atatttagct cgtttg    76

<210> SEQ ID NO 35

<211> LENGTH: 50
<212> TYPE: DNA
<213> ORGANISM: Artificial Sequence
<220> FEATURE:
<223> OTHER INFORMATION: Artificial DNA Primer

<400> SEQUENCE: 35
atacgaagtt atttaattaa agcttgcctt gtccccgccg ggtcacccgg         50

<210> SEQ ID NO 36
<211> LENGTH: 53
<212> TYPE: DNA
<213> ORGANISM: Artificial Sequence
<220> FEATURE:
<223> OTHER INFORMATION: Artificial DNA Primer

<400> SEQUENCE: 36
tataggtatt tgaagtcgtc atggttgttt atgttcggat gtgatgtgag aac       53

<210> SEQ ID NO 37
<211> LENGTH: 50
<212> TYPE: DNA
<213> ORGANISM: Artificial Sequence
<220> FEATURE:
<223> OTHER INFORMATION: Artificial DNA Primer

<400> SEQUENCE: 37
catccgaaca taaacaacca tgacgacttc aaatacctat aagttctatc         50

<210> SEQ ID NO 38
<211> LENGTH: 53
<212> TYPE: DNA
<213> ORGANISM: Artificial Sequence
<220> FEATURE:
<223> OTHER INFORMATION: Artificial DNA Primer

<400> SEQUENCE: 38
tcttttattt gtcagtactg attagactaa gttcagaacc gttacttttt ccc       53

<210> SEQ ID NO 39
<211> LENGTH: 51
<212> TYPE: DNA
<213> ORGANISM: Artificial Sequence
<220> FEATURE:
<223> OTHER INFORMATION: Artificial DNA Primer

<400> SEQUENCE: 39
ggttctgaac ttagtctaat cagtactgac aataaaaaga ttcttgtttt c         51

<210> SEQ ID NO 40
<211> LENGTH: 50
<212> TYPE: DNA
<213> ORGANISM: Artificial Sequence
<220> FEATURE:
<223> OTHER INFORMATION: Artificial DNA Primer

<400> SEQUENCE: 40
catccgaaca taaacaacca tgacaaaaca atacaaaaac tacgttaatg         50

<210> SEQ ID NO 41
<211> LENGTH: 50
<212> TYPE: DNA
<213> ORGANISM: Artificial Sequence
<220> FEATURE:
<223> OTHER INFORMATION: Artificial DNA Primer

<400> SEQUENCE: 41
ttttgtattg ttttgtcatg gttgtttatg ttcggatgtg atgtgagaac         50

<210> SEQ ID NO 42
<211> LENGTH: 50
<212> TYPE: DNA
<213> ORGANISM: Artificial Sequence
<220> FEATURE:
<223> OTHER INFORMATION: Artificial DNA Primer

<400> SEQUENCE: 42
gtctttgaca taaagtgatc agtactgaca ataaaaagat tcttgttttc         50

<210> SEQ ID NO 43
<211> LENGTH: 51
<212> TYPE: DNA
<213> ORGANISM: Artificial Sequence
<220> FEATURE:
<223> OTHER INFORMATION: Artificial DNA Primer

<400> SEQUENCE: 43 tcttttatt gtcagtactg atcactttat gtcaaagaca cactttttca c        51

<210> SEQ ID NO 44
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 44
gctgcggccg gcgcgccgcg atcgctcgac actggatggc ggcg              44

<210> SEQ ID NO 45
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 45
ttcgagagaa tcacggcgcg gaccttaata cattcagaca cttctg            46

<210> SEQ ID NO 46
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 46
aacacaacat ttttagttta tgtatgtgtt ttttgtagtt atag               44

<210> SEQ ID NO 47
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 47
gcctaactca ttactcgtga gtaaggaaag agtg                         34

<210> SEQ ID NO 48
<211> LENGTH: 44
<212> TYPE: DNA

<213> ORGANISM: Artificial Sequence
<220> FEATURE:
<223> OTHER INFORMATION: Artificial DNA Primer

<400> SEQUENCE: 48
attgagtcat tgttttatat ttgttgtaaa aagtagataa ttac    44

<210> SEQ ID NO 49
<211> LENGTH: 38
<212> TYPE: DNA
<213> ORGANISM: Artificial Sequence
<220> FEATURE:
<223> OTHER INFORMATION: Artificial DNA Primer

<400> SEQUENCE: 49
gttcagacat tttgaatatg tattacttgg ttatggtt    38

<210> SEQ ID NO 50
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 50
aaaaggttta aacgcttttt cagttcgagt ttatcattat c    41

<210> SEQ ID NO 51
<211> LENGTH: 37
<212> TYPE: DNA
<213> ORGANISM: Artificial Sequence
<220> FEATURE:
<223> OTHER INFORMATION: Artificial DNA Primer

<400> SEQUENCE: 51
gtttgaccat tttgtttgtt tatgtgtgtt tattcga    37

<210> SEQ ID NO 52
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 52
taaactaaaa atgttgtgtt cagtaattca gagac    35

<210> SEQ ID NO 53
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 53
atacgaagtt atggccggcc aatgctctct tatattctca ctgg    44

<210> SEQ ID NO 54
<211> LENGTH: 37
<212> TYPE: DNA
<213> ORGANISM: Artificial Sequence
<220> FEATURE:
<223> OTHER INFORMATION: Artificial DNA Primer

<400> SEQUENCE: 54
atataaaaca atgactcaat tcactgacat tgataag    37

<210> SEQ ID NO 55
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 55
catattcaaa atgtctgaac cagctcaaaa g                              31

<210> SEQ ID NO 56
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 56
gtattatatg tggtgtgggt ataacacgtg                                30

<210> SEQ ID NO 57
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 57
gctggaggcc ggcccacaaa cgttccaaag aaataaacat tgc                 43

<210> SEQ ID NO 58
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 58
catcatcaca atggctgccg gtgtcccaaa                                30

<210> SEQ ID NO 59
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 59
aacaaacaaa atggtcaaac caattatagc tcc                            33

<210> SEQ ID NO 60
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 60
tcacgagtaa tgagttaggc acttacgtat cttg                           34

<210> SEQ ID NO 61
<211> LENGTH: 38
<212> TYPE: DNA
<213> ORGANISM: Artificial Sequence
<220> FEATURE:

```
<223> OTHER INFORMATION: Artificial DNA Primer

<400> SEQUENCE: 61
cggcagccat tgtgatgatg ttttatttgt tttgattg                             38

<210> SEQ ID NO 62
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 62
cgctcgaagg ctttggcgcg gctaaatgga aaaggaaag attattg                    47

<210> SEQ ID NO 63
<211> LENGTH: 38
<212> TYPE: DNA
<213> ORGANISM: Artificial Sequence
<220> FEATURE:
<223> OTHER INFORMATION: Artificial DNA Primer

<400> SEQUENCE: 63
aaaagcgttt aaacctttc cctttatga cgtatacg                               38

<210> SEQ ID NO 64
<211> LENGTH: 37
<212> TYPE: DNA
<213> ORGANISM: Artificial Sequence
<220> FEATURE:
<223> OTHER INFORMATION: Artificial DNA Primer

<400> SEQUENCE: 64
tttgtgggcc ggcctccagc cagtaaaatc catactc                              37

<210> SEQ ID NO 65
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 65
tccatggccg cggccgcgtt taaac                                           25

<210> SEQ ID NO 66
<211> LENGTH: 23
<212> TYPE: DNA
<213> ORGANISM: Artificial Sequence
<220> FEATURE:
<223> OTHER INFORMATION: Artificial DNA Primer

<400> SEQUENCE: 66
cgccaagctg cggccggcgc gcc                                             23

<210> SEQ ID NO 67
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 67
agtacgagac gaccacgaag                                                 20
```

```
<210> SEQ ID NO 68
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 68
acccacacca catataatac atatcacata ggaagcaaca g                    41

<210> SEQ ID NO 69
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 69
acttgtttcc caattgttgc                                            20

<210> SEQ ID NO 70
<211> LENGTH: 50
<212> TYPE: DNA
<213> ORGANISM: Artificial Sequence
<220> FEATURE:
<223> OTHER INFORMATION: Artificial DNA Primer

<400> SEQUENCE: 70
ggccggccat aacttcgtat agcatacatt atacgaagtt atattaactc            50

<210> SEQ ID NO 71
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 71
gcagcttggc gtaatcatgg                                            20

<210> SEQ ID NO 72
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 72
atggaggcca attcactggc                                            20

<210> SEQ ID NO 73
<211> LENGTH: 57
<212> TYPE: DNA
<213> ORGANISM: Artificial Sequence
<220> FEATURE:
<223> OTHER INFORMATION: Artificial DNA Primer

<400> SEQUENCE: 73
gccagtgaat tggcctccat ggccgcggcc gcagtagtca acaattccca gagctac    57

<210> SEQ ID NO 74
<211> LENGTH: 57
<212> TYPE: DNA
<213> ORGANISM: Artificial Sequence
<220> FEATURE:
<223> OTHER INFORMATION: Artificial DNA Primer
```

<400> SEQUENCE: 74
ccatgattac gccaagctgc ggccggcgcg ccgcatttct ttccagactt gttcaac    57

<210> SEQ ID NO 75
<211> LENGTH: 55
<212> TYPE: DNA
<213> ORGANISM: Artificial Sequence
<220> FEATURE:
<223> OTHER INFORMATION: Artificial DNA Primer

<400> SEQUENCE: 75
ccatgattac gccaagctgc ggccggcgcg cctgttgtga gtcaatgtcg agttc    55

<210> SEQ ID NO 76
<211> LENGTH: 55
<212> TYPE: DNA
<213> ORGANISM: Artificial Sequence
<220> FEATURE:
<223> OTHER INFORMATION: Artificial DNA Primer

<400> SEQUENCE: 76
ccatgattac gccaagctgc ggccggcgcg ccgtgattct ctcgaagggt ttaac    55

<210> SEQ ID NO 77
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 77
ccatgattac gccaagctgc ggccggcgcg ccaaagcctt cgagcgtcc    49

<210> SEQ ID NO 78
<211> LENGTH: 28
<212> TYPE: DNA
<213> ORGANISM: Artificial Sequence
<220> FEATURE:
<223> OTHER INFORMATION: Artificial DNA Primer

<400> SEQUENCE: 78
gcgatcgcga attctcgaca ctggatgg    28

<210> SEQ ID NO 79
<211> LENGTH: 38
<212> TYPE: DNA
<213> ORGANISM: Artificial Sequence
<220> FEATURE:
<223> OTHER INFORMATION: Artificial DNA Primer

<400> SEQUENCE: 79
atacgaagtt atgtttaaac gatccagctt gcctcgtc    38

<210> SEQ ID NO 80
<211> LENGTH: 51
<212> TYPE: DNA
<213> ORGANISM: Artificial Sequence
<220> FEATURE:
<223> OTHER INFORMATION: Artificial DNA Primer

<400> SEQUENCE: 80
gccagtgaat tggcctccat ggccgcggcc gcacaccgtc ttccgcgtca c    51

<210> SEQ ID NO 81
<211> LENGTH: 54

```
<212> TYPE: DNA
<213> ORGANISM: Artificial Sequence
<220> FEATURE:
<223> OTHER INFORMATION: Artificial DNA Primer

<400> SEQUENCE: 81
gtttaaacat aacttcgtat aatgtatgct atacgaagtt atgcccatat ttag      54

<210> SEQ ID NO 82
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 82
ctttagccat ggttgtttat gttcggatgt g                                31

<210> SEQ ID NO 83
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 83
ataaacaacc atggctaaag aatactttcc atttac                           36

<210> SEQ ID NO 84
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 84
tcagtactga ttatttacag tgtaaggcaa caatg                            35

<210> SEQ ID NO 85
<211> LENGTH: 37
<212> TYPE: DNA
<213> ORGANISM: Artificial Sequence
<220> FEATURE:
<223> OTHER INFORMATION: Artificial DNA Primer

<400> SEQUENCE: 85
ctgtaaataa tcagtactga caataaaaag attcttg                          37

<210> SEQ ID NO 86
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 86
tgtcgagaat tcgcgatcgc gcttttggtc tgacagtaag tgtg                  44

<210> SEQ ID NO 87
<211> LENGTH: 54
<212> TYPE: DNA
<213> ORGANISM: Artificial Sequence
<220> FEATURE:
<223> OTHER INFORMATION: Artificial DNA Primer

<400> SEQUENCE: 87
```

```
ccatgattac gccaagctgc ggccggcgcg ccagggttaa tggtcttgtg gagt         54
```

<210> SEQ ID NO 88
<211> LENGTH: 57
<212> TYPE: DNA
<213> ORGANISM: Artificial Sequence
<220> FEATURE:
<223> OTHER INFORMATION: Artificial DNA Primer

<400> SEQUENCE: 88

```
gccagtgaat tggcctccat ggccgcggcc gcacaatcta tcgattgtat gggaagc     57
```

<210> SEQ ID NO 89
<211> LENGTH: 38
<212> TYPE: DNA
<213> ORGANISM: Artificial Sequence
<220> FEATURE:
<223> OTHER INFORMATION: Artificial DNA Primer

<400> SEQUENCE: 89

```
gtcttcaccg gtgcggccgc gatccagctt gcctcgtc                          38
```

<210> SEQ ID NO 90
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 90

```
ggttagaggc tagcggcgcg ccgaattctc gacactggat gg                     42
```

<210> SEQ ID NO 91
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 91

```
gtttaaacat aacttcgtat aatgtatgct atacgaagtt atgaatcag              49
```

<210> SEQ ID NO 92
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 92

```
atacgaagtt atgtttaaac cctaagaaat gaataacaat actgaca                47
```

<210> SEQ ID NO 93
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 93

```
cagttctcac atcacatccg                                              20
```

<210> SEQ ID NO 94
<211> LENGTH: 26
<212> TYPE: DNA
<213> ORGANISM: Artificial Sequence

```
<220> FEATURE:
<223> OTHER INFORMATION: Artificial DNA Primer

<400> SEQUENCE: 94
gaatcttttt attgtcagta ctgagg                                          26

<210> SEQ ID NO 95
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 95
tattctttag ccatgtcgac ttgtttatgt tcggatgtga tgtgagaac                 49

<210> SEQ ID NO 96
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 96
tattctttag ccatgtcgac cggtgcaggt tcggatgtga tgtgagaac                 49

<210> SEQ ID NO 97
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 97
tcgtcttcac cggtgcggcc gcccatgtat aatcatttgc atcc                      44

<210> SEQ ID NO 98
<211> LENGTH: 39
<212> TYPE: DNA
<213> ORGANISM: Artificial Sequence
<220> FEATURE:
<223> OTHER INFORMATION: Artificial DNA Primer

<400> SEQUENCE: 98
tcgtcttcac cggtgcggcc gctcctcgct gcagacctg                            39

<210> SEQ ID NO 99
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 99
tacactgtaa ataaggtacc tcagtactga caataaaaag attscttg                  48

<210> SEQ ID NO 100
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 100
gtcgacatgg ctaaagaata ctttccattt ac                                   32
```

<210> SEQ ID NO 101
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 101
ggtaccttat ttacagtgta aggcaacaat g         31

<210> SEQ ID NO 102
<211> LENGTH: 52
<212> TYPE: DNA
<213> ORGANISM: Artificial Sequence
<220> FEATURE:
<223> OTHER INFORMATION: Artificial DNA Primer

<400> SEQUENCE: 102
gccagtgaat tggcctccat ggccgcggcc gccggcatgc aaacatctac ac         52

<210> SEQ ID NO 103
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 103
tgctatacga agttatgttt aaaccataac gcgttacacg gaag         44

<210> SEQ ID NO 104
<211> LENGTH: 29
<212> TYPE: DNA
<213> ORGANISM: Artificial Sequence
<220> FEATURE:
<223> OTHER INFORMATION: Artificial DNA Primer

<400> SEQUENCE: 104
gcgatcgcct actatcggcg actctctcg         29

<210> SEQ ID NO 105
<211> LENGTH: 56
<212> TYPE: DNA
<213> ORGANISM: Artificial Sequence
<220> FEATURE:
<223> OTHER INFORMATION: Artificial DNA Primer

<400> SEQUENCE: 105
ccatgattac gccaagctgc ggccggcgcg ccgagcgaac gtaagagagg ttaatg         56

<210> SEQ ID NO 106
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 106
tttacaacaa atataaaaca atgaagcttc aatttttttc ctttattac         49

<210> SEQ ID NO 107
<211> LENGTH: 42
<212> TYPE: DNA
<213> ORGANISM: Artificial Sequence
<220> FEATURE:
<223> OTHER INFORMATION: Artificial DNA Primer

```
<400> SEQUENCE: 107
cgccgatagt aggcgatcgc tgtccagaaa gcagtatgtt cc                              42

<210> SEQ ID NO 108
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 108
acattatacg aagttattta attaattact cgtgagtaag gaaagagtg                       49

<210> SEQ ID NO 109
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 109
tgttttatat ttgttgtaaa aagtagataa ttac                                      34

<210> SEQ ID NO 110
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 110
ctgtcctttt accagacaac c                                                    21

<210> SEQ ID NO 111
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 111
gtacagaaga ggacgaagaa gg                                                   22

<210> SEQ ID NO 112
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 112
gttgatcagt gttcatggtc tg                                                   22

<210> SEQ ID NO 113
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 113
gcgatccgtc ctaaggcgcg ccttttagct ttgacatgat taagctc                        47

<210> SEQ ID NO 114
```

```
<211> LENGTH: 61
<212> TYPE: DNA
<213> ORGANISM: Artificial Sequence
<220> FEATURE:
<223> OTHER INFORMATION: Artificial DNA Primer

<400> SEQUENCE: 114
gattacgcca agctgcggcc gcttaattaa gtttaaactc agttcaatac aacagatcac     60
g                                                                    61

<210> SEQ ID NO 115
<211> LENGTH: 39
<212> TYPE: DNA
<213> ORGANISM: Artificial Sequence
<220> FEATURE:
<223> OTHER INFORMATION: Artificial DNA Primer

<400> SEQUENCE: 115
ttcaatagca tatctttgtt aacgaagcat ctgtgcttc                            39

<210> SEQ ID NO 116
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 116
gctaaaactc gagacgatac ctgagtattc ccacag                              36

<210> SEQ ID NO 117
<211> LENGTH: 38
<212> TYPE: DNA
<213> ORGANISM: Artificial Sequence
<220> FEATURE:
<223> OTHER INFORMATION: Artificial DNA Primer

<400> SEQUENCE: 117
gtatcgtctc gagttttagc tttgacatga ttaagctc                            38

<210> SEQ ID NO 118
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 118
gcggccgcga tgtagtttct ggttttttaaa tctcac                             36

<210> SEQ ID NO 119
<211> LENGTH: 37
<212> TYPE: DNA
<213> ORGANISM: Artificial Sequence
<220> FEATURE:
<223> OTHER INFORMATION: Artificial DNA Primer

<400> SEQUENCE: 119
agaaactaca tcgcggccgc tcctcgctgc agacctg                             37

<210> SEQ ID NO 120
<211> LENGTH: 24
<212> TYPE: DNA
<213> ORGANISM: Artificial Sequence
<220> FEATURE:
<223> OTHER INFORMATION: Artificial DNA Primer
```

```
<400> SEQUENCE: 120
agacaatgta tgtatttcgg ttcc                                              24

<210> SEQ ID NO 121
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 121
tgttgtattg aactgagttt aaaccgacag ccctccgacg g                           41

<210> SEQ ID NO 122
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 122
cgccaagctg cggccgctta attaaaaagc cttcgagcgt ccc                         43

<210> SEQ ID NO 123
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 123
atggacgaca ttgaaacagc                                                   20

<210> SEQ ID NO 124
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 124
tcatacccta gaagtattac gtgattttct g                                      31

<210> SEQ ID NO 125
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 125
attgtggcat tatagttttt tctccttgac gttaaagtat agag                        44

<210> SEQ ID NO 126
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 126
aaaaactata atgccacaat ttgatatatt atgtaaaaca cc                          42

<210> SEQ ID NO 127
```

```
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 127
aggggcctgt ttatatgcgt ctatttatgt aggatgaaag g                     41

<210> SEQ ID NO 128
<211> LENGTH: 29
<212> TYPE: DNA
<213> ORGANISM: Artificial Sequence
<220> FEATURE:
<223> OTHER INFORMATION: Artificial DNA Primer

<400> SEQUENCE: 128
acgcatataa acaggcccct tttcctttg                                    29

<210> SEQ ID NO 129
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 129
agtgtcgaga attcggcgcg cccactcaaa ggtcaatttc ttgtatg                47

<210> SEQ ID NO 130
<211> LENGTH: 26
<212> TYPE: DNA
<213> ORGANISM: Artificial Sequence
<220> FEATURE:
<223> OTHER INFORMATION: Artificial DNA Primer

<400> SEQUENCE: 130
gtttaaactg tgcttggggt ggttgg                                       26

<210> SEQ ID NO 131
<211> LENGTH: 28
<212> TYPE: DNA
<213> ORGANISM: Artificial Sequence
<220> FEATURE:
<223> OTHER INFORMATION: Artificial DNA Primer

<400> SEQUENCE: 131
ggatccatag tatttagacg gcctgcag                                     28

<210> SEQ ID NO 132
<211> LENGTH: 51
<212> TYPE: DNA
<213> ORGANISM: Artificial Sequence
<220> FEATURE:
<223> OTHER INFORMATION: Artificial DNA Primer

<400> SEQUENCE: 132
agtgtcgaga attcggcgcg ccgtacttat tcccttcgag ataatatcta g           51

<210> SEQ ID NO 133
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 133
```
gtttaaactt ttagtttatg tatgtgattt ttgtagttat ag                42

<210> SEQ ID NO 134
<211> LENGTH: 54
<212> TYPE: DNA
<213> ORGANISM: Artificial Sequence
<220> FEATURE:
<223> OTHER INFORMATION: Artificial DNA Primer

<400> SEQUENCE: 134
ggatccgatt aatataatta tataaatata ttatcttctt ttcttaatat ctag   54

<210> SEQ ID NO 135
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 135
accccaagca cagtttaaac atggtcagta agggtgaaga ag                42

<210> SEQ ID NO 136
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 136
taattatatt aatcggatcc ttatttgtac aattcatcca taccac           46

<210> SEQ ID NO 137
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 137
gaccttgtct gaggcgcgcc gaattctcga cactggatgg                  40

<210> SEQ ID NO 138
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 138
aaggatcttc ttgaggacct tgtcgagctc cgcacggcgc gcactgcac         49

<210> SEQ ID NO 139
<211> LENGTH: 57
<212> TYPE: DNA
<213> ORGANISM: Artificial Sequence
<220> FEATURE:
<223> OTHER INFORMATION: Artificial DNA Primer

<400> SEQUENCE: 139
aaggatcttc ttgaggacct tgtcgagctc tgagtaaccc atatagagtt cgtacac 57

<210> SEQ ID NO 140
<211> LENGTH: 50
<212> TYPE: DNA

<213> ORGANISM: Artificial Sequence
<220> FEATURE:
<223> OTHER INFORMATION: Artificial DNA Primer

<400> SEQUENCE: 140
ggcgcgcctc agacaaggtc ctcaagaaga tcctttgatc ttttctacgg         50

<210> SEQ ID NO 141
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 141
cctatactcg actagcggcc ctagctggcc agggcccgat acg                43

<210> SEQ ID NO 142
<211> LENGTH: 60
<212> TYPE: DNA
<213> ORGANISM: Artificial Sequence
<220> FEATURE:
<223> OTHER INFORMATION: Artificial DNA Primer

<400> SEQUENCE: 142
ccgttttgtt aggtgctgtg ggtggtccta aatggggtac ggtttcaggg tccataaagc   60

<210> SEQ ID NO 143
<211> LENGTH: 28
<212> TYPE: DNA
<213> ORGANISM: Artificial Sequence
<220> FEATURE:
<223> OTHER INFORMATION: Artificial DNA Primer

<400> SEQUENCE: 143
gaccttgtct ttggagttca atgcgtcc                                 28

<210> SEQ ID NO 144
<211> LENGTH: 60
<212> TYPE: DNA
<213> ORGANISM: Artificial Sequence
<220> FEATURE:
<223> OTHER INFORMATION: Artificial DNA Primer

<400> SEQUENCE: 144
atatactaca actgtgggaa tactcaggta tcgtctcgag ggtttcaggg tccataaagc   60

<210> SEQ ID NO 145
<211> LENGTH: 67
<212> TYPE: DNA
<213> ORGANISM: Artificial Sequence
<220> FEATURE:
<223> OTHER INFORMATION: Artificial DNA Primer

<400> SEQUENCE: 145
atactaacgc cgccatccag tgtcgagaat tcggcgcgcc tgagtaaccc atatagagtt   60
cgtacac                                                        67

<210> SEQ ID NO 146
<211> LENGTH: 70
<212> TYPE: DNA
<213> ORGANISM: Artificial Sequence
<220> FEATURE:
<223> OTHER INFORMATION: Artificial DNA Primer

<400> SEQUENCE: 146

```
gactgtaaag atggacgcat tgaactccaa agacaaggtc gtacttattc ccttcgagat    60
aatatctagg                                                          70

<210> SEQ ID NO 147
<211> LENGTH: 57
<212> TYPE: DNA
<213> ORGANISM: Artificial Sequence
<220> FEATURE:
<223> OTHER INFORMATION: Artificial DNA Primer

<400> SEQUENCE: 147
atactaacgc cgccatccag tgtcgagaat tcggcgcgcc cgcacggcgc gcactgc      57

<210> SEQ ID NO 148
<211> LENGTH: 65
<212> TYPE: DNA
<213> ORGANISM: Artificial Sequence
<220> FEATURE:
<223> OTHER INFORMATION: Artificial DNA Primer

<400> SEQUENCE: 148
gactgtaaag atggacgcat tgaactccaa agacaaggtc cactcaaagg tcaatttctt    60
gtatg                                                               65

<210> SEQ ID NO 149
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 149
cataaactaa aagtttaaac atggtcagta agggtgaaga ag                      42

<210> SEQ ID NO 150
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 150
cgtctaaata ctatggatcc ttatttgtac aattcatcca taccac                  46

<210> SEQ ID NO 151
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 151
ggcgcgccga attctcgaca ctggatggcg g                                  31

<210> SEQ ID NO 152
<211> LENGTH: 59
<212> TYPE: DNA
<213> ORGANISM: Artificial Sequence
<220> FEATURE:
<223> OTHER INFORMATION: Artificial DNA Primer

<400> SEQUENCE: 152
atacgaaaat gtaaacattt cctatactcg actagcggcc gctcctcgct gcagacctg    59
```

<210> SEQ ID NO 153
<211> LENGTH: 59
<212> TYPE: DNA
<213> ORGANISM: Artificial Sequence
<220> FEATURE:
<223> OTHER INFORMATION: Artificial DNA Primer

<400> SEQUENCE: 153
atacgaaaat gtaaacattt cctatactcg actagcggcc tttggagttc aatgcgtcc      59

<210> SEQ ID NO 154
<211> LENGTH: 29
<212> TYPE: DNA
<213> ORGANISM: Artificial Sequence
<220> FEATURE:
<223> OTHER INFORMATION: Artificial DNA Primer

<400> SEQUENCE: 154
ctcgagacga tacctgagta ttcccacag                                       29

<210> SEQ ID NO 155
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 155
tgtgggtggt cctaaatggg aggtttcagg gtccataaag c                         41

<210> SEQ ID NO 156
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 156
gcggccgctc ctcgctgcag acctg                                           25

<210> SEQ ID NO 157
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 157
ctgcagcgag gagcggccgc ctcaagaaga tcctttgatc ttttctac                  48

<210> SEQ ID NO 158
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 158
cctatactcg actagcggcc cttaagctag ctggccaggg ccc                       43

<210> SEQ ID NO 159
<211> LENGTH: 28
<212> TYPE: DNA
<213> ORGANISM: Artificial Sequence
<220> FEATURE:
<223> OTHER INFORMATION: Artificial DNA Primer

<400> SEQUENCE: 159
tggcgcagcg ataccgccgc gcacgctg                                    28

<210> SEQ ID NO 160
<211> LENGTH: 27
<212> TYPE: DNA
<213> ORGANISM: Artificial Sequence
<220> FEATURE:
<223> OTHER INFORMATION: Artificial DNA Primer

<400> SEQUENCE: 160
gcggcggtat cgctgcgcca ggtccgg                                     27

<210> SEQ ID NO 161
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 161
cttaagggcc gctagtcgag                                             20

<210> SEQ ID NO 162
<211> LENGTH: 19
<212> TYPE: DNA
<213> ORGANISM: Artificial Sequence
<220> FEATURE:
<223> OTHER INFORMATION: Artificial DNA Primer

<400> SEQUENCE: 162
gcaccggact gtaacgagc                                              19

<210> SEQ ID NO 163
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 163
tggtatcttt cctgtaaatg gaaagtattc                                  30

<210> SEQ ID NO 164
<211> LENGTH: 38
<212> TYPE: DNA
<213> ORGANISM: Artificial Sequence
<220> FEATURE:
<223> OTHER INFORMATION: Artificial DNA Primer

<400> SEQUENCE: 164
ctcgactagc ggcccttaag gatccagctt gcctcgtc                         38

<210> SEQ ID NO 165
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 165
ctcgactagc ggcccttaag ccatgtataa tcatttgcat cc                    42

<210> SEQ ID NO 166

```
<211> LENGTH: 24
<212> TYPE: DNA
<213> ORGANISM: Artificial Sequence
<220> FEATURE:
<223> OTHER INFORMATION: Artificial DNA Primer

<400> SEQUENCE: 166
ggcattacca ccatatacat atcc                                              24

<210> SEQ ID NO 167
<211> LENGTH: 26
<212> TYPE: DNA
<213> ORGANISM: Artificial Sequence
<220> FEATURE:
<223> OTHER INFORMATION: Artificial DNA Primer

<400> SEQUENCE: 167
cttgtctact aaaatctgaa ttgtcc                                            26

<210> SEQ ID NO 168
<211> LENGTH: 439
<212> TYPE: PRT
<213> ORGANISM: Bos taurus

<400> SEQUENCE: 168
```

| Met | Ala | Lys | Glu | Tyr | Phe | Pro | Phe | Thr | Gly | Lys | Ile | Pro | Phe | Glu | Gly |
|---|---|---|---|---|---|---|---|---|---|---|---|---|---|---|---|
| 1 | | | | 5 | | | | | 10 | | | | | 15 | |

Lys Asp Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Glu Cys Pro Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Ala Pro Thr
            100                 105                 110

Ile Ala Glu Tyr Glu Glu Arg Met Lys Ala Ile Thr Asp Tyr Ala Gln
        115                 120                 125

Glu Lys Met Lys Gln Phe Pro Asn Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ser Ile
                165                 170                 175

Asp Ala Thr Ile Lys Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Gly Met Ala Arg Asp Tyr Ala Arg Ala
    210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn

```
                260               265               270
His Ala Thr Leu Ala Gly His Thr Phe Glu His Glu Leu Ala Cys Ala
            275               280               285
Val Asp Ala Gly Met Leu Gly Ser Ile Asp Ala Asn Arg Gly Asp Ala
        290               295               300
Gln Asn Gly Trp Asp Thr Asp Gln Phe Pro Ile Asp Asn Phe Glu Leu
305               310               315               320
Thr Gln Ala Met Leu Glu Ile Ile Arg Asn Gly Gly Leu Gly Asn Gly
                325               330               335
Gly Thr Asn Phe Asp Ala Lys Ile Arg Arg Asn Ser Thr Asp Leu Glu
            340               345               350
Asp Leu Phe Ile Ala His Ile Ser Gly Met Asp Ala Met Ala Arg Ala
        355               360               365
Leu Met Asn Ala Ala Asp Ile Leu Glu Asn Ser Glu Leu Pro Ala Met
    370               375               380
Lys Lys Ala Arg Tyr Ala Ser Phe Asp Ser Gly Ile Gly Lys Asp Phe
385               390               395               400
Glu Asp Gly Lys Leu Thr Phe Glu Gln Val Tyr Glu Tyr Gly Lys Lys
                405               410               415
Val Glu Glu Pro Lys Gln Thr Ser Gly Lys Gln Glu Lys Tyr Glu Thr
            420               425               430
Ile Val Ala Leu His Cys Lys
            435

<210> SEQ ID NO 169
<211> LENGTH: 1495
<212> TYPE: DNA
<213> ORGANISM: Artificial Sequence
<220> FEATURE:
<223> OTHER INFORMATION: Artificial DNA Sequence

<400> SEQUENCE: 169
gattccgcat tggctagcgc tcttcgatac ttccttttaa aatcttgcta ggatacagtt      60
ctcacatcac atccgaacat aaacaaatgc aaacatactt tgatcaatta gacagagtaa    120
gatacgaagg acctaaaagt acaaacccat tggccttccg tcattacaat ccagatgaat    180
tagtactagg taagaggatg gaagatcacc tgagatttgc tgcctgctat tggcacactt    240
tttgctggaa tggtgccgat atgttcggtg tgggtagttt tgatagacca tggcagcaac    300
ctggagaggc tttagaaatg gctaaagaa aagctgaggt tgcttttgaa ttcttccata    360
agcttaatgt accatactac tgctttcatg acgtagacgt tagtcctgag ggagccagct    420
tgaaagaata ctcaaacaac tttgcccaaa tggttgatgt tttagtggag aaacagcaac    480
aatcaggtgt aaagttgttg tggggtactg caaattgttt tacaaatcca agatacggag    540
caggtgctgc cacaaatcca gatccagaag tgttttcatg ggctgcaaca caggtagtaa    600
ctgcaatgaa cgcaactcac aagttaggtg gtgaaaacta cgttctatgg ggtgccgtg    660 aggggtacga gaccttattg aatacagact tgaggcaaga aagagagcaa atcgggaggt    720
ttatgcagct agtcgtcgag cataaacaca aaatcggctt tcaaggaact ctgttgattg    780
agccaaagcc acaagaacct actaaacatc agtacgatta cgatgcttct acagtatatg    840
gctttcttaa gcaatttggt ttagaaaaag atcaaaact aaacattgaa gcaaaccacg    900
ccacattagc tggccattct ttccatcatg aaatcgcaac tgctattgcc ttaggcttat    960
tcggttctgt tgatgccaat agaggagatg cacaattggg ttgggacaca gatcaattcc   1020
```

```
caaattctgt cgaggaaaat gctctggtga tgtacgaaat cttgaaagcc ggtggtttca    1080
cgactggtgg cttgaatttc gacgcaaaag taagaagaca gagtacagac aaatacgatt    1140
tgttctatgg acatatcggt gccatggata ccatggcttt gagtcttaaa gtcgctgcta    1200
gaatgattga agatggagaa ctagataaga gagtcgctaa aagatatgca ggttggaacg    1260
gtgaattagg ccaacagatc ttaactggtc aaatgacatt gacggatatc gcccattatg    1320
ctacacagca taatctagct ccccagcatc attccggtca ccaggaacta ttggagaatt    1380
tggtaaatca ctatttgttt gataaataag gtacctcagt actgacaata aaaagattct    1440
tgttttcaag aacttgtcat ttgtatagtc gaagagcaag atccgtatgt attgg         1495

<210> SEQ ID NO 170
<211> LENGTH: 1495
<212> TYPE: DNA
<213> ORGANISM: Artificial Sequence
<220> FEATURE:
<223> OTHER INFORMATION: Artificial DNA Sequence

<400> SEQUENCE: 170
gattccgcat tggctagcgc tcttcgatac ttccttttaa aatcttgcta ggatacagtt      60
ctcacatcac atccgaacat aaacaaatgt cctatttcga acacattcca gccattagat    120
atgaaggtcc acaatccgac aaccctcttg cctaccatca ttacgatcca gacaaaagag    180
tcctaggtaa gactttggct gaacacctga gaattgctgt ctgttactgg catacctttg    240
tatggccagg acatgacatc tttggtcaag ccgctttcag gagaccctgg cagcaacctg    300
gtgacgcatt agaaagagcc cgtatgaaag cagacgctgc ttttgagttc tttactaagt    360
taggcacccc attctacacc ttccacgaca cagacgtcgc tccggaaggt gactctttga    420
gagagtatgc agccaatttc gctagaatgg tcgactactt aggtgaaaga cagcaggcct    480
caggcgtcag attgttgtgg ggcaccgcca acttgttttc acatccaaga ttcgctgccg    540
gtgccgcaac aaacccaaat cccgatgtat ttgcttgggc tgcaacccaa gtttgtcatg    600
ccttagatgc cactcataga ctaggaggtg agaattacgt cttatggggt ggtagggaag    660
gttacgaaac actattgaat acggatctga agagagaacg tgaccagttt gcaagatttc    720
tgtctatggt agtcgaacac aaacatagga ttggcttcaa aggagcattg ttgatcgaac    780
ctaagcctca agaacccaca aaacatcaat atgactacga tgtcgctacg gttcatggct    840
tcttagttca gtatggtcta caaaatgaga ttagagtcaa cattgaggca aaccacgcta    900
ctcttgcagg ccactcattt catcatgaaa ttgcaaatgc cttcgcacta ggtgtattcg    960
gaagtgttga tgcaaacaga ggtgatccac aaaacggatg ggatacagat cagtttccga   1020
actcagttga agaattgaca ttagccttct atgaaatact acgtcatgga ggtttcacca   1080
caggcggtat gaactttgat gcaaaagtgc gtagacagtc aattgaccct gaagatttgt   1140
tctatggcca tgttggtgct attgatgtgt tggccttggc attagaaaga gctgccgtac   1200
tagtggaaaa tgatagattg gatgcattga gacgtcaaag atacgctcag tgggatgatg   1260
cttttggtag gaaaatccta gcaggaggat ataccttgga atctttagct gccgacgctc   1320
ttgctagggg agtggaccca caacatgcat ctggtgcaca ggaaagactg gaaaacatcg   1380
tcaatcaagc aatctatggt ttaaggtaag gtacctcagt actgacaata aaaagattct   1440
tgttttcaag aacttgtcat ttgtatagtc gaagagcaag atccgtatgt attgg          1495

<210> SEQ ID NO 171
<211> LENGTH: 1495
```

<212> TYPE: DNA
<213> ORGANISM: Artificial Sequence
<220> FEATURE:
<223> OTHER INFORMATION: Artificial DNA Sequence

<400> SEQUENCE: 171

```
gattccgcat tggctagcgc tcttcgatac ttccttttaa aatcttgcta ggatacagtt      60
ctcacatcac atccgaacat aaacaaatgt cctatttcga acacattccc gagattagat     120
atgaaggtcc acaatccgac aaccctcttg cctacagaca ttacgacaaa tccaaaagag     180
tcctaggtaa gactttggaa gaacacctga gaattgctgt ctgttactgg catacctttg     240
tatggccagg agtagacatc tttggtcagg ggactttcag gagaccctgg cagcaagcag     300
gtgacgcaat ggaaagagcc cagcagaaag cagactctgc ttttgagttc ttttctaagt     360
taggcacccc atactacacc ttccacgaca cagacgtcgc tccggaaggt gactctttga     420
aagcatattc agagaatttc actagaattg ccgactactt agctagaaaa cagcaggaca     480
caggcgtcaa attgttgtgg ggcaccgcca acttgttttc acatccaaga tacgctgccg     540
gtgccgcaac aagcccagat cccgagatct ttgcttttgc tgcaacccaa gttagacatg     600
ccttagatgc cactcaaatg ctaggagtg agaattacgt cttatggggt ggtagggaag     660
gttacgatac actattgaat acggatctgg tgagagaacg tgaccagttg gcaagatttc     720
tgcatatggt agtcgaacac aaacataagg ttggcttcaa aggagcattg ttgatcgaac     780
ctaagcctca agaacccaca aaacatcaat ttgactacga tgtcgctacg gttcatggct     840
tcttattgca gtatggtcta gaaaaagaga ttagagtcaa cattgaggca aaccacgcta     900
ctcttgcagg ccactcattt catcatgaaa ttgctactgc ctacgcacta ggcatattcg     960
gaagtgttga tgcaaacaga ggtgatcaac aaaacggatg ggatacagat cagtttccga    1020
actcagttga agaattgaca ttagccttct atgaaatact aaagcatgga ggtttcacca    1080
caggcggtat gaactttgat gcaaaagtgc gtagacagtc agttgacgca gaagatttgt    1140
tctttggcca tattggtgct attgataact tggccttggc agttgaaaga gctgccacat    1200
tgatcgaaaa tgatagattg gaagccttca acgtcaaag atacgctggc tgggaatccg    1260
aatttggtca caaaatccta aaaggagact atagtttgtc cactttagct gccgacgctc    1320
ttactagggg actgaaccca caacatgcat ctggtagaca ggaacaactg gaaaacgtgg    1380
tcaatcaagc aatctattct agaaggtaag gtacctcagt actgacaata aaaagattct    1440
tgttttcaag aacttgtcat ttgtatagtc gaagagcaag atccgtatgt attgg         1495
```

<210> SEQ ID NO 172
<211> LENGTH: 1501
<212> TYPE: DNA
<213> ORGANISM: Artificial Sequence
<220> FEATURE:
<223> OTHER INFORMATION: Artificial DNA Sequence

<400> SEQUENCE: 172

```
gattccgcat tggctagcgc tcttcgatac ttccttttaa aatcttgcta ggatacagtt      60
ctcacatcac atccgaacat aaacaaatgg ctattaccct tggtgcaact gagtacttca     120
aaggtatagg tgccatctca tatgaaggtc ctaaaacaga caatccattg gcatttagat     180
ggtatgacgc aaaccgtcaa gtgtctggta aaactatgaa agaatggttg agatttgcct     240
gtgcctactg gcattccttc aatggttccg gagcagaccc gttcggtgag ccaactcacc     300
ttttttccttg ggatgagtct tcagacccat tgacaagggc tagggctaag gccgatgctg     360
```

| | |
|---|---|
| cctttgaatt catgaccaag atgggtttac cctactattg ttttcatgat gtcgatgttg | 420 |
| tagactatgg taacgatgtg gcagaaaatg acagaagatt acaggcaatg acttcctacc | 480 |
| tagccgaaaa acaaaaagag tctggtattc aattgttgtg ggggaccgca aacttattca | 540 |
| gttctagaag gtatatgaac ggtgctgcta caaacccaga ctttcaggtt ttggctcatg | 600 |
| caggagcaca ggtcaaagct gcactagacg caactattca attaggtggt cagaactatg | 660 |
| ttttctgggg aggtagggaa ggttacatgt cactgttgaa tacaaacaca aaacgtgaga | 720 |
| aagagcattt ggctaggttt ttgcagacgg caagggatta tgcaaggaga caaggcttca | 780 |
| aaggcaagtt tttcatcgaa ccgaaaccat gtgagcctag caagcaccaa tacgattatg | 840 |
| actcagaaac cgtaatcggc ttcttaagac aatatgatct actgtcagac ttcagcctga | 900 |
| acattgaggt taatcacgct acattagctg gtcatacttt tcaacatgaa ttgcaaatgg | 960 |
| ctgcagatgc cggtttactg ggctccattg atgcaaatag aggcgattat cagaatggtt | 1020 |
| gggatacaga tcaatttccc aacaatgtcc ctgaattagc tgaagcaatg ttggtgatct | 1080 |
| tggaggctgg tgggtttggg ggtggtggca tcaactttga tgctaagata agaaggaact | 1140 |
| ccaccgatcc cgaagacctg ttctatgcac atattggtgg tatggacgct ttcgccagag | 1200 |
| ccttgttagt tgcagacgca gttcttcatc agtccgatta caagaaaatc agaactgaga | 1260 |
| gatacgcatc ttttgattct ggtgccggta aagagtttga ggaaggtaaa cttaccctag | 1320 |
| agaacttgag ggaattagca attcagcatg gtgagcctgc accaagatcc ggtaaacagg | 1380 |
| agttgttgga gaacatattg aactatttca tttaaggtac ctcagtactg acaataaaaa | 1440 |
| gattcttgtt tcaagaact tgtcatttgt atagtcgaag agcaagatcc gtatgtattg | 1500 |
| g | 1501 |

<210> SEQ ID NO 173
<211> LENGTH: 1495
<212> TYPE: DNA
<213> ORGANISM: Artificial Sequence
<220> FEATURE:
<223> OTHER INFORMATION: Artificial DNA Sequence

<400> SEQUENCE: 173

| | |
|---|---|
| gattccgcat tggctagcgc tcttcgatac ttccttttaa aatcttgcta ggatacagtt | 60 |
| ctcacatcac atccgaacat aaacaaatgt cctatttcga acacattccc gagattagat | 120 |
| atgaaggtcc acaatccgac aaccctcttg cctacagaca ttacgacaaa acagaagag | 180 |
| tcctaggtaa gactttggaa gaacacctga gattagctgt ctgttactgg cataccttg | 240 |
| tatggccagg agtagacatc tttggtcagg ggactttcag gagaccctgg cagcaagcag | 300 |
| gtgacgcaat ggaaagagcc cagcagaaag cagacgctgc ttttgagttc tttggtaagt | 360 |
| taggcaccccc atactacacc ttccacgaca cagacgtcgc tccggaaggt accaatttga | 420 |
| aagagtattc agagaatttc actagaattg ccgactactt agctagaaaa cagcaggaca | 480 |
| caggcatcaa attgttgtgg ggcaccgcca acttgttttc acatccaaga tacgctgccg | 540 |
| gtgccgcaac aagcccagat cccgaagtat ttgcttttgc tgcaacccaa gttagacatg | 600 |
| ccttagatgc cactgaaaga ctaggagtg agaattacgt cttatgggt ggtagggaag | 660 |
| gttacgatac actattgaat acggatctgg tgagagaacg tgaccagttg gcaagatttc | 720 |
| tgcatatggt agtcgatcac gctcataaga ttggcttcaa aggagcattg ttgatcgaac | 780 |
| ctaagcctca agaacccaca aaacatcaat atgactacga tgtcgctagc gttcatggct | 840 |
| tcttattgca gtatggtcta gaaaaagaga tttgtgtcaa cattgaggca aaccacgcta | 900 |

| | |
|---|---|
| ctcttgcagg ccactcattt catcatgaaa ttgctactgc ctacgcacta ggcatattcg | 960 |
| gaagtgttga tgcaaacaga ggtgatccac aaaacggatg ggatacagat cagtttccga | 1020 |
| actcagttga agaattgaca ttagccttct atgaaatact aaagcatgga ggtttcacca | 1080 |
| caggcggtat gaactttgat agtaaagtgc gtagacagtc agttgaccct gaagatttgt | 1140 |
| tccatggcca tattggtgct attgataact tggccttggc agttgaaaga gctgccgtat | 1200 |
| tgatcgaaaa tgatagattg aacagttca aacgtcaaag atactctggc tgggatgcag | 1260 |
| aattaggtag gaaaatccta gcaggagact atagtttgtc cactttagct gccgacgcta | 1320 |
| tgactagggg agtgaaccca caacatgcat ctggtcaaca ggaaagaatg gaaaacatcg | 1380 |
| tcaatcaagc aatctattct ggaaggtaag gtacctcagt actgacaata aaaagattct | 1440 |
| tgttttcaag aacttgtcat ttgtatagtc gaagagcaag atccgtatgt attgg | 1495 |

<210> SEQ ID NO 174
<211> LENGTH: 1504
<212> TYPE: DNA
<213> ORGANISM: Artificial Sequence
<220> FEATURE:
<223> OTHER INFORMATION: Artificial DNA Sequence

<400> SEQUENCE: 174

| | |
|---|---|
| gattccgcat tggctagcgc tcttcgatac ttccttttaa aatcttgcta ggatacagtt | 60 |
| ctcacatcac atccgaacat aaacaaatgg cttactttga gacggtcaac aagatacaat | 120 |
| ttgaaggagc aagtagtacc aacccttttg ctttcaagta ttacaatcca gaagaggttg | 180 |
| tcaatggtca gaaaatggag gagttattga ggtttagcgt tgcttactgg catactttta | 240 |
| cagcagatgg tacagatccc ttcggtgccg gaacagccat tcgttcttgg gatcacttcc | 300 |
| aaggtatgga cctggccaaa gcaagggttg aagctgcctt cgaattgttc gaaaagctta | 360 |
| atgtgccgtt cttcgcattc catgacgtcg atatcgctcc agagggtaga acactaaaag | 420 |
| aaacaaatga aaatcaagat gagattgtag gaatgatcaa agagtacatg aaaaccagta | 480 |
| aagccaattt gctttggaac actgccaata tgtttacaaa tccgagatac gttcacggtg | 540 |
| gagccacttc tcccaatgca gatgtttttg cttacagtgc tgctaaagtt aagaaagctc | 600 |
| tggaagttgc aaaggaatta ggggctgaga actatgtctt ctggggaggt agagaaggtt | 660 |
| atgagacttt gctgaatacg gacatgaaac ttgagcagga caatttggct aggttctttc | 720 |
| atatggcagt cgattatgca aagaaattg gcttaaacgt tccattcttg atagagccta | 780 |
| agccaaagga accaacaaaa catcaatacg atttcgatgt ggctactggt ttagcttttc | 840 |
| tacagaaata cgatttgacc gactacttca gtttaacat agaggccaat catgccacac | 900 |
| ttgccggaca tacatttgaa catgaattgc gtaccgcaag gatcaatggc atgcttggtt | 960 |
| ctgttgacgc aaatcaaggt gataccttat tgggttggga taccgatgag ttccctacag | 1020 |
| acttgtattc aaatacattg gctatgtatg aaatcttgaa gaatggtggc ttaggcaaag | 1080 |
| gtggcttgaa tttcgatgcc aaggtaagga gaggtagttt tgaagcagat gacttattcc | 1140 |
| atgctcatat tgctggtatg gatgcctttg caattggtct aaaggtggca agtcgtatga | 1200 |
| ttgaagatag agttttagat ggtttcgttg aagaaagata cagttcatac aatgaaggta | 1260 |
| ttggtcttga catagtagaa ggtagggcag acttagaaa gctggaggct cacgcacttc | 1320 |
| aactgaagga gatcaaaaac acttctggta ggactgaaag gttaaaggcc gtcatcaatc | 1380 |
| aatacttatt ggaaaccttg acatccgtga aggcttaagg tacctcagta ctgacaataa | 1440 |

```
aaagattctt gttttcaaga acttgtcatt tgtatagtcg aagagcaaga tccgtatgta    1500
ttgg                                                                 1504

<210> SEQ ID NO 175
<211> LENGTH: 1489
<212> TYPE: DNA
<213> ORGANISM: Artificial Sequence
<220> FEATURE:
<223> OTHER INFORMATION: Artificial DNA Sequence

<400> SEQUENCE: 175
gattccgcat ggctagcgc tcttcgatac ttccttttaa aatcttgcta ggatacagtt      60
ctcacatcac atccgaacat aaacaaatgt cttacttcga gcatttacca gccgttagat    120
acgagggtcc tcagtcagac aatccttttg cttatagaca ttacgatcgt gataagttgg    180
tgttgggcaa agaatggaa gaccacttga gattggcagt ctgttactgg cacacttttg     240
tttggcctgg agtcgatatg tttggtcaag gtacttttca tcgtccctgg cagcaaccag    300
gtgacgctat tgaacgtgct cacgtcaaag cagatagcgc attcgagttt ttctcaaaac    360
ttggtgctcc ctactatacg tttcatgata cagatgttgc ccctgaaggt gattccatta    420
agcattatgt caacaacttt aagggtgtca gagactattt ggctgccaaa caggagcaaa    480
caggcataaa gcttctgtgg ggtacagcaa acttgttcag tcatccaaga tacgcagctg    540
gagccgctac aaatccaaac ccagaagttt tcgcattcgc agcaacccaa gtcttccaag    600
cattagaagc cactcacagg ctaggcggtg agaactatgt actgtggggt ggaagagaag    660
gatatgatac tctgttgaac acagatttga aaagagaacg tgatcaattg gaagattcc    720 tgaatatggt cgttgaacat aaacacaaaa ctgggttcaa aggtgccttg ttaatcgagc    780
caaagcctca agaaccaact aagcatcaat atgattacga tgtggcaact gttcatggct    840
tcttagcaca gtttggacta caaaacgaga ttagagtcaa cattgaagca aaccatgcca    900
ctctggctgg acattctttt caccatgaga ttgctacggc ttacgccttg ggtatctttg    960
gtagtgtgga cgcaaacaga ggcgacccac agaatggatg ggataccgac caattcccaa   1020
attctgtaga agaattgaca ttggccttgt atgagatact acgtcatggc ggttttttcta  1080 ctgggggtat gaactttgac gcaaaggttc gtcgtcagtc agtggcaccg gaagatttgt   1140
tctttggcca tattggagca atagatgtca ttgctttggc tttggaaaga gctgctacta   1200
tggttgaaaa tgacaaattg gcagagttca agactcaaag atacgtagga tgggatactg   1260
agttcggaag gaagatattg tccggaggtt attctttaga atctctagca atggacgcac   1320
tgggtagaag ggtgaatcca caacacgtgt ccggtcaaca ggaattgttg gagaacatag   1380
ttaatcgtgc catctacaaa taaggtacct cagtactgac aataaaaaga ttcttgtttt   1440
caagaacttg tcatttgtat agtcgaagag caagatccgt atgtattgg                1489

<210> SEQ ID NO 176
<211> LENGTH: 1495
<212> TYPE: DNA
<213> ORGANISM: Artificial Sequence
<220> FEATURE:
<223> OTHER INFORMATION: Artificial DNA Sequence

<400> SEQUENCE: 176
gattccgcat ggctagcgc tcttcgatac ttccttttaa aatcttgcta ggatacagtt      60
ctcacatcac atccgaacat aaacaaatgt cctatttcga acacattcca ccgattcatt    120
atgaaggtcc agattccgac aaccctcttg cctttcatca ttacgacaaa accaagaaag    180
```

```
tcctaggtaa gactttggaa gctcacctga gaattgctgt ctgttactgg catacctttg    240
tatggccagg agcagatgtt tttggtcatg gggctttcag gagaccctgg cacgaacctg    300
gtgacgcaat ggaaagagcc aagcagaaag cagacgctgc ttttgagttg ttttctaagt    360
taggcacccc atactacacc ttccacgaca cagacgcagc tccggaaggt aggaatttga    420
aagagtattc agagaatttc gctagaatgg tcgactactt agctagaaaa cagcaggact    480
caggcgtcgg tttgttgtgg ggcaccgcca acttgttttc acatccaaga tacgctgccg    540
gtgccgcaac aaacccaaat cccgaagtat tgcttttgc tgcagcccaa gttagacatg    600
ccttagatgc cactcatcaa ctaggagtg agaattacgt cttatggggt ggtagggaag    660
gttacgatac actattgaat acggaactga gcagagaacg tgagcagttt gcaagatttc    720
tgcatatggt agtcgaacac gctcatagga ttggcttcaa aggaaccttg ttgatcgaac    780
ctaagcctca agaacccaca aaacatcaat atgactacga tgtcgctagc gttcatggct    840
tcttaactca gtatggtcta caaaatgaga ttagagtcaa cattgaggca aaccacgcta    900
ctcttgcagg ccactcattt catcatgaaa ttgctactgc cttcgcacta ggtgtattcg    960
gaagtgttga tgcaaacaga ggtgatccac aaaacggatg ggatacagat cagtttccga   1020
actcagttga agaattgaca ttagccttct atgaaatact acgtcatgga ggtttcacca   1080
caggcggtat gaactttgat gcaaaagtgc gtagacagtc aattgacgca gaagatttgt   1140
tctatggcca tattggtgct attgataact tggccttggc agttgaaaga gctgccaaat   1200
tgatcgaaca tgatagattg gaacagttta gacagcaaag atacgctggc tgggatacag   1260
aatttggtag gaaaatccta gcaggaggat atagtttgac atctttgact gccgacgctc   1320
ttgctagggg actggaccca caacatgcat ctggtagaca ggaatatctg gaaagcgtgg   1380
tcaatcaagc aatctatggt ggaaggtaag gtacctcagt actgacaata aaaagattct   1440
tgttttcaag aacttgtcat ttgtatagtc gaagagcaag atccgtatgt attgg         1495
```

<210> SEQ ID NO 177
<211> LENGTH: 1495
<212> TYPE: DNA
<213> ORGANISM: Artificial Sequence
<220> FEATURE:
<223> OTHER INFORMATION: Artificial DNA Sequence

<400> SEQUENCE: 177

```
gattccgcat tggctagcgc tcttcgatac tccttttaa aatcttgcta ggatacagtt     60
ctcacatcac atccgaacat aaacaaatgt cctactttga acatatccct actattagat    120
acgagggtcc tcaatcagat aatccattgg catatcacca ctatgataga tctaagagag    180
ttctaggtaa aactctagaa gaacacttaa ggattgccgt gtgttactgg catactttg    240 tgtggccagg tgttgacatt tcggtcagg gcacatttga aagaccatgg caacaaccag    300
gcgacgccat ggagagagct caccagaaag cagatgcagc atttgaattg ttttccaaac    360
ttggtacccc atactacacc ttccacgata cagacgttgc tccggaaggt tcatcattga    420
aagaatactc tgaaaacttt gctagaatct cagattactt agccagaaaa caacaggata    480
ctggagtcaa gcttttgtgg gggacagcca acttgttttc ccacccaaga tatgctggtg    540
gtgctgctac ctcccccaat cccgaggttt tgcttttgc tgccactcaa gtttgtcacg    600
ctctagatgc cactcaaaga ttaggaggag aaaactacgt tttgtgggga gggagggaag    660
gttatgatac tttgctgaac acagatctag gaagagaaag gaacaattc gctagattct    720
```

```
tgaatatggt ggtagaacac gcacataaga ttggctttaa gggtactctg ttgattgaac      780
caaaacctca agaaccaact aaacatcaat atgattacga cgttgccgca gttcatggct      840
ttttgaccca atatggattg caaaacgaca ttagggtaaa cattgaagca aatcatgcta      900
cactagccgg tcacagtttc caccacgaaa tcgcttctgc atttgcttta ggcatctttg      960
gttctgttga tgcaaatagg ggtgatcctc aaaacggttg ggacaccgac caatttccaa     1020
attccgtcga agaacttact ttagccttt acgagatatt gaagcatggt ggattcacta     1080
caggtggtat gaactttgac gccaaagtca gaaggcagtc cgtggatgct gaagatttgt     1140
tctatggtca catatctgca atcgacaact tagccttagc agtggaaaga gcagctgttt     1200
tgattgaaaa cgataggctt gaacagttca aaagagaacg ttatgctggc tgggagacag     1260
atttcggaag aaagattttg agtggtggct actctttgtc ttccctggcc acagatgcct     1320
tggacagagg tttgaacccc aagcacagct ctggacaaca agaaagactt gaaggtgtgg     1380
taaaccaagc catctatggt cttcgttaag gtacctcagt actgacaata aaaagattct     1440
tgttttcaag aacttgtcat ttgtatagtc gaagagcaag atccgtatgt attgg          1495

<210> SEQ ID NO 178
<211> LENGTH: 1480
<212> TYPE: DNA
<213> ORGANISM: Artificial Sequence
<220> FEATURE:
<223> OTHER INFORMATION: Artificial DNA Sequence

<400> SEQUENCE: 178
gattccgcat tggctagcgc tcttcgatac ttccttttaa aatcttgcta ggatacagtt       60
ctcacatcac atccgaacat aaacaaatgg cttacttcac agacattccc aagattactt      120
atcaaggtcc aaagagcaaa gatccattgt ccttcaaaca ctacaatcca gacgaagtta      180
tagaaggcaa aacgatgagg gaacatttac gttttggtgc tgcttattgg cacgtaatga      240
gaaatgcatt aggtgatcct tttggaggag gaaccgcatt gatgccatgg gacgacggaa      300
cggattctgt caacaatgca aagaaagggg cagacgtttt cttcgagttc ttagagaaga      360
tcgatattga cttctattgc ttccacgacc gtgatgttgc acctgagttg ggcgatttca      420
agaaaagcag cgatgcatta cgtcaagtta cagctcattt gggtgaattg cagaaagctt      480
ctggtaagaa gctactatgg ggtacagctt gcctgttctc acatcccaga tactctcagg      540
gtgccggaac cagcccagat ttacgtgttt tcacatatgc cgctgcccaa gttaaagaag      600
ccatggatag tactcatgct ttaggaggct gggttatac ttttggggga ggtagagaag      660
gttatgcttc cttgttaaac acggacatga aaagagaatt agatcactta gcagcattgc      720
tacatatggc agtagcttac aaaaaggaaa ttggctttgg tggtcagttt tacatagaac      780
ctaaaccaag ggagccgagc acccaccaat atgactcaga tagcgctgca tgcttgaatt      840
tcttgcgtga gtacggtttg ctagaacact tcaagttgaa tcttgaaacc aaccatgcaa      900
ccttagccgg ataccatg gagcatgaaa tgaccgttgc aattggtgcc gatgccttag      960
gttctgtaga tgcaaaccaa ggcgatacct tattgggttg ggatacagat caattcccta     1020
cagacattta cggacggcc aaaatcatgt tgaaagtctt ggaaatgggt ggatttacta     1080
ctggcggatt gaatttcgat gctaaaagac gtagagaatc acatgaacct attgacttat     1140
tccatgctca tatcggaggt atggatgcct ttgctagagg gctgaagata gctgccgctg     1200
ttcgtgcaga tggccgtatt ggcgactttg taaaggcaag atattcatca tgggacagtg     1260
atcttggtgc caagatagaa tcaggaaaag ccacacttgc tgaactagct gaattggcca     1320
```

```
gtactggagg tgaaccacaa ttggcatctg gaagacaaga attgatggag aacatcttga   1380
atgaattgat ataaggtacc tcagtactga caataaaaag attcttgttt tcaagaactt   1440
gtcatttgta tagtcgaaga gcaagatccg tatgtattgg                         1480

<210> SEQ ID NO 179
<211> LENGTH: 1483
<212> TYPE: DNA
<213> ORGANISM: Artificial Sequence
<220> FEATURE:
<223> OTHER INFORMATION: Artificial DNA Sequence

<400> SEQUENCE: 179
gattccgcat tggctagcgc tcttcgatac ttccttttaa aatcttgcta ggatacagtt     60
ctcacatcac atccgaacat aaacaaatga aggaatactt tcctcagata ggtaagatac    120
aattcgaagg caaagattcc aagaatccaa tggcttttca ttactatgat gccgaaaagg    180
tcataatggg taagcctatg aaggagtggc tgaggtttgc tatggcttgg tggcatacat    240
tatgtgccga gggatccgac cagtttggcc caggtaccaa acattcccg tggaatgagg     300 gtgccgacgc tattgagaag gccaagaaca aagccgacgc tggttttgag attatgacca    360
agcttggttt tccctatttc tgcttccatg atgttgattt gattgccgag ggcaacacag    420
tagaagaata cgaatcaaac ttagccgcaa taacggacta cttgaaagag aaaatggatg    480
ctaccggtat caagttgtta tggtctacag caaatgtttt tggtaacgct aggtatatga    540
atggcgcatc aacgaaccca gactttgacg ttgtcgctag agcaattgtc cagatcaaga    600
atgctataga cgcaggcatc aaattgggag ccgagaacta tgtcttttgg ggtggaaggg    660
agggatacat gtccttattg aatacagatc agaaacgtga aggaacacac atggctacaa    720
tgctgaggat ggcaagagat tatgcaagaa gtaaggatt tactggaacc ttcttgattg     780
agccaaaacc catggaacca gtaaacatca gtatgacgt tgacacagag acagtcatcg      840
gcttcttaag agcccatggt ttggataaag actttaaggt caacattgaa gttaaccatg    900
ctaccttagc tggacatacc tttgagcatg aactagcatg cgctgtggat gctggcatgt    960
taggttctat tgatgcaaac aggggtgact atcaaaatgg ctgggataca gatcagtttc   1020
ctatcgatca attcgatctt gttcaggcct ggatggagat cttaagagga gggggtttgg   1080
gaacaggtgg gaccaatttc gacgctaaaa ctagaagaaa ttctaccgac ttggaagaca   1140
tcttcttagc acacatatcc ggtatggatg ccatggctcg tgccctggaa tctgccgcaa   1200
agcttctgga ggaatccccc atcaaacaga tgaaagcaga ccgttatgct tcatttgata   1260
gcggtttagg caaaaagttt gaaaatggag aaatgacttt agaagaagcc tatgagtatg   1320
gtaaacaagt cggcgaacct aaacagacat ccggcaagca agagttgtat gaagctatcg   1380
tagcaatgta ttgttaaggt acctcagtac tgacaataaa aagattcttg ttttcaagaa   1440
cttgtcattt gtatagtcga agagcaagat ccgtatgtat tgg                     1483

<210> SEQ ID NO 180
<211> LENGTH: 1474
<212> TYPE: DNA
<213> ORGANISM: Artificial Sequence
<220> FEATURE:
<223> OTHER INFORMATION: Artificial DNA Sequence

<400> SEQUENCE: 180
gattccgcat tggctagcgc tcttcgatac ttccttttaa aatcttgcta ggatacagtt     60
```

```
ctcacatcac atccgaacat aaacaaatga cagacttctt tgctggcatt ccacaattga      120
cttaccaagg cacggatgct acttcagatt ttgcttttag gcactacaag ccggatgaag      180
ttgtgttggg taggagaatg aagaccatc taagatttgc tgtttgctac tggcacaatt       240
tcgcttggcc aggtaacgat ccttttggtg gacaaacttt tcaaagaccc tggtttggcg      300
atacaatgga acacgctaag ttgaaggcag atgttgcttt cgagatgttt aggatattga      360
atacacccta cttttgtttc catgacgccg atatgcgtcc cgagggcgac tcattcgcac      420
aaaacacaag aaacttggaa gaaatgacag actacattgc agccaaaatg gaggctggtg      480
gacccaagtt actttggggg acagccaact tgttttctca taggaggtac atgtcaggtg      540
cagctacaaa tccggatccg gatatctttg cattctctgc tgccactgtc aaaacttgta      600
tggacgccac tcataggtta aacggtgaaa actatgtctt atggggaggt cgtgaaggct      660
atgaaaccct tttgaacaca gatctatcaa aagagttgga tcacatgggt aggttttga      720 gtatggtcgt tgactacaaa cacaagattg gattcaaagg tgccattttg attgaaccaa      780
aacctcagga accaaccaaa caccagtacg actatgacgt agctacagtt tttggattcc      840
tacaaagatt cggtttggaa aaagaagtta aggtcaacat agaacaaggc catgccatat      900
tggctgggca tagcttcgaa catgagatag ccctggcagc ttcattaggc atctttggta      960
gcatagatat gaatagaaac gactaccaat ctggttggga tacagatcaa ttccccaaca     1020
atacacctga agtcgctctg gcctactatg agatattgag agcaggaggt tttacaacag     1080
gagggaccaa ctttgacgca aaacttagac gtcagtcttt ggacgcagag gacttaatct     1140
tagctcacgc aggagctatg gacgtatgcg ctagaggttt gaaagctgcc gctgccatgt     1200
tagaagatgg caagcttgaa gcagccagag ctgctagata tgctggatgg gatacgccag     1260
aagcacaagc catgttacat tccaatttgg atagaatcgc agaagatgta ttgaaccatg     1320
atgttaatcc caacccgaga agtggtaggc aagagcgttt ggaaaatcta gtcaatagat     1380
acttgtaagg tacctcagta ctgacaataa aaagattctt gttttcaaga acttgtcatt     1440
tgtatagtcg aagagcaaga tccgtatgta ttgg                                 1474

<210> SEQ ID NO 181
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 181
gctagcgctc ttcgatactt c                                                 21

<210> SEQ ID NO 182
<211> LENGTH: 26
<212> TYPE: DNA
<213> ORGANISM: Artificial Sequence
<220> FEATURE:
<223> OTHER INFORMATION: Artificial DNA Primer

<400> SEQUENCE: 182
gatcttgctc ttcgactata caaatg                                            26

<210> SEQ ID NO 183
<211> LENGTH: 32
<212> TYPE: DNA
<213> ORGANISM: Artificial Sequence
<220> FEATURE:
<223> OTHER INFORMATION: Artificial DNA Primer
```

```
<400> SEQUENCE: 183
ataaacaagg tacctcagta ctgacaataa aa                              32

<210> SEQ ID NO 184
<211> LENGTH: 27
<212> TYPE: DNA
<213> ORGANISM: Artificial Sequence
<220> FEATURE:
<223> OTHER INFORMATION: Artificial DNA Primer

<400> SEQUENCE: 184
gcgtttaaac gaattcgggc gcgccga                                    27

<210> SEQ ID NO 185
<211> LENGTH: 53
<212> TYPE: DNA
<213> ORGANISM: Artificial Sequence
<220> FEATURE:
<223> OTHER INFORMATION: Artificial DNA Primer

<400> SEQUENCE: 185
gcttaattaa aagctgttta tctctagtat tactctttag acaaaaaaat tgt        53

<210> SEQ ID NO 186
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 186
aggtaccttg tttatgttcg gatgtgatgt                                 30

<210> SEQ ID NO 187
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 187
cctatctgag gaaagtattc cttcatgtcg acttgtttat gttcg                45
```

XYLOSE FERMENTING YEAST STRAINS AND PROCESSES THEREOF FOR ETHANOL PRODUCTION

CROSS-REFERENCE TO RELATED APPLICATIONS

This application is a 35 U.S.C. 371 national application of PCT/EP2018/064347, filed May 31, 2018, which claims priority or the benefit from U.S. Provisional Application Ser. No. 62/513,266, filed May 31, 2017. The contents of these applications are fully incorporated herein by reference.

REFERENCE TO A SEQUENCE LISTING

This application contains a Sequence Listing in computer readable form, which is incorporated herein by reference.

BACKGROUND

Ethanol is a transportation fuel commonly blending into gasoline. Cellulosic material is used as a feedstock in ethanol production processes. There are several processes in the art for making cellulose and hemicelluloses hydrolysates containing glucose, mannose, xylose and arabinose. Glucose and mannose are efficiently converted to ethanol during natural anaerobic metabolism. However, to obtain an economically relevant process at industrial scale, xylose within the hydrolysates must be fermented into ethanol.

Efforts to establish and improve pentose (e.g., xylose) utilization of the yeast *Saccharomyces cerevisiae* have been reported (Kim et al., 2013, *Biotechnol Adv.* 31(6):851-61). These include heterologous expression of xylose reductase (XR) and xylitol dehydrogenase (XDH) from naturally xylose fermenting yeasts such as *Scheffersomyces* (*Pichia*) *stipitis* and various *Candida* species, as well as the overexpression of xylulokinase (XK) and the four enzymes in the non-oxidative pentose phosphate pathway (PPP), namely transketolase (TKL), transaldolase (TAL), ribose-5-phosphate ketol-isomerase (RKI) and D-ribulose-5-phosphate 3-epimerase (RPE). Modifying the co-factor preference of *S. stipitis* XR towards NADH in such systems has been found to provide metabolic advantages as well as improving anaerobic growth. Pathways replacing the XR/XDH with heterologous xylose isomerase (XI) have also been reported. These and other modifications have been described in, e.g., WO2003/062430, WO2009/017441, WO2010/059095, WO2012/113120, and WO2012/135110.

Despite improvement of ethanol production processes from cellulosic material over the past decade, there is still a need for improved industrial yeasts and processes that can be used to enable commercially-viable ethanol production using cellulosic plant waste substrates.

SUMMARY

Described herein are recombinant host cells capable of fermentation using xylose as a carbon source. In one aspect, the recombinant cells comprise a heterologous polynucleotide encoding a xylose isomerase.

In some embodiments, the xylose isomerase has at least 60%, e.g., at least 65%, 70%, 75%, 80%, 85%, 90%, 95%, 97%, 98%, 99%, or 100% sequence identity to SEQ ID NO: 22.

In some embodiments, the recombinant cells are capable of:
higher growth rate on a pentose (e.g., xylose);
higher consumption of pentose (e.g., xylose); and/or
higher ethanol production,
when compared to the same cell without the heterologous polynucleotide encoding a xylose isomerase (e.g., under conditions described herein).

In some embodiments, the recombinant cells further comprise a heterologous polynucleotide encoding a xylulokinase (XK), e.g., an XK having at least 60%, e.g., at least 65%, 70%, 75%, 80%, 85%, 90%, 95%, 97%, 98%, 99%, or 100% sequence identity to SEQ ID NO: 25.

In some embodiments, the recombinant cells further comprise a heterologous polynucleotide encoding a hexose transporter, e.g., a hexose transporter having at least 60%, e.g., at least 65%, 70%, 75%, 80%, 85%, 90%, 95%, 97%, 98%, 99%, or 100% sequence identity to SEQ ID NO: 26.

In some embodiments, the recombinant cells further comprise a heterologous polynucleotide encoding a polypeptide selected from a ribulose 5 phosphate 3-epimerase (RPE1), a ribulose 5 phosphate isomerase (RKI1), a transketolase (TKL1), a transaldolase (TAL1).

In some embodiments, the recombinant cells comprise a disruption to one or more endogenous genes encoding a GPD, GPP, and/or an aldose reductase (e.g., GRE3 or YPR1).

In some embodiments, the recombinant cells are selected from *Saccharomyces, Rhodotorula, Schizosaccharomyces, Kluyveromyces, Pichia, Hansenula, Rhodosporidium, Candida, Yarrowia, Lipomyces, Cryptococcus,* or *Dekkera* sp. cells. In some embodiment, the recombinant cells are *Saccharomyces cerevisiae* cells.

Also described are processes of producing ethanol using the recombinant cells. One aspect is a process for producing ethanol, comprising cultivating a recombinant cell described herein in a fermentable medium under suitable conditions to produce ethanol. In another aspect is a process for producing ethanol, comprising: (a) saccharifying a cellulosic and/or starch-containing material with an enzyme composition; and (b) fermenting the saccharified material of step (a) with a recombinant cell described herein.

In some embodiments of the processes, fermentation consumes an increased amount of pentose (e.g., xylose) when compared to fermentation using an identical cell without the heterologous polynucleotide encoding a xylose isomerase under the same conditions (e.g., under conditions described herein).

In some embodiments of the processes, fermentation provides higher ethanol yield when compared to fermentation using an identical cell without the heterologous polynucleotide encoding a xylose isomerase under the same conditions (e.g., under conditions described herein).

In some embodiments of the processes, fermentation is conducted under anaerobic conditions.

In some embodiments of the processes, the further comprises recovering the fermentation product from the fermentation.

In some embodiments of the processes, saccharification occurs on a cellulosic material, and the cellulosic material is pretreated. In some embodiments, the pretreatment is a dilute acid pretreatment.

In some embodiments of the processes, saccharification occurs on a cellulosic material, and the enzyme composition comprises one or more enzymes selected from a cellulase, an AA9 polypeptide, a hemicellulase, a CIP, an esterase, an expansin, a ligninolytic enzyme, an oxidoreductase, a pectinase, a protease, and a swollenin. In some embodiments, the cellulase is one or more enzymes selected from an endoglucanase, a cellobiohydrolase, and a beta-glucosidase.

In some embodiments, the hemicellulase is one or more enzymes selected a xylanase, an acetylxylan esterase, a feruloyl esterase, an arabinofuranosidase, a xylosidase, and a glucuronidase.

In some embodiments of the processes, saccharification and fermentation are performed simultaneously in a simultaneous saccharification and fermentation (SSF). In some embodiments, saccharification and fermentation are performed sequentially (SHF).

DEFINITIONS

Figure 1:
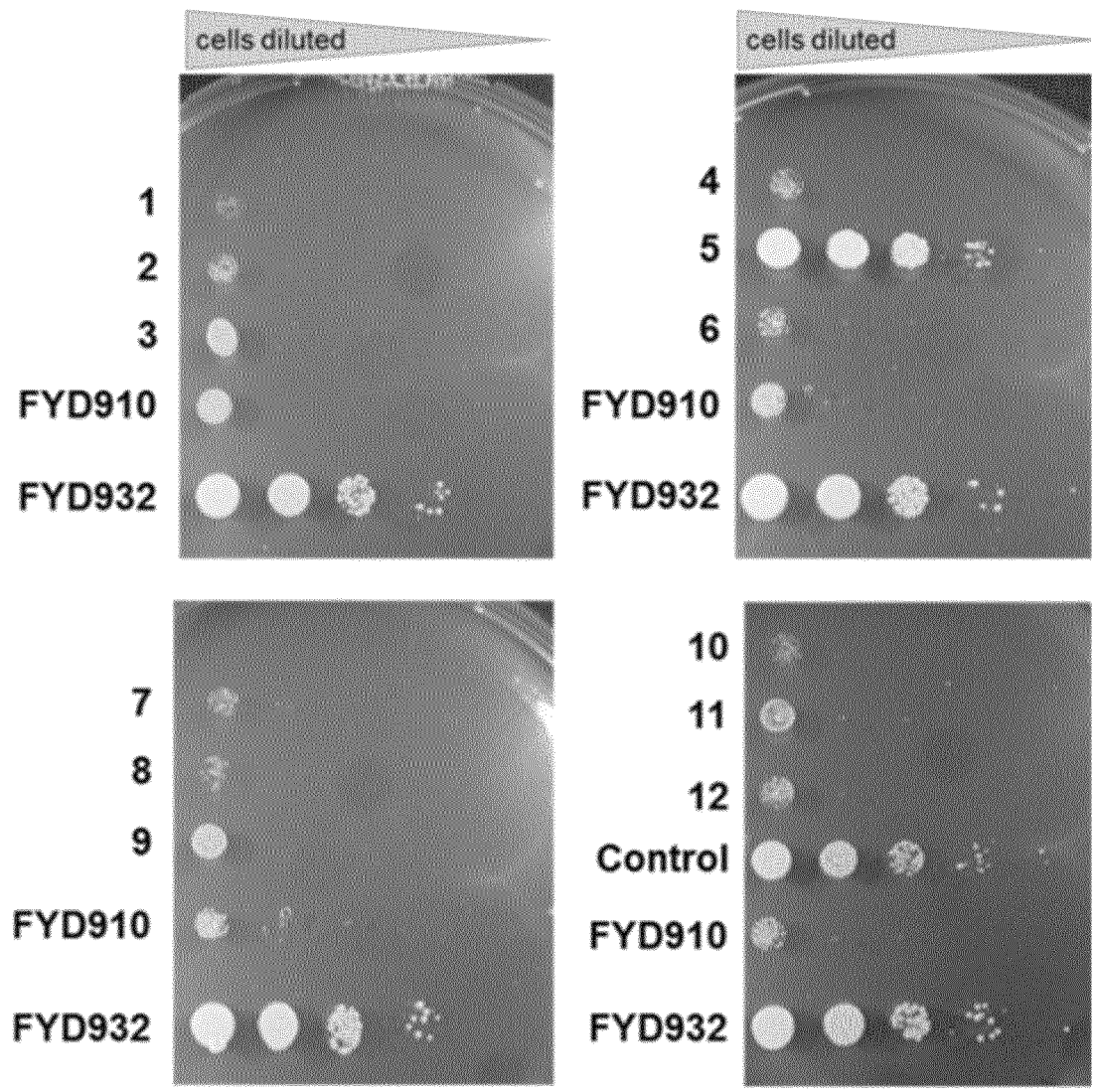
FIG. 1 shows anaerobic cell growth experiments after 30 days on xylose-containing SX2 plates at 30° C., as described in Example 3. Rows 1-12 correspond to xylose isomerase-encoding strains constructed by GAP-repair with partial 2µ plasmid (expressing the XIs of SEQ ID NOs: 18, 12, 2, 14, 22, 8, 4, 24, 20, 6, 10 and 16, respectively), as described in Example 2. "Control" indicates a xylose isomerase-encoding strain constructed by GAP-repair with partial 2µ plasmid and expressing the xylose isomerase of SEQ ID NO: 168.

Unless defined otherwise or clearly indicated by context, all technical and scientific terms used herein have the same meaning as commonly understood by one of ordinary skill in the art.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Auxiliary Activity 9: The term "Auxiliary Activity 9" or "AA9" means a polypeptide classified as a lytic polysaccharide monooxygenase (Quinlan et al., 2011, Proc. Natl. Acad. Sci. USA 208: 15079-15084; Phillips et al., 2011, ACS Chem. Biol. 6: 1399-1406; Lin et al., 2012, Structure 20: 1051-1061). AA9 polypeptides were formerly classified into the glycoside hydrolase Family 61 (GH61) according to Henrissat, 1991, Biochem. J. 280: 309-316, and Henrissat and Bairoch, 1996, Biochem. J. 316: 695-696.

AA9 polypeptides enhance the hydrolysis of a cellulosic material by an enzyme having cellulolytic activity. Cellulolytic enhancing activity can be determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40 C-80° C., e.g., 50° C., 55° C., 60° C., 65° C., or 70° C., and a suitable pH, such as 4-9, e.g., 4.5, 5.0, 5.5, 6.0, 6.5, 7.0, 7.5, 8.0, or 8.5, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST™ 1.5 L (Novozymes A/S, Bagsvaerd, Denmark) and beta-glucosidase as the source of the cellulolytic activity, wherein the beta-glucosidase is present at a weight of at least 2-5% protein of the cellulase protein loading. In one embodiment, the beta-glucosidase is an *Aspergillus oryzae* beta-glucosidase (e.g., recombinantly produced in *Aspergillus oryzae* according to WO 02/095014). In another embodiment, the beta-glucosidase is an *Aspergillus fumigatus* beta-glucosidase (e.g., recombinantly produced in *Aspergillus oryzae* as described in WO 02/095014).

AA9 polypeptide enhancing activity can also be determined by incubating an AA9 polypeptide with 0.5% phosphoric acid swollen cellulose (PASC), 100 mM sodium acetate pH 5, 1 mM $MnSO_4$, 0.1% gallic acid, 0.025 mg/ml of Aspergillus *fumigatus* beta-glucosidase, and 0.01% TRITON@ X-100 (4-(1,1,3,3-tetramethylbutyl)phenyl-polyethylene glycol) for 24-96 hours at 40° C. followed by determination of the glucose released from the PASC.

AA9 polypeptide enhancing activity can also be determined according to WO2013/028928 for high temperature compositions.

AA9 polypeptides enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, J. Basic Microbiol. 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 µmole of p-nitrophenolate anion produced per minute at 40° C., pH 5 from 1 mM p-nitrophenyl-beta-D-xyloside in 100 mM sodium citrate containing 0.01% TWEEN® 20.

Catalase: The term "catalase" means a hydrogen-peroxide:hydrogen-peroxide oxidoreductase (EC 1.11.1.6) that catalyzes the conversion of $2H_2O_2$ to $O_2+2 H_2O$. For purposes of the present invention, catalase activity is determined according to U.S. Pat. No. 5,646,025. One unit of catalase activity equals the amount of enzyme that catalyzes the oxidation of 1 µmole of hydrogen peroxide under the assay conditions.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teed, 1997, *Trends in Biotechnology* 15: 160-167; Teen et al., 1998, *Biochem. Soc. Trans.* 26: 173-178). Cellobiohydrolase activity can be determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman No1 filter paper, microcrystalline cellulose, bacterial cellulose, algal cellulose, cotton, pretreated lignocellulose, etc. The most common total cellulolytic activity assay is the filter paper assay using Whatman No1 filter paper as the substrate. The assay was established by the *International Union of Pure and Applied Chemistry* (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column chromatography (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in *Handbook on Bioethanol* (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in Advances in Biochemical Engineering/Biotechnology, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one embodiment, the cellulosic material is any biomass material. In another embodiment, the cellulosic material is lignocellulose, which comprises cellulose, hemicelluloses, and lignin.

In an embodiment, the cellulosic material is agricultural residue, herbaceous material (including energy crops), municipal solid waste, pulp and paper mill residue, waste paper, or wood (including forestry residue).

In another embodiment, the cellulosic material is *arundo*, bagasse, bamboo, corn cob, corn fiber, corn stover, *miscanthus*, rice straw, switchgrass, or wheat straw.

In another embodiment, the cellulosic material is aspen, *eucalyptus*, fir, pine, poplar, spruce, or willow.

In another embodiment, the cellulosic material is algal cellulose, bacterial cellulose, cotton linter, filter paper, microcrystalline cellulose (e.g., AVICEL@), or phosphoric-acid treated cellulose.

In another embodiment, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional processes known in the art, as described herein. In a preferred embodiment, the cellulosic material is pretreated.

Coding sequence: The term "coding sequence" or "coding region" means a polynucleotide sequence, which specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a sequence of genomic DNA, cDNA, a synthetic polynucleotide, and/or a recombinant polynucleotide.

Control sequence: The term "control sequence" means a nucleic acid sequence necessary for polypeptide expression. Control sequences may be native or foreign to the polynucleotide encoding the polypeptide, and native or foreign to each other. Such control sequences include, but are not limited to, a leader sequence, polyadenylation sequence, propeptide sequence, promoter sequence, signal peptide sequence, and transcription terminator sequence. The control sequences may be provided with linkers for the purpose of introducing specific restriction sites facilitating ligation of the control sequences with the coding region of the polynucleotide encoding a polypeptide.

Disruption: The term "disruption" means that a coding region and/or control sequence of a referenced gene is partially or entirely modified (such as by deletion, insertion, and/or substitution of one or more nucleotides) resulting in the absence (inactivation) or decrease in expression, and/or the absence or decrease of enzyme activity of the encoded polypeptide. The effects of disruption can be measured using techniques known in the art such as detecting the absence or decrease of enzyme activity using from cell-free extract measurements referenced herein; or by the absence or decrease of corresponding mRNA (e.g., at least 25% decrease, at least 50% decrease, at least 60% decrease, at least 70% decrease, at least 80% decrease, or at least 90% decrease); the absence or decrease in the amount of corresponding polypeptide having enzyme activity (e.g., at least 25% decrease, at least 50% decrease, at least 60% decrease, at least 70% decrease, at least 80% decrease, or at least 90% decrease); or the absence or decrease of the specific activity of the corresponding polypeptide having enzyme activity (e.g., at least 25% decrease, at least 50% decrease, at least 60% decrease, at least 70% decrease, at least 80% decrease, or at least 90% decrease). Disruptions of a particular gene of interest can be generated by processes known in the art, e.g., by directed homologous recombination (see Processes in Yeast Genetics (1997 edition), Adams, Gottschling, Kaiser, and Stems, Cold Spring Harbor Press (1998)).

Endogenous gene: The term "endogenous gene" means a gene that is native to the referenced host cell. "Endogenous gene expression" means expression of an endogenous gene.

Endoglucanase: The term "endoglucanase" means a 4-(1, 3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components.

Endoglucanase activity can be determined by measuring reduction in substrate viscosity or increase in reducing ends determined by a reducing sugar assay (Zhang et al., 2006, *Biotechnology Advances* 24: 452-481). Endoglucanase activity can also be determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of the polypeptide including, but not limited to, transcription, post-transcriptional modification, translation, post-translational modification, and secretion. Expression can be measured—for example, to detect increased expression—by techniques known in the art, such as measuring levels of mRNA and/or translated polypeptide.

Expression vector: The term "expression vector" means a linear or circular DNA molecule that comprises a polynucleotide encoding a polypeptide and is operably linked to control sequences, wherein the control sequences provide for expression of the polynucleotide encoding the polypeptide. At a minimum, the expression vector comprises a promoter sequence, and transcriptional and translational stop signal sequences.

Fermentable medium: The term "fermentable medium" or "fermentation medium" refers to a medium comprising one or more (e.g., two, several) sugars, such as glucose, fructose, sucrose, cellobiose, xylose, xylulose, arabinose, mannose, galactose, and/or soluble oligosaccharides, wherein the medium is capable, in part, of being converted (fermented) by a host cell into a desired product, such as ethanol. In some instances, the fermentation medium is derived from a natural source, such as sugar cane, starch, or cellulose, and may be the result of pretreating the source by enzymatic hydrolysis (saccharification). The term fermentation medium is understood herein to refer to a medium before the fermenting microorganism(s) is(are) added, such as, a medium resulting from a saccharification process, as well as a medium used in a simultaneous saccharification and fermentation process (SSF).

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0.

Heterologous polynucleotide: The term "heterologous polynucleotide" is defined herein as a polynucleotide that is not native to the host cell; a native polynucleotide in which structural modifications have been made to the coding region; a native polynucleotide whose expression is quantitatively altered as a result of a manipulation of the DNA by recombinant DNA techniques, e.g., a different (foreign)

promoter; or a native polynucleotide in a host cell having one or more extra copies of the polynucleotide to quantitatively alter expression. A "heterologous gene" is a gene comprising a heterologous polynucleotide.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

Host cell: The term "host cell" means any cell type that is susceptible to transformation, transfection, transduction, and the like with a nucleic acid construct or expression vector. The term "host cell" encompasses any progeny of a parent cell that is not identical to the parent cell due to mutations that occur during replication. The term "recombinant cell" is defined herein as a non-naturally occurring host cell comprising one or more (e.g., two, several) heterologous polynucleotides.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Nucleic acid construct: The term "nucleic acid construct" means a polynucleotide comprises one or more (e.g., two, several) control sequences. The polynucleotide may be single-stranded or double-stranded, and may be isolated from a naturally occurring gene, modified to contain segments of nucleic acids in a manner that would not otherwise exist in nature, or synthetic.

Operably linked: The term "operably linked" means a configuration in which a control sequence is placed at an appropriate position relative to the coding sequence of a polynucleotide such that the control sequence directs expression of the coding sequence.

Pentose: The term "pentose" means a five carbon monosaccharide (e.g., xylose, arabinose, ribose, lyxose, ribulose, and xylulose). Pentoses, such as D-xylose and L-arabinose, may be derived, e.g., through saccharification of a plant cell wall polysaccharide.

Pretreated corn stover: The term "Pretreated Corn Stover" or "PCS" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity".

For purposes described herein, the degree of sequence identity between two amino acid sequences is determined using the Needleman-Wunsch algorithm (Needleman and Wunsch, *J. Mol. Biol.* 1970, 48, 443-453) as implemented in the Needle program of the EMBOSS package (EMBOSS: The European Molecular Biology Open Software Suite, Rice et al., *Trends Genet* 2000, 16, 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the-nobrief option) is used as the percent identity and is calculated as follows:

(Identical Residues×100)/(Length of the Referenced Sequence−Total Number of Gaps in Alignment)

For purposes described herein, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the-nobrief option) is used as the percent identity and is calculated as follows:

(Identical Deoxyribonucleotides×100)/(Length of Referenced Sequence−Total Number of Gaps in Alignment)

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Xylose Isomerase: The term "Xylose Isomerase" or "XI" means an enzyme which can catalyze D-xylose into D-xylulose in vivo, and convert D-glucose into D-fructose in vitro. Xylose isomerase is also known as "glucose isomerase" and is classified as E.C. 5.3.1.5. As the structure of the enzyme is very stable, the xylose isomerase is one of the good models for studying the relationships between protein structure and functions (Karimaki et al., Protein Eng Des Sel, 12004, 17 (12):861-869). Moreover, the extremely important industrial application value makes the xylose isomerase is seen as important industrial enzyme as protease and amylase (Tian Shen et al., Microbiology Bulletin, 2007, 34 (2): 355-358; Bhosale et al., Microbiol Rev, 1996, 60 (2): 280-300). The scientists keep high concern and carried out extensive research on xylose isomerase. Since 1970s, the applications of the xylose isomerase have focused on the production of high fructose syrup and fuel ethanol. In recent years, scientists have found that under certain conditions, the xylose isomerase can be used for producing many important rare sugars, which are the production materials in the pharmaceutical industry, such as ribose, mannose, arabinose and lyxose (Karimaki et al., Protein Eng Des Se, 12004, 17 (12): 861-869).These findings bring new vitality in the research on the xylose isomerase.

Reference to "about" a value or parameter herein includes embodiments that are directed to that value or parameter per se. For example, description referring to "about X" includes the embodiment "X". When used in combination with measured values, "about" includes a range that encompasses at least the uncertainty associated with the process of measuring the particular value, and can include a range of plus or minus two standard deviations around the stated value.

Likewise, reference to a gene or polypeptide that is "derived from" another gene or polypeptide X, includes the gene or polypeptide X.

As used herein and in the appended claims, the singular forms "a," "or," and "the" include plural referents unless the context clearly dictates otherwise.

It is understood that the embodiments described herein include "consisting" and/or "consisting essentially of" embodiments. As used herein, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments.

DETAILED DESCRIPTION

Described herein, inter alia, are recombinant cells, such as yeast, capable of converting hexoses and pentoses into ethanol, e.g., in processes as described below. As described in the Examples below, the Applicant has found that expression of the xylose isomerase of SEQ ID NO: 22 in a cell, such as *Saccharomyces cerevisiae* yeast, provides unexpected properties, such as exceptional growth on xylose, when compared to other xylose isomerases.

In one aspect is a recombinant cell (e.g., yeast) comprising a heterologous polynucleotide encoding a xylose isomerase.

In one embodiment, the xylose isomerase comprises or consists of the amino acid sequence of SEQ ID NO: 22. In another embodiment, the xylose isomerase is a fragment of the xylose isomerase of SEQ ID NO: 22 (e.g., wherein the fragment has xylose isomerase activity). In one embodiment, the number of amino acid residues in the fragment is at least 75%, e.g., at least 80%, 85%, 90%, or 95% of the number of amino acid residues in the xylose isomerase of SEQ ID NO: 22.

The xylose isomerase may be a variant of the xylose isomerase of SEQ ID NO: 22. In one embodiment, the xylose isomerase has at least 60%, e.g., at least 65%, 70%, 75%, 80%, 85%, 90%, 95%, 97%, 98%, 99%, or 100% sequence identity to the xylose isomerase of SEQ ID NO: 22.

In one embodiment, the xylose isomerase sequence differs by no more than ten amino acids, e.g., by no more than five amino acids, by no more than four amino acids, by no more than three amino acids, by no more than two amino acids, or by one amino acid from amino acid sequence of xylose isomerase of SEQ ID NO: 22. In one embodiment, the xylose isomerase has an amino acid substitution, deletion, and/or insertion of one or more (e.g., two, several) of amino acid sequence of the xylose isomerase of SEQ ID NO: 22. In some embodiments, the total number of amino acid substitutions, deletions and/or insertions is not more than 10, e.g., not more than 9, 8, 7, 6, 5, 4, 3, 2, or 1

The amino acid changes are generally of a minor nature, that is conservative amino acid substitutions or insertions that do not significantly affect the folding and/or activity of the protein; small deletions, typically of one to about 30 amino acids; small amino-terminal or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/le, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the xylose isomerase, alter the substrate specificity, change the pH optimum, and the like.

Essential amino acids can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for activity to identify amino acid residues that are critical to the activity of the molecule. See also, Hilton et al., 1996, *J. Biol. Chem.* 271: 4699-4708. The active site or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with other xylose isomerase that are related to the referenced xylose isomerase.

Guidance on the structure-activity relationship of xylose isomerases described herein can be inferred from numerous crystal structures analyzed and known in the art (See, for example, Hess et al., 1998, *Appl. Environ. Microbiol.* 64(7), 2357-2360; Blow, et al., 1992, *Faraday Discuss,* 93, 67-73). Additional guidance on the structure-activity relationship of xylose isomerases can be determined using multiple sequence alignment (MSA) techniques well-known in the art. Based on the teachings herein, the skilled artisan could make similar alignments with any of the xylose isomerases described herein (e.g., the XI of SEQ ID NOs: 2, 4, 6, 8, 10, 12, 14, 16, 18, 20, 22, or 24) or with those known in the art. Such alignments aid the skilled artisan to determine potentially relevant domains (e.g., binding domains or catalytic domains), as well as which amino acid residues are conserved and not conserved among the different xylose isomerase sequences. It is appreciated in the art that changing an amino acid that is conserved at a particular position between disclosed polypeptides will more likely result in a change in biological activity (Bowie et al., 1990, *Science* 247: 1306-1310: "Residues that are directly involved in protein functions such as binding or catalysis will certainly be among the most conserved"). In contrast, substituting an amino acid that is not highly conserved among the polypeptides will not likely or significantly alter the biological activity.

Single or multiple amino acid substitutions, deletions, and/or insertions can be made and tested using known processes of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other processes that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling processes can be combined with high-throughput, automated screening processes to detect activity of cloned, mutagenized polypeptides expressed by host cells (Ness et al., 1999, *Nature Biotechnology* 17: 893-896). Mutagenized DNA molecules that encode active xylose isomerases can be recovered from the host cells and rapidly sequenced using standard processes in the art. These processes allow the rapid determination of the importance of individual amino acid residues in a polypeptide.

In another embodiment, the heterologous polynucleotide encoding the xylose isomerase comprises a coding sequence having at least 60%, e.g., at least 65%, at least 70%, at least 75%, at least 80%, at least 85%, at least 90%, at least 95%, at least 96%, at least 97%, at least 98%, at least 99%, or 100% sequence identity to nucleotides of SEQ ID NO: 21.

In one embodiment, the heterologous polynucleotide encoding the xylose isomerase comprises or consists of the coding sequence of SEQ ID NO: 21. In another embodiment, the heterologous polynucleotide encoding the xylose isomerase comprises a subsequence of the coding sequence of SEQ ID NO: 21 (e.g., wherein the subsequence encodes a polypeptide having xylose isomerase activity). In another embodiment, the number of nucleotides residues in the coding subsequence is at least 75%, e.g., at least 80%, 85%, 90%, or 95% of the number of the referenced coding sequence.

The referenced coding sequence of any related aspect or embodiment described herein can be the native coding sequence or a degenerate sequence, such as a codon-optimized coding sequence designed for a particular host cell.

The polynucleotide coding sequence of SEQ ID NO: 21, or a subsequence thereof, as well as the polypeptide of SEQ ID NO: 22, or a fragment thereof, may be used to design nucleic acid probes to identify and clone DNA encoding a xylose isomerase from strains of different genera or species according to processes well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin).

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 21, or a subsequence thereof, the carrier material is used in a Southern blot.

In one embodiment, the nucleic acid probe is a polynucleotide comprising SEQ ID NO: 21; or a subsequence thereof. In another embodiment, the nucleic acid probe is a polynucleotide that encodes the xylose isomerase of SEQ ID NO: 22; or a fragment thereof.

For purposes of the probes described above, hybridization indicates that the polynucleotide hybridizes to a labeled nucleic acid probe, or the full-length complementary strand thereof, or a subsequence of the foregoing; under very low to very high stringency conditions. Molecules to which the nucleic acid probe hybridizes under these conditions can be detected using, for example, X-ray film. Stringency and washing conditions are defined as described supra.

In one embodiment, the xylose isomerase is encoded by a polynucleotide that hybridizes under at least low stringency conditions, e.g., medium stringency conditions, medium-high stringency conditions, high stringency conditions, or very high stringency conditions with the full-length complementary strand of SEQ ID NO: 21. (Sambrook et al., 1989, *Molecular Cloning, A Laboratory Manual,* 2d edition, Cold Spring Harbor, N.Y.).

The xylose isomerase may be obtained from microorganisms of any suitable genus, including those readily available within the UniProtKB database (www.uniprot.org).

The xylose isomerase may be a bacterial xylose isomerase. For example, the xylose isomerase may be a Gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* xylose isomerase, or a Gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* xylose isomerase.

In one embodiment, the xylose isomerase is a *Bacillus alkalophilus, Bacillus amyloliquefaciens, Bacillus brevis, Bacillus circulans, Bacillus clausii, Bacillus coagulans, Bacillus firmnnus, Bacillus lautus, Bacillus lentus, Bacillus*

*licheniformis, Bacillus megaterium, Bacillus pumilus, Bacillus stearothermophilus, Bacillus subtilis,* or *Bacillus thuringiensis* xylose isomerase.

In another embodiment, the xylose isomerase is a *Streptococcus equisimilis, Streptococcus pyogenes, Streptococcus uberis,* or *Streptococcus equi* subsp. *Zooepidemicus* xylose isomerase.

In another embodiment, the xylose isomerase is a *Streptomyces achromogenes, Streptomyces avermitilis, Streptomyces coelicolor, Streptomyces griseus,* or *Streptomyces lividans* xylose isomerase.

The xylose isomerase may be a fungal xylose isomerase. For example, the xylose isomerase may be a yeast xylose isomerase such as a *Candida, Kluyveromyces, Pichia, Saccharomyces, Schizosaccharomyces, Yarrowia* or *Issatchenkia* xylose isomerase; or a filamentous fungal xylose isomerase such as an *Acremonium, Agaricus, Altemaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* xylose isomerase.

In another embodiment, the xylose isomerase is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* xylose isomerase.

In another embodiment, the xylose isomerase is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* xylose isomerase.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

The xylose isomerases may also be identified and obtained from other sources including microorganisms isolated from nature (e.g., soil, composts, water, silage, etc.) or DNA samples obtained directly from natural materials (e.g., soil, composts, water, silage, etc.) using the above-mentioned probes. Techniques for isolating microorganisms and DNA directly from natural habitats are well known in the art. The polynucleotide encoding a xylose isomerase may then be derived by similarly screening a genomic or cDNA library of another microorganism or mixed DNA sample.

Once a polynucleotide encoding a xylose isomerase has been detected with a suitable probe as described herein, the sequence may be isolated or cloned by utilizing techniques that are known to those of ordinary skill in the art (see, e.g., Sambrook et al., 1989, supra).

Techniques used to isolate or clone polynucleotides encoding xylose isomerases include isolation from genomic DNA, preparation from cDNA, or a combination thereof. The cloning of the polynucleotides from such genomic DNA can be effected, e.g., by using the well-known polymerase chain reaction (PCR) or antibody screening of expression libraries to detect cloned DNA fragments with shares structural features. See, e.g., Innis et al., 1990, *PCR: A Guide to Processes and Application, Academic Press*, New York. Other nucleic acid amplification procedures such as ligase chain reaction (LCR), ligated activated transcription (LAT) and nucleotide sequence-based amplification (NASBA) may be used.

The xylose isomerase may be a fused polypeptide or cleavable fusion polypeptide in which another polypeptide is fused at the N-terminus or the C-terminus of the xylose isomerase. Examples of fused polypeptides having xylose isomerase activity can be found, e.g., in WO2016/024218. A fused polypeptide may be produced by fusing a polynucleotide encoding another polypeptide to a polynucleotide encoding the xylose isomerase. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

In one aspect, the recombinant cell (e.g., yeast cell) further comprises a heterologous polynucleotide encoding a xylulokinase (XK). A xylulokinase, as used herein, provides enzymatic activity for converting D-xylulose to xylulose 5-phosphate. The xylulokinase may be any xylulokinase that is suitable for the host cells and the processes described herein, such as a naturally occurring xylulokinase or a variant thereof that retains xylulokinase activity. In one embodiment, the xylulokinase is present in the cytosol of the host cells.

In some embodiments, the recombinant cells comprising a heterologous polynucleotide encoding a xylulokinase have an increased level of xylulokinase activity compared to the host cells without the heterologous polynucleotide encoding the xylulokinase, when cultivated under the same conditions. In some embodiments, the host cells have an increased level of xylose isomerase activity of at least 5%, e.g., at least 10%, at least 15%, at least 20%, at least 25%, at least 50%, at least 100%, at least 150%, at least 200%, at least 300%, or at 500% compared to the host cells without the heterologous polynucleotide encoding the xylulokinase, when cultivated under the same conditions.

Exemplary xylulokinases that can be used with the recombinant host cells and processes of use described herein include, but are not limited to, the *Saccharomyces cerevisiae* xylulokinase of SEQ ID NO: 25. Additional polynucleotides encoding suitable xylulokinases may be obtained from microorganisms of any genus, including those readily available within the UniProtKB database (www.uniprot.org). In one embodiment, the xylulokinases is a bacterial, a yeast, or a filamentous fungal xylulokinase, e.g., obtained from any of the microorganisms described herein, as described supra under the sections related to xylose isomerases.

The xylulokinase coding sequences can also be used to design nucleic acid probes to identify and clone DNA encoding xylulokinases from strains of different genera or species, as described supra.

The polynucleotides encoding xylulokinases may also be identified and obtained from other sources including microorganisms isolated from nature (e.g., soil, composts, water, etc.) or DNA samples obtained directly from natural materials (e.g., soil, composts, water, etc,) as described supra.

Techniques used to isolate or clone polynucleotides encoding xylulokinases are described supra.

In one embodiment, the xylulokinase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to any xylulokinase described herein (e.g., the *Saccharomyces cerevisiae* xylulokinase of SEQ ID NO: 25). In one embodiment, the xylulokinase sequence differs by no more than ten amino acids, e.g., by no more than five amino acids, by no more than four amino acids, by no more than three amino acids, by no more than two amino acids, or by one amino acid from any xylulokinase described herein (e.g., the *Saccharomyces cerevisiae* xylulokinase of SEQ ID NO: 25). In one embodiment, the xylulokinase comprises or consists of the amino acid sequence of any xylulokinase described herein (e.g., the *Saccharomyces cerevisiae* xylulokinase of SEQ ID NO: 25), allelic variant, or a fragment thereof having xylulokinase activity. In one embodiment, the xylulokinase has an amino acid substitution, deletion, and/or insertion of one or more (e.g., two, several) amino acids. In some embodiments, the total number of amino acid substitutions, deletions and/or insertions is not more than 10, e.g., not more than 9, 8, 7, 6, 5, 4, 3, 2, or 1.

In some embodiments, the xylulokinase has at least 20%, e.g., at least 40%, at least 50%, at least 60%, at least 70%, at least 80%, at least 90%, at least 95%, at least 96%, at least 97%, at least 98%, at least 99%, or 100% of the xylulokinase activity of any xylulokinase described herein (e.g., the *Saccharomyces cerevisiae* xylulokinase of SEQ ID NO: 25) under the same conditions.

In one embodiment, the xylulokinase coding sequence hybridizes under at least low stringency conditions, e.g., medium stringency conditions, medium-high stringency conditions, high stringency conditions, or very high stringency conditions with the full-length complementary strand of the coding sequence from any xylulokinase described herein (e.g., the *Saccharomyces cerevisiae* xylulokinase of SEQ ID NO: 25). In one embodiment, the xylulokinase coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any xylulokinase described herein (e.g., the *Saccharomyces cerevisiae* xylulokinase of SEQ ID NO: 25).

In one embodiment, the heterologous polynucleotide encoding the xylulokinase comprises the coding sequence of any xylulokinase described herein (e.g., the *Saccharomyces cerevisiae* xylulokinase of SEQ ID NO: 25). In one embodiment, the heterologous polynucleotide encoding the xylulokinase comprises a subsequence of the coding sequence from any xylulokinase described herein, wherein the subsequence encodes a polypeptide having xylulokinase activity. In one embodiment, the number of nucleotides residues in the subsequence is at least 75%, e.g., at least 80%, 85%, 90%, or 95% of the number of the referenced coding sequence.

The xylulokinases can also include fused polypeptides or cleavable fusion polypeptides, as described supra.

In one aspect, the recombinant cell (e.g., yeast cell) further comprises a heterologous polynucleotide encoding a hexose transporter. The hexose transporter may be any hexose transporter that is suitable for the host cells and the processes described herein, such as a naturally occurring hexose transporter or a variant thereof that retains hexose transporter activity. In one embodiment, the hexose transporter is present in the cytosol of the host cells.

In some embodiments, the recombinant cells comprising a heterologous polynucleotide encoding a hexose transporter have an increased level of hexose transporter activity compared to the host cells without the heterologous polynucleotide encoding the hexose transporter, when cultivated under the same conditions. In some embodiments, the host cells have an increased level of hexose transporter activity of at least 5%, e.g., at least 10%, at least 15%, at least 20%, at least 25%, at least 50%, at least 100%, at least 150%, at least 200%, at least 300%, or at 500% compared to the host cells without the heterologous polynucleotide encoding the hexose transporter, when cultivated under the same conditions.

Exemplary hexose transporters that can be used with the recombinant host cells and processes of use described herein include, but are not limited to, the *Saccharomyces cerevisiae* hexose transporters HXT1, HXT2, HXT3, HXT4, HXT5, HXT6, HXT7, or GAL2 as described in the art ((Goncalves et. al, 2014, *Enzyme Microb. Technol.*, 63: 13-20; WO2005/058947; and U.S. Ser. No. 62/430,690, the content of which is hereby incorporated by reference in their entireties). Additional polynucleotides encoding suitable hexose transporters may be obtained from microorganisms of any genus, including those readily available within the UniProtKB database (www.uniprot.org). In one embodiment, the hexose transporter is a bacterial, a yeast, or a filamentous fungal hexose transporter, e.g., obtained from any of the microorganisms described herein, as described supra under the sections related to xylose isomerases.

The hexose transporter coding sequences can also be used to design nucleic acid probes to identify and clone DNA encoding hexose transporters from strains of different genera or species, as described supra.

The polynucleotides encoding hexose transporters may also be identified and obtained from other sources including microorganisms isolated from nature (e.g., soil, composts, water, etc.) or DNA samples obtained directly from natural materials (e.g., soil, composts, water, etc,) as described supra.

Techniques used to isolate or clone polynucleotides encoding hexose transporters are described supra.

In one embodiment, the hexose transporter has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to any hexose transporter described herein (e.g., the *Saccharomyces cerevisiae* hexose transporter of SEQ ID NO: 26). In one embodiment, the hexose transporter sequence differs by no more than ten amino acids, e.g., by no more than five amino acids, by no more than four amino acids, by no more than three amino acids, by no more than two amino acids, or by one amino acid from any hexose transporter described herein (e.g., the *Saccharomyces cerevisiae* hexose transporter of SEQ ID NO: 26). In one embodiment, the hexose transporter comprises or consists of the amino acid sequence of any hexose transporter described herein (e.g., the *Saccharomyces cerevisiae* hexose transporter of SEQ ID NO: 26), allelic variant, or a fragment thereof having hexose transporter activity. In one embodiment, the hexose transporter has an amino acid substitution, deletion, and/or insertion of one or more (e.g., two, several) amino acids. In some embodiments, the total number of amino acid substitutions, deletions and/or insertions is not more than 10, e.g., not more than 9, 8, 7, 6, 5, 4, 3, 2, or 1.

In some embodiments, the hexose transporter has at least 20%, e.g., at least 40%, at least 50%, at least 60%, at least 70%, at least 80%, at least 90%, at least 95%, at least 96%, at least 97%, at least 98%, at least 99%, or 100% of the hexose transporter activity of any hexose transporter described herein (e.g., the *Saccharomyces cerevisiae* hexose transporter of SEQ ID NO: 26) under the same conditions.

In one embodiment, the hexose transporter coding sequence hybridizes under at least low stringency conditions, e.g., medium stringency conditions, medium-high stringency conditions, high stringency conditions, or very high stringency conditions with the full-length complementary strand of the coding sequence from any hexose transporter described herein (e.g., the *Saccharomyces cerevisiae* hexose transporter of SEQ ID NO: 26). In one embodiment, the hexose transporter coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any hexose transporter described herein (e.g., the *Saccharomyces cerevisiae* hexose transporter of SEQ ID NO: 26).

In one embodiment, the heterologous polynucleotide encoding the hexose transporter comprises the coding sequence of any hexose transporter described herein (e.g., the *Saccharomyces cerevisiae* hexose transporter of SEQ ID NO: 26). In one embodiment, the heterologous polynucleotide encoding the hexose transporter comprises a subsequence of the coding sequence from any hexose transporter described herein, wherein the subsequence encodes a polypeptide having hexose transporter activity. In one embodiment, the number of nucleotides residues in the subsequence is at least 75%, e.g., at least 80%, 85%, 90%, or 95% of the number of the referenced coding sequence.

The hexose transporters can also include fused polypeptides or cleavable fusion polypeptides, as described supra.

In one aspect, the recombinant cell (e.g., yeast cell) further comprises a heterologous polynucleotide encoding a ribulose 5 phosphate 3-epimerase (RPE1). A ribulose 5 phosphate 3-epimerase, as used herein, provides enzymatic activity for converting L-ribulose 5-phosphate to L-xylulose 5-phosphate (EC 5.1.3.22). The RPE1 may be any RPE1 that is suitable for the host cells and the processes described herein, such as a naturally occurring RPE1 or a variant thereof that retains RPE1 activity. In one embodiment, the RPE1 is present in the cytosol of the host cells.

In one embodiment, the recombinant cell comprises a heterologous polynucleotide encoding a ribulose 5 phosphate 3-epimerase (RPE1), wherein the RPE1 is *Saccharomyces cerevisiae* RPE1, or an RPE1 having at least 60%, e.g., at least 65%, 70%, 75%, 80%, 85%, 90%, 95%, 97%, 98%, 99%, or 100% sequence identity to a *Saccharomyces cerevisiae* RPE1.

In one aspect, the recombinant cell (e.g., yeast cell) further comprises a heterologous polynucleotide encoding a ribulose 5 phosphate isomerase (RKI1). A ribulose 5 phosphate isomerase, as used herein, provides enzymatic activity for converting ribose-5-phophate to ribulose 5-phosphate. The RKI1 may be any RKI1 that is suitable for the host cells and the processes described herein, such as a naturally occurring RKI1 or a variant thereof that retains RKI1 activity. In one embodiment, the RKI1 is present in the cytosol of the host cells.

In one embodiment, the recombinant cell comprises a heterologous polynucleotide encoding a ribulose 5 phosphate isomerase (RKI1), wherein the RKI1 is a *Saccharomyces cerevisiae* RKI1, or an RKI1 having at least 60%, e.g., at least 65%, 70%, 75%, 80%, 85%, 90%, 95%, 97%, 98%, 99%, or 100% sequence identity to a *Saccharomyces cerevisiae* RKI1.

In one aspect, the recombinant cell (e.g., yeast cell) further comprises a heterologous polynucleotide encoding a transketolase (TKL1). The TKL1 may be any TKL1 that is suitable for the host cells and the processes described herein, such as a naturally occurring TKL1 or a variant thereof that retains TKL1 activity. In one embodiment, the TKL1 is present in the cytosol of the host cells.

In one embodiment, the recombinant cell comprises a heterologous polynucleotide encoding a transketolase (TKL1), wherein the TKL1 is a *Saccharomyces cerevisiae* TKL1, or a TKL1 having at least 60%, e.g., at least 65%, 70%, 75%, 80%, 85%, 90%, 95%, 97%, 98%, 99%, or 100% sequence identity to a *Saccharomyces cerevisiae* TKL1.

In one aspect, the recombinant cell (e.g., yeast cell) further comprises a heterologous polynucleotide encoding a transaldolase (TAL1). The TAL1 may be any TAL1 that is suitable for the host cells and the processes described herein, such as a naturally occurring TAL1 or a variant thereof that retains TAL1 activity. In one embodiment, the TAL1 is present in the cytosol of the host cells.

In one embodiment, the recombinant cell comprises a heterologous polynucleotide encoding a transketolase (TAL1), wherein the TAL1 is a *Saccharomyces cerevisiae* TAL1, or a TAL1 having at least 60%, e.g., at least 65%, 70%, 75%, 80%, 85%, 90%, 95%, 97%, 98%, 99%, or 100% sequence identity to a *Saccharomyces cerevisiae* TAL1.

The host cells described herein may be adapted to utilize pentose (e.g., xylose) before and/or after recombinant modification by selection of mutants, either spontaneous or induced (e.g. by radiation or chemicals), for growth on pentose (e.g., xylose), such on xylose as sole carbon source under anaerobic conditions. Selection of mutants may be performed by techniques including serial passaging of cultures as e.g. described by Kuyper et al. (2004, *FEMS Yeast Res.* 4: 655-664) or by cultivation under selective pressure in a chemostat culture. The host cells described herein may be produced using breeding techniques before and/or after recombinant modification, as described in WO2005/121337 (the content of which is hereby incorporated by reference).

In some embodiments, the host cells described herein produce essentially no xylitol, e.g. the xylitol produced is below the detection limit or e.g. less than about 5, about 2, about 1, about 0.5, or about 0.3% of the carbon consumed on a molar basis.

In some embodiments, the recombinant cells described herein (e.g., a cell comprising a heterologous polynucleotide encoding a xylose isomerase described herein) have improved anaerobic growth on a pentose (e.g., xylose). In one embodiment, the recombinant cell is capable of higher anaerobic growth rate on a pentose (e.g., xylose) compared to the same cell without the heterologous polynucleotide encoding a xylose isomerase at about or after 10, 20, 30, 40 50, 60 or 70 hours (e.g., under conditions described herein).

In some embodiments, the recombinant cells described herein (e.g., a cell comprising a heterologous polynucleotide encoding a xylose isomerase described herein) have the ability to grow on xylose as sole carbon source at a rate of at least about 0.05, about 0.1, about 0.2, about 0.25 or about 0.3 $h^{-1}$ under aerobic conditions, or, if applicable, at a rate of at least about 0.03, about 0.05, about 0.07, about 0.08, about 0.09, about 0.1, about 0.12, about 0.15 or about 0.2 $h^{-1}$ under anaerobic conditions. In some embodiments, the recombinant cell has the ability to grow on a mixture of glucose and xylose (in a 1:1 weight ratio) as sole carbon source at a rate of at least about 0.05, about 0.1, about 0.2, about 0.25 or about 0.3 $h^{-1}$ under aerobic conditions, or, if applicable, at a rate of at least about 0.03, about 0.05, about 0.1, about 0.12, about 0.15, or about 0.2 $h^{-1}$ under anaerobic conditions.

In some embodiments, the recombinant cells described herein (e.g., a cell comprising a heterologous polynucleotide encoding a xylose isomerase described herein) have a biomass yield on xylose that is at least about 40, about 50, about 55, about 60, about 70, about 80, about 85, about 90, about 95, about 98 or about 99% of the recombinant cell's biomass yield on glucose. In some embodiments, the cell's biomass yield on xylose, is about equal to the host cell's biomass yield on glucose.

In some embodiments, the recombinant cells described herein (e.g., a cell comprising a heterologous polynucleotide encoding a xylose isomerase described herein) have higher pentose (e.g., xylose) consumption. In one embodiment, the recombinant cell is capable of higher pentose (e.g., xylose) consumption compared to the same cell without the heterologous polynucleotide encoding a xylose isomerase at about or after 10, 20, 30, 40 50, 60 or 70 hours fermentation (e.g., under conditions described herein). In one embodiment, the recombinant cell is capable of consuming more than 65%, e.g., at least 70%, 75%, 80%, 85%, 90%, 95% of pentose (e.g., xylose) in the medium at about or after 10, 20, 30, 40 50, 60 or 70 hours fermentation (e.g., under conditions described herein). In one embodiment, the recombinant cell is capable of consuming more than 65%, e.g., at least 70%, 75%, 80%, 85%, 90%, 95% of glucose in the medium at about or after 10, 20, 30, 40 50, 60 or 70 hours fermentation (e.g., under conditions described herein). In one embodiment, the recombinant cell is capable of consuming more than 65%, e.g., at least 70%, 75%, 80%, 85%, 90%, 95% of pentose (e.g., xylose) in the medium, and is capable of consuming more than 65%, e.g., at least 70%, 75%, 80%, 85%, 90%, 95% of glucose in the medium, at about or after 10, 20, 30, 40 50, 60 or 70 hours fermentation (e.g., under conditions described herein).

In some embodiments, the recombinant cells described herein (e.g., a cell comprising a heterologous polynucleotide encoding a xylose isomerase described herein) have a specific xylose consumption rate of at least about 200, about 250, about 300, about 346, about 350, about 400, about 500, about 600, about 750, or about 1000 mg xylose/g cells/h.

In some embodiments, the recombinant cells described herein (e.g., a cell comprising a heterologous polynucleotide encoding a xylose isomerase described herein) have higher ethanol production. In one embodiment, the recombinant cell is capable of higher ethanol production compared to the same cell without the heterologous polynucleotide encoding a xylose isomerase at about or after 10, 20, 30, 40 50, 60 or 70 hours fermentation (e.g., under conditions described herein).

In some embodiments, the recombinant cells described herein (e.g., a cell comprising a heterologous polynucleotide encoding a xylose isomerase described herein) are capable of an ethanol yield on xylose that is at least about 40, about 50, about 55, about 60, about 70, about 80, about 85, about 90, about 95 about 98 or about 99% of the recombinant cell's yield on glucose. In some embodiments, the ethanol yield of a recombinant cell described herein is about equal to the cell's yield of ethanol on glucose. It is understood that in the comparison of yields on glucose and xylose both yields are compared under aerobic conditions or both under anaerobic conditions.

In some embodiments, the recombinant cells described herein (e.g., a cell comprising a heterologous polynucleotide encoding a xylose isomerase described herein) are capable of using arabinose, that is, may be capable of converting L-arabinose into L-ribulose and/or xylulose 5-phosphate and/or into a desired fermentation product, such as ethanol. Recombinant cells capable produce ethanol from L-arabinose may be produced by modifying a cell introducing the araA (L-arabinose isomerase), araB (L-ribulokinase) and araD (L-ribulose-5-P4-epimerase) genes from a suitable source (e.g., as described in WO2003/095627 and WO2011/003893).

Gene Disruotions

The recombinant cells described herein may also comprise one or more (e.g., two, several) gene disruptions, e.g., to divert sugar metabolism from undesired products to ethanol. In some aspects, the recombinant host cells produce a greater amount of ethanol compared to the cell without the one or more disruptions when cultivated under identical conditions. In some aspects, one or more of the disrupted endogenous genes is inactivated.

In certain embodiments, the recombinant cells provided herein comprise a disruption of one or more endogenous genes encoding enzymes involved in producing alternate fermentative products such as glycerol or other byproducts such as acetate or diols. For example, the cells provided herein may comprise a disruption of one or more of glycerol 3-phosphate dehydrogenase (GPD, catalyzes reaction of dihydroxyacetone phosphate to glycerol 3-phosphate), glycerol 3-phosphatase (GPP, catalyzes conversion of glycerol-3 phosphate to glycerol), glycerol kinase (catalyzes conversion of glycerol 3-phosphate to glycerol), dihydroxyacetone kinase (catalyzes conversion of dihydroxyacetone phosphate to dihydroxyacetone), glycerol dehydrogenase (catalyzes conversion of dihydroxyacetone to glycerol), and aldehyde dehydrogenase (ALD, e.g., converts acetaldehyde to acetate). Disruptions to GPD1/GPD2 and GPP1/GPP2 are discussed in, e.g., WO2014/180820. In some embodiments, the recombinant cells provided herein comprise a disruption to an aldose reductase (catalyzes conversion of xylose or xylulose to xylitol; e.g., GRE3 or YPR1; See, Traff et al., 2001, *Appl. Environ. Microbiol.* 67: 5668-74).

Modeling analysis can be used to design gene disruptions that additionally optimize utilization of the pathway. One exemplary computational process for identifying and designing metabolic alterations favoring biosynthesis of a desired product is the OptKnock computational framework, Burgard et al., 2003, *Biotechnol. Bioeng.* 84: 647-657.

The recombinant cells comprising a gene disruption may be constructed using processes well known in the art, including those processes described herein. A portion of the gene can be disrupted such as the coding region or a control sequence required for expression of the coding region. Such a control sequence of the gene may be a promoter sequence or a functional part thereof, i.e., a part that is sufficient for affecting expression of the gene. For example, a promoter sequence may be inactivated resulting in no expression or a weaker promoter may be substituted for the native promoter sequence to reduce expression of the coding sequence. Other control sequences for possible modification include, but are not limited to, a leader, propeptide sequence, signal sequence, transcription terminator, and transcriptional activator.

The recombinant cells comprising a gene disruption may be constructed by gene deletion techniques to eliminate or reduce expression of the gene. Gene deletion techniques enable the partial or complete removal of the gene thereby eliminating their expression. In such processes, deletion of the gene is accomplished by homologous recombination using a plasmid that has been constructed to contiguously contain the 5' and 3' regions flanking the gene.

The recombinant cells comprising a gene disruption may also be constructed by introducing, substituting, and/or removing one or more (e.g., two, several) nucleotides in the gene or a control sequence thereof required for the transcription or translation thereof. For example, nucleotides may be inserted or removed for the introduction of a stop codon, the removal of the start codon, or a frame-shift of the open reading frame. Such a modification may be accomplished by site-directed mutagenesis or PCR generated mutagenesis in accordance with processes known in the art. See, for example, Botstein and Shortle, 1985, *Science* 229: 4719; Lo et al., 1985, *Proc. Natl. Acad. Sci. U.S.A.* 81: 2285; Higuchi et al., 1988, *Nucleic Acids Res* 16: 7351; Shimada, 1996, *Meth. Mol. Biol.* 57: 157; Ho et al., 1989, *Gene* 77: 61; Horton et al., 1989, *Gene* 77: 61; and Sarkar and Sommer, 1990, *BioTechniques* 8: 404.

The recombinant cells comprising a gene disruption may also be constructed by inserting into the gene a disruptive nucleic acid construct comprising a nucleic acid fragment homologous to the gene that will create a duplication of the region of homology and incorporate construct DNA between the duplicated regions. Such a gene disruption can eliminate gene expression if the inserted construct separates the promoter of the gene from the coding region or interrupts the coding sequence such that a non-functional gene product results. A disrupting construct may be simply a selectable marker gene accompanied by 5' and 3' regions homologous to the gene. The selectable marker enables identification of transformants containing the disrupted gene.

The recombinant cells comprising a gene disruption may also be constructed by the process of gene conversion (see, for example, Iglesias and Trautner, 1983, *Molecular General Genetics* 189: 73-76). For example, in the gene conversion process, a nucleotide sequence corresponding to the gene is mutagenized in vitro to produce a defective nucleotide sequence, which is then transformed into the recombinant strain to produce a defective gene. By homologous recombination, the defective nucleotide sequence replaces the endogenous gene. It may be desirable that the defective nucleotide sequence also comprises a marker for selection of transformants containing the defective gene.

The recombinant cells comprising a gene disruption may be further constructed by random or specific mutagenesis using processes well known in the art, including, but not limited to, chemical mutagenesis (see, for example, Hopwood, The Isolation of Mutants in Processes in Microbiology (J.R. Norris and D.W. Ribbons, eds.) pp. 363-433, Academic Press, New York, 1970). Modification of the gene may be performed by subjecting the parent strain to mutagenesis and screening for mutant strains in which expression of the gene has been reduced or inactivated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing processes.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosogaunidine (NTG)O-methyl hydroxylamine, nitrous acid, ethyl methane sulphonate (EMS), sodium bisulphite, formic acid, and nucleotide analogues. When such agents are used, the mutagenesis is typically performed by incubating the parent strain to be mutagenized in the presence of the mutagenizing agent of choice under suitable conditions, and selecting for mutants exhibiting reduced or no expression of the gene.

A nucleotide sequence homologous or complementary to a gene described herein may be used from other microbial sources to disrupt the corresponding gene in a recombinant strain of choice.

In one aspect, the modification of a gene in the recombinant cell is unmarked with a selectable marker. Removal of the selectable marker gene may be accomplished by culturing the mutants on a counter-selection medium. Where the selectable marker gene contains repeats flanking its 5' and 3' ends, the repeats will facilitate the looping out of the selectable marker gene by homologous recombination when the mutant strain is submitted to counter-selection. The selectable marker gene may also be removed by homologous recombination by introducing into the mutant strain a nucleic acid fragment comprising 5' and 3' regions of the defective gene, but lacking the selectable marker gene, followed by selecting on the counter-selection medium. By homologous recombination, the defective gene containing the selectable marker gene is replaced with the nucleic acid fragment lacking the selectable marker gene. Other processes known in the art may also be used.

Hosts Cells and Recombinant Processes

The recombinant cells described herein may be selected from any host cell capable of ethanol fermentation. Those skilled in the art will understand that the genetic alterations, including metabolic modifications exemplified herein, may be described with reference to a suitable host organism and their corresponding metabolic reactions or a suitable source organism for desired genetic material such as genes for a desired metabolic pathway. However, given the complete genome sequencing of a wide variety of organisms and the high level of skill in the area of genomics, those skilled in the art can apply the teachings and guidance provided herein to other organisms. For example, the metabolic alterations exemplified herein can readily be applied to other species by incorporating the same or analogous encoding nucleic acid from species other than the referenced species.

The host cells for preparing the recombinant cells described herein can be from any suitable host, such as a yeast strain, including, but not limited to, a *Saccharomyces, Rhodotorula, Schizosaccharomyces, Kluyveromyces, Pichia, Hansenula, Rhodosporidium, Candida, Yarrowia, Lipomyces, Cryptococcus,* or *Dekkera* sp. cell. In particular, *Saccharomyces* host cells are contemplated, such as *Saccharomyces cerevisiae, bayanus* or *carlsbergensis* cells. Preferably, the yeast cell is a *Saccharomyces cerevisiae* cell. Suitable cells can, for example, be derived from commercially available strains and polyploid or aneuploid industrial strains, including but not limited to those from Superstart™, THERMOSACC@, C5 FUEL™, XyloFerm@, etc. (Lallemand); RED STAR and ETHANOL RED@ (Fermentis/Lesaffre); FALI (AB Mauri); Baker's Best Yeast, Baker's Compressed Yeast, etc. (Fleishmann's Yeast); BIOFERM AFT, XP, CF, and XR(North American Bioproducts Corp.); Turbo Yeast (Gert Strand AB); and FERMIOL® (DSM Specialties). Other useful yeast strains are available from biological depositories such as the American Type Culture Collection (ATCC) or the Deutsche Sammlung von Mikroorganismen und Zellkulturen GmbH (DSMZ), such as, e.g., BY4741 (e.g., ATCC 201388); Y108-1 (ATCC PTA.10567) and NRRL YB-1952 (ARS Culture Collection). Still other *S. cerevisiae* strains suitable as host cells DBY746, [Alpha][Eta]22, 5150-2B, GPY55-15Ba, CEN.PK, USM21, TMB3500, TMB3400, VTT-A-63015, VTT-A-85068, VTT-c-79093 and their derivatives as well as *Saccharomyces* sp. 1400, 424A (LNH-ST), 259A (LNH-ST) and derivatives thereof. In one embodiment, the recombinant cell is a derivative of a strain *Saccharomyces cerevisiae* CIBTS1260 (deposited under Accession No. NRRL Y-50973 at the *Agricultural Research* Service Culture Collection (NRRL), Illinois 61604 U.S.A.).

The recombinant cells described herein may utilize expression vectors comprising the coding sequence of one or more (e.g., two, several) heterologous genes linked to one or more control sequences that direct expression in a suitable cell under conditions compatible with the control sequence(s). Such expression vectors may be used in any of the cells and processes described herein. The polynucleotides described herein may be manipulated in a variety of ways to provide for expression of a desired polypeptide. Manipulation of the polynucleotide prior to its insertion into a vector may be desirable or necessary depending on the expression vector. The techniques for modifying polynucleotides utilizing recombinant DNA processes are well known in the art.

A construct or vector (or multiple constructs or vectors) comprising the one or more (e.g., two, several) heterologous genes may be introduced into a cell so that the construct or vector is maintained as a chromosomal integrant or as a self-replicating extra-chromosomal vector as described earlier.

The various nucleotide and control sequences may be joined together to produce a recombinant expression vector that may include one or more (e.g., two, several) convenient restriction sites to allow for insertion or substitution of the polynucleotide at such sites. Alternatively, the polynucleotide(s) may be expressed by inserting the polynucleotide(s) or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the cell, or a transposon, may be used.

The expression vector may contain any suitable promoter sequence that is recognized by a cell for expression of a gene described herein. The promoter sequence contains transcriptional control sequences that mediate the expression of the polypeptide. The promoter may be any polynucleotide that shows transcriptional activity in the cell of choice including mutant, truncated, and hybrid promoters, and may be obtained from genes encoding extracellular or intracellular polypeptides either homologous or heterologous to the cell.

Each heterologous polynucleotide described herein may be operably linked to a promoter that is foreign to the polynucleotide. For example, in one embodiment, the heterologous polynucleotide encoding the xylose isomerase is operably linked to a promoter foreign to the polynucleotide. The promoters may be identical to or share a high degree of sequence identity (e.g., at least about 80%, at least about 85%, at least about 90%, at least about 95%, or at least about 99%) with a selected native promoter.

Examples of suitable promoters for directing the transcription of the nucleic acid constructs in a yeast cells, include, but are not limited to, the promoters obtained from the genes for enolase, (e.g., *S. cerevisiae* enolase or *I. orientalis* enolase (ENO1)), galactokinase (e.g., *S. cerevisiae* galactokinase or *I. orientalis* galactokinase (GAL1)), alcohol dehydrogenase/glyceraldehyde-3-phosphate dehydrogenase (e.g., *S. cerevisiae* alcohol dehydrogenase/glyceraldehyde-3-phosphate dehydrogenase or *I. orientalis* alcohol dehydrogenase/glyceraldehyde-3-phosphate dehydrogenase (ADH1, ADH2/GAP)), triose phosphate isomerase (e.g., *S. cerevisiae* triose phosphate isomerase or *I. orientalis* triose phosphate isomerase (TPI)), metallothionein (e.g., *S. cerevisiae* metallothionein or *I. orientalis* metallothionein (CUP1)), 3-phosphoglycerate kinase (e.g., S. cerevisiae 3-phosphoglycerate kinase or I. orientalis 3-phosphoglycerate kinase (PGK)), PDC1, xylose reductase (XR), xylitol dehydrogenase (XDH), L-(+)-lactate-cytochrome c oxidoreductase (CYB2), translation elongation factor-1 (TEF1), translation elongation factor-2 (TEF2), glyceraldehyde-3-phosphate dehydrogenase (GAPDH), and orotidine 5'-phosphate decarboxylase (URA3) genes. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the yeast cell of choice may be used. The terminator may be identical to or share a high degree of sequence identity (e.g., at least about 80%, at least about 85%, at least about 90%, at least about 95%, or at least about 99%) with the selected native terminator.

Suitable terminators for yeast host cells may be obtained from the genes for enolase (e.g., *S. cerevisiae* or *I. orientalis* enolase cytochrome C (e.g., *S. cerevisiae* or *I. orientalis* cytochrome (CYC1)), glyceraldehyde-3-phosphate dehydrogenase (e.g., *S. cerevisiae* or *I. orientalis* glyceraldehyde-3-phosphate dehydrogenase (gpd)), PDC1, XR, XDH, transaldolase (TAL), transketolase (TKL), ribose 5-phosphate ketol-isomerase (RKI), CYB2, and the galactose family of genes (especially the GAL10 terminator). Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* crylllA gene (WO 94/25612) and a *Bacillus subtilis* SP82 gene (Hue et al., 1995, *Journal of Bacteriology* 177: 3465-3471).

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the yeast cell of choice may be used.

Suitable leaders for yeast host cells are obtained from the genes for enolase (e.g., *S. cerevisiae* or *I. orientalis* enolase (ENO-1)), 3-phosphoglycerate kinase (e.g., *S. cerevisiae* or *I. orientalis* 3-phosphoglycerate kinase), alpha-factor (e.g., *S. cerevisiae* or *I. orientalis* alpha-factor), and alcohol dehydrogenase/glyceraldehyde-3-phosphate dehydrogenase (e.g., *S. cerevisiae* or *I. orientalis* alcohol dehydrogenase/glyceraldehyde-3-phosphate dehydrogenase (ADH2/GAP)).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used. Useful polyadenylation sequences for yeast cells are described by Guo and Sherman, 1995, *Mol. Cellular Biol.* 15: 5983-5990.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used.

The vectors may contain one or more (e.g., two, several) selectable markers that permit easy selection of transformed, transfected, transduced, or the like cells. A selectable marker is a gene the product of which provides for biocide or viral resistance, resistance to heavy metals, prototrophy to auxotrophs, and the like. Suitable markers for yeast host cells include, but are not limited to, ADE2, HIS3, LEU2, LYS2, MET3, TRP1, and URA3.

The vectors may contain one or more (e.g., two, several) elements that permit integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination. Potential integration loci include those described in the art (e.g., See US2012/0135481).

For autonomous replication, the vector may further comprise an origin of replication enabling the vector to replicate autonomously in the yeast cell. The origin of replication may be any plasmid replicator mediating autonomous replication that functions in a cell. The term "origin of replication" or "plasmid replicator" means a polynucleotide that enables a plasmid or vector to replicate in vivo. Examples of origins of replication for use in a yeast host cell are the 2 micron origin of replication, ARS1, ARS4, the combination of ARS1 and CEN3, and the combination of ARS4 and CEN6.

More than one copy of a polynucleotide described herein may be inserted into a host cell to increase production of a polypeptide. An increase in the copy number of the polynucleotide can be obtained by integrating at least one additional copy of the sequence into the yeast cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors described herein are well known to one skilled in the art (see, e.g., Sambrook et al., 1989, supra).

Additional procedures and techniques known in the art for the preparation of recombinant cells for ethanol fermentation, are described in, e.g., WO2016/045569, the content of which is hereby incorporated by reference.

Processes of Ethanol Production

The recombinant cells described herein may be used for the production of ethanol. One aspect is a process for producing ethanol, comprising cultivating a recombinant cell described herein in a fermentable medium under suitable conditions to produce ethanol. In another aspect is a process for producing ethanol, comprising (a) saccharifying a cellulosic and/or starch-containing material with an enzyme composition; (b) fermenting the saccharified material of step (a) with any one of the recombinant cells described herein (e.g., a cell comprising a heterologous polynucleotide encoding a xylose isomerase described herein). In one embodiment, the process comprises recovering the ethanol from the fermentation medium.

The processing of the cellulosic and/or starch containing material can be accomplished using processes conventional in the art. Moreover, the processes of can be implemented using any conventional biomass and/or starch processing apparatus configured to carry out the processes.

Saccharification (i.e., hydrolysis) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF).

SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation organismcan tolerate. It is understood herein that any process known in the art comprising pretreatment, enzymatic hydrolysis (saccharification), fermentation, or a combination thereof, can be used in the practicing the processes described herein.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

Cellulosic Pretreatment

In one embodiment of the processes, the cellulosic material is pretreated before saccharification in step (a).

In practicing the processes described herein, any pretreatment process known in the art can be used to disrupt plant cell wall components of the cellulosic material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technology* 100:10-18; Mosier et al., 2005, *Bioresource Technology* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using processes known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

In a one embodiment, the cellulosic material is pretreated before saccharification (i.e., hydrolysis) and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

In one embodiment, the cellulosic material is pretreated with steam. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

In one embodiment, the cellulosic material is subjected to a chemical pretreatment. The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, *Bioresource Technology* 855: 1-33; Schell et al., 2004, *Bioresource Technology* 91: 179-188; Lee et al., 1999, *Adv. Biochem. Eng. Biotechnol.* 65: 93-115). In a specific embodiment the dilute acid pretreatment of cellulosic material is carried out using 4% w/w sulfuric acid at 180° C. for 5 minutes.

Several processes of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment.

Lime pretreatment is performed with calcium oxide or calcium hydroxide at temperatures of 85-150° C. and residence times from 1 hour to several days (Wyman et al., 2005, *Bioresource Technology* 96: 1959-1966; Mosier et al., 2005, *Bioresource Technology* 96: 673-686). WO2006/110891, WO2006/110899, WO2006/110900, and WO2006/110901 disclose pretreatment processes using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technology* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment process, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO2006/032282).

Ammonia fiber expansion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment processes are described by Schell et al., 2003, *Appl. Biochem. Biotechnol.* 105-108: 69-85, and Mosier et al., 2005, *Bioresource Technology* 96: 673-686, and U.S. Published Application 2002/0164730.

In one embodiment, the chemical pretreatment is carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic material and held at a temperature in the range of preferably 140-200° C., e.g., 165-190° C., for periods ranging from 1 to 60 minutes.

In another embodiment, pretreatment takes place in an aqueous slurry. In preferred aspects, the cellulosic material is present during pretreatment in amounts preferably between 10-80 wt. %, e.g., 20-70 wt. % or 30-60 wt. %, such as around 40 wt. %. The pretreated cellulosic material can be unwashed or washed using any process known in the art, e.g., washed with water.

In one embodiment, the cellulosic material is subjected to mechanical or physical pretreatment. The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in one embodiment, the cellulosic material is subjected to physical (mechanical) or chemical pretreatment, or any combination thereof, to promote the separation and/or release of cellulose, hemicellulose, and/or lignin.

In one embodiment, the cellulosic material is subjected to a biological pretreatment. The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, *Adv. Appl. Microbiol.* 39: 295-333; McMillan, J. D., 1994, Pretreating lignocellulosic biomass: a review, in Enzymatic Conversion of Biomass for Fuels Production, Himmel, M. E., Baker, J. O., and Overend, R. P., eds., *ACS Symposium Series* 566, American Chemical Society, Washington, D.C., chapter 15; Gong, C. S., Cao, N. J., Du, J., and Tsao, G. T., 1999, Ethanol production from renewable resources, in Advances in Biochemical Engineering/Biotechnology, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Saccharification

In the saccharification step (a) (i.e., hydrolysis step), the cellulosic and/or starch-containing material, e.g., pretreated, is hydrolyzed to break down cellulose, hemicellulose, and/or starch to fermentable sugars, such as glucose, cellobiose, xylose, xylulose, arabinose, mannose, galactose, and/or soluble oligosaccharides. The hydrolysis is performed enzymatically e.g., by a cellulolytic enzyme composition. The enzymes of the compositions can be added simultaneously or sequentially.

Enzymatic hydrolysis may be carried out in a suitable aqueous environment under conditions that can be readily determined by one skilled in the art. In one aspect, hydrolysis is performed under conditions suitable for the activity of the enzymes(s), i.e., optimal for the enzyme(s). The hydrolysis can be carried out as a fed batch or continuous process where the cellulosic and/or starch-containing material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 4.5 to about 5.5. The dry solids content is in the range of preferably about 5 to about 50 wt. %, e.g., about 10 to about 40 wt. % or about 20 to about 30 wt. %.

Saccharification in step (a) may be carried out using a cellulolytic enzyme composition. Such enzyme compositions are described below in the "Cellulolytic Enzyme Composition"-section below. The cellulolytic enzyme compositions can comprise any protein useful in degrading the cellulosic material. In one aspect, the cellulolytic enzyme composition comprises or further comprises one or more (e.g., several) proteins selected from the group consisting of a cellulase, an AA9 (GH61) polypeptide, a hemicellulase, an esterase, an expansin, a ligninolytic enzyme, an oxidoreductase, a pectinase, a protease, and a swollenin.

In another embodiment, the cellulase is preferably one or more (e.g., several) enzymes selected from the group consisting of an endoglucanase, a cellobiohydrolase, and a beta-glucosidase.

In another embodiment, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another embodiment, the oxidoreductase is one or more (e.g., several) enzymes selected from the group consisting of a catalase, a laccase, and a peroxidase.

The enzymes or enzyme compositions used in a processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

In one embodiment, an effective amount of cellulolytic or hemicellulolytic enzyme composition to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In one embodiment, such a compound is added at a molar ratio of the compound to glucosyl units of cellulose of about $10^{-6}$ to about 10, e.g., about $10^{-6}$ to about 7.5, about $10^{-6}$ to about 5, about $10^{-5}$ to about 2.5, about $10^{-5}$ to about 1, about $10^{-5}$ to about 1, about $10^{8}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described in WO2012/021401, and the soluble contents thereof. A liquor for cellulolytic enhancement of an AA9 polypeptide (GH61 polypeptide) can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and an AA9 polypeptide during hydrolysis of a cellulosic substrate by a cellulolytic enzyme composition. The liquor can be separated from the treated material using a process standard in the art, such as filtration, sedimentation, or centrifugation.

In one embodiment, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{1}$ to about $10^{-1}$ g, about $10^{-4}$ to about $10^{-1}$ g, about $10^{3}$ to about $10^{-1}$ g, or about $10^{3}$ to about $10^{2}$ g per g of cellulose.

Cellulolytic Enzyme Composition

A cellulolytic enzyme composition may be present or added during saccharification in step (a). A cellulolytic enzyme composition is an enzyme preparation containing one or more (e.g., several) cellulolytic enzymes. Such enzymes include endoglucanase, cellobiohydrolase, beta-glucosidase, and/or combinations thereof.

The cellulolytic enzyme composition may be of any origin. In an embodiment the cellulolytic enzyme composition is derived from a strain of *Trichoderma*, such as a strain of *Trichoderma reesei*; a strain of *Humicola*, such as a strain of *Humicola insolens*, and/or a strain of *Chrysosporium*, such as a strain of *Chrysosporium lucknowense*. In a preferred embodiment the cellulolytic enzyme composition is derived from a strain of *Trichoderma reesei*.

The cellulolytic enzyme composition may further comprise one or more of the following polypeptides, such as enzymes: AA9 polypeptide (GH61 polypeptide) having cellulolytic enhancing activity, beta-glucosidase, xylanase, beta-xylosidase, CBH I, CBH II, or a mixture of two, three, four, five or six thereof.

The further polypeptide(s) (e.g., AA9 polypeptide) and/or enzyme(s) (e.g., beta-glucosidase, xylanase, beta-xylosidase, CBH I and/or CBH II may be foreign to the cellulolytic enzyme composition producing organism (e.g., *Trichoderma reesei*).

In an embodiment the cellulolytic enzyme composition comprises an AA9 polypeptide having cellulolytic enhancing activity and a beta-glucosidase.

In another embodiment the cellulolytic enzyme composition comprises an AA9 polypeptide having cellulolytic enhancing activity, a beta-glucosidase, and a CBH I.

In another embodiment the cellulolytic enzyme composition comprises an AA9 polypeptide having cellulolytic enhancing activity, a beta-glucosidase, a CBH I and a CBH II.

Other enzymes, such as endoglucanases, may also be comprised in the cellulolytic enzyme composition.

As mentioned above the cellulolytic enzyme composition may comprise a number of difference polypeptides, including enzymes.

In one embodiment, the cellulolytic enzyme composition is a *Trichoderma reesei* cellulolytic enzyme composition, further comprising *Thermoascus aurantiacus* AA9 (GH61A) polypeptide having cellulolytic enhancing activity (e.g., WO2005/074656), and *Aspergillus oryzae* beta-glucosidase fusion protein (e.g., one disclosed in WO2008/057637, in particular shown as SEQ ID NOs: 59 and 60).

In another embodiment the cellulolytic enzyme composition is a *Trichoderma reesei* cellulolytic enzyme composition, further comprising *Thermoascus aurantiacus* AA9 (GH61A) polypeptide having cellulolytic enhancing activity (e.g., SEQ ID NO: 2 in WO2005/074656), and *Aspergillus fumigatus* beta-glucosidase (e.g., SEQ ID NO: 2 of WO2005/047499).

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO2011/041397, and *Aspergillus fumigatus* beta-glucosidase (e.g., SEQ ID NO: 2 of WO2005/047499).

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO2011/041397, and *Aspergillus fumigatus* beta-glucosidase (e.g., SEQ ID NO: 2 of WO2005/047499) or a variant disclosed in WO2012/044915 (hereby incorporated by reference), in particular one comprising one or more such as all of the following substitutions: F100D, S283G, N456E, F512Y.

In an embodiment the cellulolytic enzyme composition is a *Trichoderma reesei* cellulolytic composition, further comprising an AA9 (GH61A) polypeptide having cellulolytic enhancing activity, in particular the one derived from a strain of *Penicillium emersonii* (e.g., SEQ ID NO: 2 in WO2011/041397), *Aspergillus fumigatus* beta-glucosidase (e.g., SEQ ID NO: 2 in WO2005/047499) variant with one or more, in particular all of the following substitutions: F100D, S283G, N456E, F512Y and disclosed in WO2012/044915; *Aspergillus fumigatus* Cel7A CBH1, e.g., the one disclosed as SEQ ID NO: 6 in WO2011/057140 and *Aspergillus fumigatus* CBH II, e.g., the one disclosed as SEQ ID NO: 18 in WO2011/057140.

In a preferred embodiment the cellulolytic enzyme composition is a *Trichoderma reesei*, cellulolytic enzyme composition, further comprising a hemicellulase or hemicellulolytic enzyme composition, such as an *Aspergillus fumigatus* xylanase and *Aspergillus fumigatus* beta-xylosidase.

In an embodiment the cellulolytic enzyme composition also comprises a xylanase (e.g., derived from a strain of the genus *Aspergillus*, in particular *Aspergillus aculeatus* or *Aspergillus fumigatus*; or a strain of the genus *Talaromyces*, in particular *Talaromyces leycettanus*) and/or a beta-xylosidase (e.g., derived from *Aspergillus*, in particular *Aspergillus fumigatus*, or a strain of *Talaromyces*, in particular *Talaromyces emersonii*).

In an embodiment the cellulolytic enzyme composition is a *Trichoderma reesei* cellulolytic enzyme composition, further comprising *Thermoascus aurantiacus* AA9 (GH61A) polypeptide having cellulolytic enhancing activity (e.g., WO2005/074656), *Aspergillus oryzae* beta-glucosidase fusion protein (e.g., one disclosed in WO2008/057637, in particular as SEQ ID NOs: 59 and 60), and *Aspergillus aculeatus* xylanase (e.g., Xyl II in WO 94/21785).

In another embodiment the cellulolytic enzyme composition comprises a *Trichoderma reesei* cellulolytic preparation, further comprising *Thermoascus aurantiacus* GH61A polypeptide having cellulolytic enhancing activity (e.g., SEQ ID NO: 2 in WO2005/074656), *Aspergillus fumigatus* beta-glucosidase (e.g., SEQ ID NO: 2 of WO2005/047499) and *Aspergillus aculeatus* xylanase (Xyl II disclosed in WO 94/21785).

In another embodiment the cellulolytic enzyme composition is a *Trichoderma reesei* cellulolytic enzyme composition, further comprising *Thermoascus aurantiacus* AA9 (GH61A) polypeptide having cellulolytic enhancing activity (e.g., SEQ ID NO: 2 in WO2005/074656), *Aspergillus fumigatus* beta-glucosidase (e.g., SEQ ID NO: 2 of WO2005/047499) and *Aspergillus aculeatus* xylanase (e.g., Xyl II disclosed in WO 94/21785).

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO2011/041397, *Aspergillus fumigatus* beta-glucosidase (e.g., SEQ ID NO: 2 of WO2005/047499) and *Aspergillus fumigatus* xylanase (e.g., Xyl III in WO2006/078256).

In another embodiment the cellulolytic enzyme composition comprises a *Trichoderma reesei* cellulolytic enzyme composition, further comprising *Penicillium emersonii* AA9 (GH61A) polypeptide having cellulolytic enhancing activity, in particular the one disclosed in WO2011/041397, *Aspergillus fumigatus* beta-glucosidase (e.g., SEQ ID NO: 2 of WO2005/047499), *Aspergillus fumigatus* xylanase (e.g., Xyl III in WO2006/078256), and CBH I from *Aspergillus fumigatus*, in particular Cel7A CBH1 disclosed as SEQ ID NO: 2 in WO2011/057140.

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO2011/041397, *Aspergillus fumigatus* beta-glucosidase (e.g., SEQ ID NO: 2 of WO2005/047499), *Aspergillus fumigatus* xylanase (e.g., Xyl III in WO2006/078256), CBH I from *Aspergillus fumigatus*, in particular Cel7A CBH1 disclosed as SEQ ID NO: 2 in WO2011/057140, and CBH II derived from *Aspergillus fumigatus* in particular the one disclosed as SEQ ID NO: 4 in WO2013/028928.

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO2011/041397, *Aspergillus fumigatus* beta-glucosidase (e.g., SEQ ID NO: 2 of WO2005/047499) or variant thereof with one or more, in particular all, of the following substitutions: F100D, S283G, N456E, F512Y; *Aspergillus fumigatus* xylanase (e.g., Xyl III in WO2006/078256), CBH I from *Aspergillus fumigatus*, in particular Cel7A CBH I disclosed as SEQ ID NO: 2 in WO2011/057140, and CBH II derived from *Aspergillus fumigatus*, in particular the one disclosed in WO2013/028928.

In another embodiment the cellulolytic enzyme composition is a *Trichoderma reesei* cellulolytic enzyme composition comprising the CBH I (GENSEQP Accession No. AZY49536 (WO2012/103293); a CBH II (GENSEQP Accession No. AZY49446 (WO2012/103288); a beta-glucosidase variant (GENSEQP Accession No. AZU67153 (WO2012/44915)), in particular with one or more, in particular all, of the following substitutions: F100D, S283G, N456E, F512Y; and AA9 (GH61 polypeptide) (GENSEQP Accession No. BAL61510 (WO2013/028912)).

In another embodiment the cellulolytic enzyme composition is a *Trichoderma reesei* cellulolytic enzyme composition comprising a CBH I (GENSEQP Accession No. AZY49536 (WO2012/103293)); a CBH II (GENSEQP Accession No. AZY49446 (WO2012/103288); a GH10 xylanase (GENSEQP Accession No. BAK46118 (WO2013/019827)); and a beta-xylosidase (GENSEQP Accession No. AZI04896 (WO2011/057140)).

In another embodiment the cellulolytic enzyme composition is a *Trichoderma reesei* cellulolytic enzyme composition comprising a CBH I (GENSEQP Accession No. AZY49536 (WO2012/103293)); a CBH II (GENSEQP Accession No. AZY49446 (WO2012/103288)); and an AA9 (GH61 polypeptide; GENSEQP Accession No. BAL61510 (WO2013/028912)).

In another embodiment the cellulolytic enzyme composition is a *Trichoderma reesei* cellulolytic enzyme composition comprising a CBH I (GENSEQP Accession No. AZY49536 (WO2012/103293)); a CBH II (GENSEQP Accession No. AZY49446 (WO2012/103288)), an AA9 (GH61 polypeptide; GENSEQP Accession No. BAL61510 (WO2013/028912)), and a catalase (GENSEQP Accession No. BAC11005 (WO02012/130120)).

In an embodiment the cellulolytic enzyme composition is a *Trichoderma reesei* cellulolytic enzyme composition comprising a CBH I (GENSEQP Accession No. AZY49446 (WO2012/103288); a CBH II (GENSEQP Accession No. AZY49446 (WO2012/103288)), a beta-glucosidase variant (GENSEQP Accession No. AZU67153 (WO2012/44915)), with one or more, in particular all, of the following substitutions: F100D, S283G, N456E, F512Y; an AA9 (GH61 polypeptide; GENSEQP Accession No. BAL61510 (WO2013/028912)), a GH10 xylanase (GENSEQP Accession No. BAK46118 (WO2013/019827)), and a beta-xylosidase (GENSEQP Accession No. AZI04896 (WO2011/057140)).

In an embodiment the cellulolytic composition is a *Trichoderma reesei* cellulolytic enzyme composition comprising an EG I(Swissprot Accession No. P07981), EG II (EMBL Accession No. M19373), CBH I (supra); CBH II (supra); beta-glucosidase variant (supra) with the following substitutions: F100D, S283G, N456E, F512Y; an AA9 (GH61 polypeptide; supra), GH10 xylanase (supra); and beta-xylosidase (supra).

All cellulolytic enzyme compositions disclosed in WO2013/028928 are also contemplated and hereby incorporated by reference.

The cellulolytic enzyme composition comprises or may further comprise one or more (several) proteins selected from the group consisting of a cellulase, a AA9 (i.e., GH61) polypeptide having cellulolytic enhancing activity, a hemicellulase, an expansin, an esterase, a laccase, a ligninolytic enzyme, a pectinase, a peroxidase, a protease, and a swollenin.

In one embodiment the cellulolytic enzyme composition is a commercial cellulolytic enzyme composition. Examples of commercial cellulolytic enzyme compositions suitable for use in a process of the invention include: CELLIC@ CTec (Novozymes A/S), CELLIC@ CTec2 (Novozymes A/S), CELLIC@ CTec3 (Novozymes A/S), CELLUCLAST™ (Novozymes A/S), SPEZYME™ CP(Genencor Int.), ACCELLERASE™ 1000, ACCELLERASE 1500, ACCELLERASE™ TRIO (DuPont), FILTRASE® NL (DSM); METHAPLUS@ S/L 100 (DSM), ROHAMENT™ 7069 W(Röhm GmbH), or ALTERNAFUEL® CMAX3™ (Dyadic International, Inc.). The cellulolytic enzyme composition may be added in an amount effective from about 0.001 to about 5.0 wt. % of solids, e.g., about 0.025 to about 4.0 wt. % of solids or about 0.005 to about 2.0 wt. % of solids.

Additional enzymes, and compositions thereof can be found in WO2016/0455569 (the content of which is incorporated herein in its entirety).

Fermentation

The fermentable sugars obtained from the hydrolyzed cellulosic and/or starch-containing material can be fermented by one or more (e.g., several) fermenting microorganisms described herein capable of fermenting the sugars directly or indirectly into ethanol. "Fermentation" or "fermentation process" refers to any fermentation process or any process comprising a fermentation step.

In the fermentation step, sugars, released from the cellulosic and/or starch-containing material, e.g., as a result of the pretreatment and enzymatic hydrolysis steps, are fermented to ethanol, by a fermenting organism, such as yeast described herein. Hydrolysis (saccharification) and fermentation can be separate or simultaneous.

Any suitable hydrolyzed cellulosic and/or starch containing material can be used in the fermentation step in practicing the processes described herein. Such feedstocks include, but are not limited to carbohydrates (e.g., lignocellulose, xylans, cellulose, starch, etc.). The material is generally selected based on economics, i.e., costs per equivalent sugar potential, and recalcitrance to enzymatic conversion.

Production of ethanol by a fermenting microorganism using cellulosic material results from the metabolism of sugars (monosaccharides). The sugar composition of the hydrolyzed cellulosic material and the ability of the fermenting microorganism to utilize the different sugars has a direct impact in process yields. Prior to Applicant's disclosure herein, strains known in the art utilize glucose efficiently but do not (or very limitedly) metabolize pentoses like xylose, a monosaccharide commonly found in hydrolyzed material.

Compositions of the fermentation media and fermentation conditions depend on the fermenting organism and can easily be determined by one skilled in the art. Typically, the fermentation takes place under conditions known to be suitable for generating the fermentation product. In some embodiments, the fermentation process is carried out under aerobic or microaerophilic (i.e., where the concentration of oxygen is less than that in air), or anaerobic conditions. In some embodiments, fermentation is conducted under anaerobic conditions (i.e., no detectable oxygen), or less than about 5, about 2.5, or about 1 mmol/L/h oxygen. In the absence of oxygen, the NADH produced in glycolysis cannot be oxidized by oxidative phosphorylation. Under anaerobic conditions, pyruvate or a derivative thereof may be utilized by the host cell as an electron and hydrogen acceptor in order to generate NAD+.

The fermentation process is typically run at a temperature that is optimal for the recombinant fungal cell. For example, in some embodiments, the fermentation process is performed at a temperature in the range of from about 25° C. to about 42° C. Typically the process is carried out a temperature that is less than about 38° C., less than about 35° C., less than about 33° C., or less than about 38° C., but at least about 20° C., 22° C., or 25° C.

A fermentation stimulator can be used in a process described herein to further improve the fermentation, and in particular, the performance of the fermenting organism, such as, rate enhancement and product yield (e.g., ethanol yield). A "fermentation stimulator" refers to stimulators for growth of the fermenting organisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

The fermentation product, i.e., ethanol, can optionally be recovered from the fermentation medium using any process known in the art including, but not limited to, chromatography, electrophoretic procedures, differential solubility, distillation, or extraction. For example, alcohol is separated from the fermented cellulosic material and purified by conventional processes of distillation. Ethanol with a purity of up to about 96 vol. % can be obtained, which can be used as, for example, fuel ethanol, drinking ethanol, i.e., potable neutral spirits, or industrial ethanol.

In some aspects of the processes, the ethanol after being recovered is substantially pure. With respect to the processes of producing ethanol, "substantially pure" intends a recovered preparation that contains no more than 15% impurity, wherein impurity intends compounds other than ethanol. In one variation, a substantially pure preparation is provided wherein the preparation contains no more than 25% impurity, or no more than 20% impurity, or no more than 10% impurity, or no more than 5% impurity, or no more than 3% impurity, or no more than 1% impurity, or no more than 0.5% impurity.

In some embodiments of the processes described herein, fermentation of step (b) consumes an increased amount of pentose (e.g., xylose) when compared to fermentation using an identical cell without the heterologous polynucleotide encoding a xylose isomerase under the same conditions (e.g., at about or after 10, 20, 30, 40, 50, 60, or 70 hours fermentation, such as using the conditions described herein).

In one embodiment of the processes described herein, more than 65%, e.g., at least 70%, 75%, 80%, 85%, 90%, 95% of xylose in the medium is consumed at about or after 10, 20, 30, 40, 50, 60, or 70 hours fermentation (e.g., under conditions described herein).

In one embodiment of the processes described herein, more than 65%, e.g., at least 70%, 75%, 80%, 85%, 90%, 95% of glucose in the medium is consumed at about or after 10, 20, 30, 40, 50, 60, or 70 hours fermentation (e.g., under conditions described herein).

In one embodiment of the processes described herein, more than 65%, e.g., at least 70%, 75%, 80%, 85%, 90%, 95% of pentose (e.g., xylose) in the medium is consumed, and more than 65%, e.g., at least 70%, 75%, 80%, 85%, 90%, 95% of glucose in the medium is consumed at about or after 10, 20, 30, 40, 50, 60, or 70 hours fermentation (e.g., under conditions described herein).

In some embodiments of the processes described herein, fermentation of step (b) provides higher ethanol yield when compared to fermentation using an identical cell without the heterologous polynucleotide encoding a xylose isomerase under the same conditions (e.g., at about or after 10, 20, 30, 40, 50, 60, or 70 hours fermentation, such as under conditions described herein).

Suitable assays to test for the production of ethanol and contaminants, and sugar consumption can be performed using processes known in the art. For example, ethanol product, as well as other organic compounds, can be analyzed by processes such as HPLC (High Performance Liquid Chromatography), GC-MS (Gas Chromatography Mass Spectroscopy) and LC-MS (Liquid Chromatography-Mass Spectroscopy) or other suitable analytical processes using routine procedures well known in the art. The release of ethanol in the fermentation broth can also be tested with the culture supernatant. Byproducts and residual sugar in the fermentation medium (e.g., glucose or xylose) can be quantified by HPLC using, for example, a refractive index detector for glucose and alcohols, and a UV detector for organic acids (Lin et al., *Biotechnol. Bioeng.* 90:775-779 (2005)), or using other suitable assay and detection processes well known in the art.

The invention may further be described in the following numbered paragraphs:

Paragraph [1]: A recombinant yeast cell comprising a heterologous polynucleotide encoding a polypeptide having at least 60%, e.g., at least 65%, 70%, 75%, 80%, 85%, 90%, 95%, 97%, 98%, 99%, or 100% sequence identity to SEQ ID NO: 22; and wherein the polypeptide has xylose isomerase activity.

Paragraph [2]: The recombinant cell of paragraph [1], wherein the heterologous polynucleotide encodes a polypeptide that differs by no more than ten amino acids, e.g., by no more than five amino acids, by no more than four amino acids, by no more than three amino acids, by no more than two amino acids, or by one amino acid from SEQ ID NO: 22.

Paragraph [3]: The recombinant cell of paragraph [1], wherein the heterologous polynucleotide encodes a polypeptide having an amino acid sequence comprising or consisting of the amino acid sequence of SEQ ID NO: 22.

Paragraph [4]: The recombinant cell of any one of paragraphs [1]-[3], wherein the heterologous polynucleotide comprises a coding sequence having at least 60%, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 21.

Paragraph [5]: The recombinant cell of paragraph [4], wherein the heterologous polynucleotide has a coding sequence that consists of SEQ ID NO: 21.

Paragraph [6]: The recombinant cell of any one of paragraphs [1]-[5], wherein the heterologous polynucleotide comprises a coding sequence that hybridizes under at least low stringency conditions e.g., medium stringency conditions, medium-high stringency conditions, high stringency conditions, or very high stringency conditions with the full-length complementary strand of SEQ ID NO: 21.

Paragraph [7]: The recombinant cell of any one of paragraphs [1]-[6], further comprising a heterologous polynucleotide encoding a xylulokinase (XK).

Paragraph [8]: The recombinant cell of paragraph [7] wherein the xylulokinase (XK) is a *Saccharomyces cerevisiae* XK, or an XK having at least 60%, e.g., at least 65%, 70%, 75%, 80%, 85%, 90%, 95%, 97%, 98%, 99%, or 100% sequence identity to SEQ ID NO: 25.

Paragraph [9]: The recombinant cell of any one of paragraphs [1]-[8], further comprising a heterologous polynucleotide encoding a hexose transporter (e.g., HXT1, HXT2, HXT3, HXT4, HXT5, HXT6, HXT7, or GAL2).

Paragraph [10]: The recombinant cell of paragraph [9], wherein the hexose transporter has at least 60%, e.g., at least 65%, 70%, 75%, 80%, 85%, 90%, 95%, 97%, 98%, 99%, or 100% sequence identity to SEQ ID NO: 26.

Paragraph [11]: The recombinant cell of any one of paragraphs [1]-[10], further comprising a heterologous polynucleotide encoding a ribulose 5 phosphate 3-epimerase (RPE1).

Paragraph [12]: The recombinant cell of paragraph [11], wherein the ribulose 5 phosphate 3-epimerase (RPE1) is a *Saccharomyces cerevisiae* RPE1, or an RPE1 having at least 60%, e.g., at least 65%, 70%, 75%, 80%, 85%, 90%, 95%, 97%, 98%, 99%, or 100% sequence identity to a *Saccharomyces cerevisiae* RPE1.

Paragraph [13]: The recombinant cell of any one of paragraphs [1]-[12], further comprising a heterologous polynucleotide encoding a ribulose 5 phosphate isomerase (RKI1).

Paragraph [14]: The recombinant cell of paragraph [13], wherein the ribulose 5 phosphate isomerase (RKI1) is a *Saccharomyces cerevisiae* RKI1, or an RKI1 having at least 60%, e.g., at least 65%, 70%, 75%, 80%, 85%, 90%, 95%, 97%, 98%, 99%, or 100% sequence identity to a *Saccharomyces cerevisiae* RKI 1.

Paragraph [15]: The recombinant cell of any one of paragraphs [1]-[14], further comprising a heterologous polynucleotide encoding a transketolase (TKL1).

Paragraph [16]: The recombinant cell of paragraph [15], wherein the transketolase (TKL1) is a *Saccharomyces cerevisiae* TKL1, or an TKL1 having at least 60%, e.g., at least 65%, 70%, 75%, 80%, 85%, 90%, 95%, 97%, 98%, 99%, or 100% sequence identity to a *Saccharomyces cerevisiae* TKL1.

Paragraph [17]: The recombinant cell of any one of paragraphs [1]-[16], further comprising a heterologous polynucleotide encoding a transaldolase (TAL1).

Paragraph [18]: The recombinant cell of paragraph [17], wherein the transaldolase (TAL1) is a *Saccharomyces cerevisiae* TAL1, or an TAL1 having at least 60%, e.g., at least 65%, 70%, 75%, 80%, 85%, 90%, 95%, 97%, 98%, 99%, or 100% sequence identity to a *Saccharomyces cerevisiae* TAL1.

Paragraph [19]: The recombinant cell of any one of paragraphs [1]-[18], further comprise a disruption to an endogenous gene encoding a glycerol 3-phosphate dehydrogenase (GPD).

Paragraph [20]: The recombinant cell of any one of paragraphs [1]-[19], further comprise a disruption to an endogenous gene encoding a glycerol 3-phosphatase (GPP).

Paragraph [21]: The recombinant cell of any one of paragraphs [1]-[19], further comprise a disruption to an endogenous gene encoding an aldose reductase (e.g., GRE3 or YPR1).

Paragraph [22]: The recombinant cell of any one of paragraphs [1]-[21], which is a *Saccharomyces, Rhodotorula, Schizosaccharomyces, Kluyveromyces, Pichia, Hansenula, Rhodosporidium, Candida, Yarrowia, Lipomyces, Cryptococcus*, or *Dekkera* sp. cell.

Paragraph [23]: The recombinant cell of any one of paragraphs [1]-[22], which is a *Saccharomyces cerevisiae* cell.

Paragraph [24]: The recombinant cell of any one of paragraphs [1]-[23], wherein the cell is capable of growing on xylose (e.g., under conditions described herein).

Paragraph [25]: The recombinant cell of any one of paragraphs [1]-[24], wherein the recombinant cell has a higher growth rate on a pentose (e.g., xylose) compared to the same cell without the heterologous polynucleotide encoding a xylose isomerase (e.g., under conditions described in herein).

Paragraph [26]: The recombinant cell of any one of paragraphs [1]-[25], wherein the strain has a higher pentose (e.g., xylose) consumption compared to the same cell without the heterologous polynucleotide encoding a xylose isomerase (e.g., under conditions described herein).

Paragraph [27]: The recombinant cell of any one of paragraphs [1]-[26], wherein the strain has a higher ethanol production compared to the same cell without the heterologous polynucleotide encoding a xylose isomerase (e.g., under conditions described herein).

Paragraph [28]: A process for producing ethanol, comprising cultivating the recombinant cell of any one of paragraphs [1]-[27] in a fermentable medium under suitable conditions to produce ethanol.

Paragraph [29]: The process of paragraph [28], wherein cultivation is conducted under low oxygen (e.g., anaerobic) conditions.

Paragraph [30]: The process of paragraph [28] or [29], wherein an increased amount of pentose (e.g., xylose) is consumed when compared to the process using an identical cell without the heterologous polynucleotide encoding a xylose under the same conditions (e.g., under conditions described herein).

Paragraph [31]: The process of any one of paragraphs [28]-[30], wherein the process results in higher ethanol yield when compared to the process using an identical cell without the heterologous polynucleotide encoding a xylose isomerase under the same conditions (e.g., under conditions described herein).

Paragraph [32]: The process of any one of paragraphs [28]-[31], comprising recovering the fermentation product from the fermentation.

Paragraph [33]: The process of any one of paragraphs [28]-[32], comprising saccharifying a cellulosic and/or starch-containing material with an enzyme composition to produce the fermentable medium.

Paragraph [34]: The process of paragraph [33], wherein saccharification occurs on a cellulosic material, and wherein the cellulosic material is pretreated.

Paragraph [35]: The process of paragraph [34], wherein the pretreatment is a dilute acid pretreatment.

Paragraph [36]: The process of any one of paragraphs [33]-[35], wherein saccharification occurs on a cellulosic material, and wherein the enzyme composition comprises one or more enzymes selected from a cellulase, an AA9 polypeptide, a hemicellulase, a CIP, an esterase, an expansin, a ligninolytic enzyme, an oxidoreductase, a pectinase, a protease, and a swollenin.

Paragraph [37]: The process of paragraph [36], wherein the cellulase is one or more enzymes selected from an endoglucanase, a cellobiohydrolase, and a beta-glucosidase.

Paragraph [38]: The process of paragraph [36] or [37], wherein the hemicellulase is one or more enzymes selected a xylanase, an acetylxylan esterase, a feruloyl esterase, an arabinofuranosidase, a xylosidase, and a glucuronidase.

Paragraph [39]: The process of any of paragraphs [33]-[38], wherein fermentation and saccharification are performed simultaneously in a simultaneous saccharification and fermentation (SSF).

Paragraph [40]: The process of any of paragraphs [33]-[38], wherein fermentation and saccharification are performed sequentially (SHF).

The invention described and claimed herein is not to be limited in scope by the specific aspects herein disclosed, since these aspects are intended as illustrations of several aspects of the invention. Any equivalent aspects are intended to be within the scope of this invention.

Indeed, various modifications of the invention in addition to those shown and described herein will become apparent to those skilled in the art from the foregoing description. Such modifications are also intended to fall within the scope of the appended claims. In the case of conflict, the present disclosure including definitions will control. All references are specifically incorporated by reference for that which is described.

The following examples are offered to illustrate certain aspects of the present invention, but not in any way intended to limit the scope of the invention as claimed.

EXAMPLES

Materials and Processes

Chemicals used as buffers and substrates were commercial products of at least reagent grade.

Strains

Ethanol Red® is an industrial *Saccharomyces cerevisiae* yeast strain available from Fermentis/Lesaffre, USA and was sporulated according to the process of Herskowitz (1988) to generate haploids. Two of the haploids, YGT40 and YGT44, were used as a template for PCR amplification of several of the elements present on the plasmids in this application. Strain *S. cerevisiae* JG169 (WO2008/008967) was used as a template for amplification of the DNA fragments used for assembly of pFYD511.

Media and Solutions

LB+amp medium was composed of 10 g tryptone, 5 g yeast extract, 10 g NaCl, deionized water to 1 L and 100 mg/l ampicillin. For LB+amp agar plates, 15 g/L bacto agar was used and the concentration of ampicillin was increased to 150 mg/L.

LB+aDramvcin was used for selection of the full 2-micron plasmids in *E. coli*. Apramycin was used at a concentration of 35 mg/L for both plates and liquid cultures.

YPD medium was composed of 10 g yeast extract, 20 g peptone, 20 g glucose and deionized water to 1 L. For plates, 20 g/L bacto agar was used. ClonNat, Geneticin (G418), hygromycin B and Zeocin were added to 100 mg/L, 200 mg/L, 300 mg/L and 200 mg/L, respectively, where appropriate.

2×YPD medium was composed of 20 g yeast extract, 40 g peptone, 40 g glucose and deionized water to 1 L.

1 M $K_2HPO_4$ buffer was composed of 228.23 g $K_2HPO_4 \times 3$ $H_2O$ and deionized water to 1 L.

1 M $KH_2PO_4$ buffer was composed of 136.09 g $KH_2PO_4$ and deionized water to 1 L.

1 M phosphate buffer (pH=6.0) was composed of 150 mL of 1 M $K_2HPO_4$ and 900 mL of 1 M of $KH_2PO_4$.

SC-ura medium was composed of 6.7 g yeast nitrogen base without amino acids, 0.192 g Yeast Synthetic Drop-out Medium Supplements without uracil, 100 mL 1 M phosphate buffer (pH=6.0), 20 g glucose and deionized water to 1 L. For plates, 20 g/L bacto agar was added.

SD medium was composed of 3.35 g yeast nitrogen base without amino acids, 50 mL 1M phosphate buffer (pH=6.0), 50 mL 20% glucose and 400 mL deionized water.

SD plate medium was composed of 10 g agar with 350 mL deionized water added, then autoclaved 15 min at 121° C. After this was added 50 mL of a 20% glucose, 50 mL 1M phosphate buffer and 50 mL of a 10× stock of yeast nitrogen base (w/o amino acids).

SG medium was composed of 6.7 g yeast nitrogen base without amino acids, 100 mL 1M phosphate buffer (pH=6.0), 20 g galactose and deionized water to 1 L. For plates, 20 g/L bacto agar was added.

SX2 medium was composed of 3.35 g yeast nitrogen base without amino acids, 50 mL 1M phosphate buffer (pH=6.0), 10 g xylose (BioUltra, Sigma-Aldrich) and deionized water to 0.5 L.

SX2 plate medium was composed of 10 g agar with 350 mL deionized water added, then autoclaved 15 min at 121° C. After this was added 100 mL of a 10% xylose, 50 mL 1M phosphate buffer and 50 mL of a 10× stock of yeast nitrogen base (w/o amino acids).

TBE buffer was composed of 10.8 g of Tris base, 5.5 g of boric acid, 4 mL of 0.5 M EDTA pH=8.0, and deionized water to 1 L.

TABLE 1

Primers sequences used in the Examples.

| Identifier | SEQ ID NO: | Sequence (5'-3') |
|---|---|---|
| OY60 | 27 | AGCAACAATTCTGGAAGCCTC |
| OY61 | 28 | CAGAAGCACGCTTATCGCTC |

TABLE 1-continued

Primers sequences used in the Examples.

| Identifier | SEQ ID NO: | Sequence (5'-3') |
|---|---|---|
| OY74 | 29 | AAGAGTGGTACCCATTTTGTAATTAAAACTTAGATTAGATTGCTATG |
| OY76 | 30 | ATGGGTACCACTCTTGACGA |
| OY77 | 31 | GATTAGGGGCAGGGCAT |
| OY80 | 32 | GCCCTGCCCCTAATCGAAAGGGAACCTTTTACAAC |
| OY95 | 33 | TTTCCATCGAGCATACCATGGATAACTTCGTATAGCATACATTATACGAAGTTATGGATCCCCCACAAGTGAT |
| OY96 | 34 | CAGCGCACGCGCTAGGCCGGCCATAACTTCGTATAGCATACATTATACGAAGTTATGCCCATATTTAGCTCGTTTG |
| OY198 | 181 | GCTAGCGCTCTTCGATACTTC |
| OY199 | 182 | GATCTTGCTCTTCGACTATACAAATG |
| OY239 | 183 | ATAAACAAGGTACCTCAGTACTGACAATAAAA |
| OY240 | 184 | GCGTTTAAACGAATTCGGGCGCGCCGA |
| OY241 | 185 | GCTTAATTAAAAGCTGTTTATCTCTAGTATTACTCTTTAGACAAAAAATTGT |
| OY242 | 186 | AGGTACCTTGTTTATGTTCGGATGTGATGT |
| OY608 | 35 | ATACGAAGTTATTTAATTAAAGCTTGCCTTGTCCCCGCCGGGTCACCCGG |
| OY614 | 36 | TATAGGTATTTGAAGTCGTCATGGTTGTTTATGTTCGGATGTGATGTGAGAAC |
| OY615 | 37 | CATCCGAACATAAACAACCATGACGACTTCAAATACCTATAAGTTCTATC |
| OY616 | 38 | TCTTTTTATTGTCAGTACTGATTAGACTAAGTTCAGAACCGTTACTTTTTCCC |
| OY617 | 39 | GGTTCTGAACTTAGTCTAATCAGTACTGACAATAAAAAGATTCTTGTTTTC |
| OY618 | 40 | CATCCGAACATAAACAACCATGACAAAACAATACAAAAACTACGTTAATG |
| OY619 | 41 | TTTTGTATTGTTTTGTCATGGTTGTTTATGTTCGGATGTGATGTGAGAAC |
| OY620 | 42 | GTCTTTGACATAAAGTGATCAGTACTGACAATAAAAGATTCTTGTTTTC |
| OY621 | 43 | TCTTTTTATTGTCAGTACTGATCACTTTATGTCAAAGACAACACTTTTCAC |
| OY633 | 44 | GCTGCGGCCGGCGCGCCGCGATCGCTCGACACTGGATGGCGGCG |
| OY710 | 45 | TTCGAGAGAATCACGGCGCGGACCTTAATACATTCAGACACTTCTG |
| OY711 | 46 | AACACAACATTTTTAGTTTATGTATGTGTTTTTTGTAGTTATAG |
| OY712 | 47 | GCCTAACTCATTACTCGTGAGTAAGGAAAGAGTG |
| OY713 | 48 | ATTGAGTCATTGTTTTATATTTGTTGTAAAAAGTAGATAATTAC |
| OY715 | 49 | GTTCAGACATTTTGAATATGTATTACTTGGTTATGGTT |
| OY719 | 50 | AAAAGGTTTAAACGCTTTTTCAGTTCGAGTTTATCATTATC |
| OY720 | 51 | GTTTGACCATTTTGTTTGTTTATGTGTGTTTATTCGA |

TABLE 1-continued

Primers sequences used in the Examples.

| Identifier | SEQ ID NO: | Sequence (5'-3') |
|---|---|---|
| OY721 | 52 | TAAACTAAAAATGTTGTGTTCAGTAATTCAGAGAC |
| OY722 | 53 | ATACGAAGTTATGGCCGGCCAATGCTCTCTTATATTCTCACTGG |
| OY723 | 54 | ATATAAAACAATGACTCAATTCACTGACATTGATAAG |
| OY726 | 55 | CATATTCAAAATGTCTGAACCAGCTCAAAAG |
| OY727 | 56 | GTATTATATGTGGTGTGGGTATAACACGTG |
| OY729 | 57 | GCTGGAGGCCGGCCCACAAACGTTCCAAAGAAATAAACATTGC |
| OY730 | 58 | CATCATCACAATGGCTGCCGGTGTCCCAAA |
| OY732 | 59 | AACAAACAAAATGGTCAAACCAATTATAGCTCC |
| OY733 | 60 | TCACGAGTAATGAGTTAGGCACTTACGTATCTTG |
| OY735 | 61 | CGGCAGCCATTGTGATGATGTTTTATTTGTTTTGATTG |
| OY736 | 62 | CGCTCGAAGGCTTTGGCGCGGCTAAATGGAAAAAGGAAAGATTATTG |
| OY745 | 63 | AAAAGCGTTTAAACCTTTTCCCTTTTATGACGTATACG |
| OY748 | 64 | TTTGTGGGCCGGCCTCCAGCCAGTAAAATCCATACTC |
| OY818 | 65 | TCCATGGCCGCGGCCGCGTTTAAAC |
| OY819 | 66 | CGCCAAGCTGCGGCCGGCGCGCC |
| OY1003 | 67 | AGTACGAGACGACCACGAAG |
| OY1039 | 68 | ACCCACACCACATATAATACATATCACATAGGAAGCAACAG |
| OY1040 | 69 | ACTTGTTTCCCAATTGTTGC |
| OY1130 | 70 | GGCCGGCCATAACTTCGTATAGCATACATTATACGAAGTTATATTAACTC |
| OY1132 | 71 | GCAGCTTGGCGTAATCATGG |
| OY1133 | 72 | ATGGAGGCCAATTCACTGGC |
| OY1134 | 73 | GCCAGTGAATTGGCCTCCATGGCCGCGGCCGCAGTAGTCAACAATTCCCAGAGCTAC |
| OY1135 | 74 | CCATGATTACGCCAAGCTGCGGCCGGCGCGCCGCATTTCTTTCCAGACTTGTTCAAC |
| OY1137 | 75 | CCATGATTACGCCAAGCTGCGGCCGGCGCGCCTGTTGTGAGTCAATGTCGAGTTC |
| OY1139 | 76 | CCATGATTACGCCAAGCTGCGGCCGGCGCGCCGTGATTCTCTCGAAGGGTTTAAC |
| OY1140 | 77 | CCATGATTACGCCAAGCTGCGGCCGGCGCGCCAAAGCCTTCGAGCGTCC |
| OY1143 | 78 | GCGATCGCGAATTCTCGACACTGGATGG |
| OY1148 | 79 | ATACGAAGTTATGTTTAAACGATCCAGCTTGCCTCGTC |
| OY1151 | 80 | GCCAGTGAATTGGCCTCCATGGCCGCGGCCGCACACCGTCTTCCGCGTCAC |
| OY1152 | 81 | GTTTAAACATAACTTCGTATAATGTATGCTATACGAAGTTATGCCCATATTTAG |
| OY1153 | 82 | CTTTAGCCATGGTTGTTTATGTTCGGATGTG |
| OY1154 | 83 | ATAAACAACCATGGCTAAAGAATACTTTCCATTTAC |

TABLE 1-continued

Primers sequences used in the Examples.

| Identifier | SEQ ID NO: | Sequence (5'-3') |
|---|---|---|
| OY1155 | 84 | TCAGTACTGATTATTTACAGTGTAAGGCAACAATG |
| OY1156 | 85 | CTGTAAATAATCAGTACTGACAATAAAAAGATTCTTG |
| OY1157 | 86 | TGTCGAGAATTCGCGATCGCGCTTTTGGTCTGACAGTAAGTGTG |
| OY1158 | 87 | CCATGATTACGCCAAGCTGCGGCCGGCGCGCCAGGGTTAATGGTCTTGTGGAGT |
| OY1168 | 88 | GCCAGTGAATTGGCCTCCATGGCCGCGGCCGCACAATCTATCGATTGTATGGGAAGC |
| OY1169 | 89 | GTCTTCACCGGTGCGGCCGCGATCCAGCTTGCCTCGTC |
| OY1174 | 90 | GGTTAGAGGCTAGCGGCGCGCCGAATTCTCGACACTGGATGG |
| OY1197 | 91 | GTTTAAACATAACTTCGTATAATGTATGCTATACGAAGTTATGAATCAG |
| OY1198 | 92 | ATACGAAGTTATGTTTAAACCCTAAGAAATGAATAACAATACTGACA |
| OY1200 | 93 | CAGTTCTCACATCACATCCG |
| OY1201 | 94 | GAATCTTTTTATTGTCAGTACTGAGG |
| OY1203 | 95 | TATTCTTTAGCCATGTCGACTTGTTTATGTTCGGATGTGATGTGAGAAC |
| OY1207 | 96 | TATTCTTTAGCCATGTCGACCGGTGCAGGTTCGGATGTGATGTGAGAAC |
| OY1209 | 97 | TCGTCTTCACCGGTGCGGCCGCCCATGTATAATCATTTGCATCC |
| OY1210 | 98 | TCGTCTTCACCGGTGCGGCCGCTCCTCGCTGCAGACCTG |
| OY1211 | 99 | TACACTGTAAATAAGGTACCTCAGTACTGACAATAAAAAGATTCTTG |
| OY1212 | 100 | GTCGACATGGCTAAAGAATACTTTCCATTTAC |
| OY1213 | 101 | GGTACCTTATTTACAGTGTAAGGCAACAATG |
| OY1214 | 102 | GCCAGTGAATTGGCCTCCATGGCCGCGGCCGCCGGCATGCAAACATCTACAC |
| OY1215 | 103 | TGCTATACGAAGTTATGTTTAAACCATAACGCGTTACACGGAAG |
| OY1216 | 104 | GCGATCGCCTACTATCGGCGACTCTCTCG |
| OY1217 | 105 | CCATGATTACGCCAAGCTGCGGCCGGCGCGCCGAGCGAACGTAAGAGAGGTTAATG |
| OY1218 | 106 | TTTACAACAAATATAAAACAATGAAGCTTCAATTTTTTTCCTTTATTAC |
| OY1219 | 107 | CGCCGATAGTAGGCGATCGCTGTCCAGAAAGCAGTATGTTCC |
| OY1226 | 108 | ACATTATACGAAGTTATTTAATTAATTACTCGTGAGTAAGGAAAGAGTG |
| OY1227 | 109 | TGTTTTATATTTGTTGTAAAAAGTAGATAATTAC |
| OY1254 | 110 | CTGTCCTTTTACCAGACAACC |
| OY1263 | 111 | GTACAGAAGAGGACGAAGAAGG |
| OY1264 | 112 | GTTGATCAGTGTTCATGGTCTG |

TABLE 1-continued

Primers sequences used in the Examples.

| Identifier | SEQ ID NO: | Sequence (5'-3') |
|---|---|---|
| OY1275 | 113 | GCGATCCGTCCTAAGGCGCGCCTTTTAGCTTTGACATGATTAAGCTC |
| OY1277 | 114 | GATTACGCCAAGCTGCGGCCGCTTAATTAAGTTTAAACTCAGTTCAATACAACAGATCACG |
| OY1281 | 115 | TTCAATAGCATATCTTTGTTAACGAAGCATCTGTGCTTC |
| OY1282 | 116 | GCTAAAACTCGAGACGATACCTGAGTATTCCCACAG |
| OY1283 | 117 | GTATCGTCTCGAGTTTTAGCTTTGACATGATTAAGCTC |
| OY1284 | 118 | GCGGCCGCGATGTAGTTTCTGGTTTTTAAATCTCAC |
| OY1285 | 119 | AGAAACTACATCGCGGCCGCTCCTCGCTGCAGACCTG |
| OY1291 | 120 | AGACAATGTATGTATTTCGGTTCC |
| OY1300 | 121 | TGTTGTATTGAACTGAGTTTAAACCGACAGCCCTCCGACGG |
| OY1301 | 122 | CGCCAAGCTGCGGCCGCTTAATTAAAAAGCCTTCGAGCGTCCC |
| OY1305 | 123 | ATGGACGACATTGAAACAGC |
| OY1306 | 124 | TCATACCCTAGAAGTATTACGTGATTTTCTG |
| OY1319 | 125 | ATTGTGGCATTATAGTTTTTTCTCCTTGACGTTAAAGTATAGAG |
| OY1320 | 126 | AAAAACTATAATGCCACAATTTGATATATTATGTAAAACACC |
| OY1321 | 127 | AGGGGCCTGTTTATATGCGTCTATTTATGTAGGATGAAAGG |
| OY1322 | 128 | ACGCATATAAACAGGCCCCTTTTCCTTTG |
| OY1330 | 129 | AGTGTCGAGAATTCGGCGCGCCCACTCAAAGGTCAATTTCTTGTATG |
| OY1331 | 130 | GTTTAAACTGTGCTTGGGGTGGTTGG |
| OY1332 | 131 | GGATCCATAGTATTTAGACGGCCTGCAG |
| OY1334 | 132 | AGTGTCGAGAATTCGGCGCGCCGTACTTATTCCCTTCGAGATAATATCTAG |
| OY1335 | 133 | GTTTAAACTTTTAGTTTATGTATGTGATTTTTGTAGTTATAG |
| OY1336 | 134 | GGATCCGATTAATATAATTATATAAATATATTATCTTCTTTTCTTAATATCTAG |
| OY1342 | 135 | ACCCCAAGCACAGTTTAAACATGGTCAGTAAGGGTGAAGAAG |
| OY1343 | 136 | TAATTATATTAATCGGATCCTTATTTGTACAATTCATCCATACCAC |
| OY1366 | 137 | GACCTTGTCTGAGGCGCGCCGAATTCTCGACACTGGATGG |
| OY1374 | 138 | AAGGATCTTCTTGAGGACCTTGTCGAGCTCCGCACGGCGCGCACTGCAC |
| OY1375 | 139 | AAGGATCTTCTTGAGGACCTTGTCGAGCTCTGAGTAACCCATATAGAGTTCGTACAC |
| OY1376 | 140 | GGCGCGCCTCAGACAAGGTCCTCAAGAAGATCCTTTGATCTTTTCTACGG |
| OY1377 | 141 | CCTATACTCGACTAGCGGCCCTAGCTGGCCAGGGCCCGATACG |

TABLE 1-continued

Primers sequences used in the Examples.

| Identifier | SEQ ID NO: | Sequence (5'-3') |
|---|---|---|
| OY1400 | 142 | CCGTTTTGTTAGGTGCTGTGGGTGGTCCTAAATGGGGT ACGGTTTCAGGGTCCATAAAGC |
| OY1401 | 143 | GACCTTGTCTTTGGAGTTCAATGCGTCC |
| OY1402 | 144 | ATATACTACAACTGTGGGAATACTCAGGTATCGTCTCGA GGGTTTCAGGGTCCATAAAGC |
| OY1404 | 145 | ATACTAACGCCGCCATCCAGTGTCGAGAATTCGGCGCG CCTGAGTAACCCATATAGAGTTCGTACAC |
| OY1405 | 146 | GACTGTAAAGATGGACGCATTGAACTCCAAAGACAAGG TCGTACTTATTCCCTTCGAGATAATATCTAGG |
| OY1407 | 147 | ATACTAACGCCGCCATCCAGTGTCGAGAATTCGGCGCG CCCGCACGGCGCGCACTGC |
| OY1408 | 148 | GACTGTAAAGATGGACGCATTGAACTCCAAAGACAAGG TCCACTCAAAGGTCAATTTCTTGTATG |
| OY1409 | 149 | CATAAACTAAAAGTTTAAACATGGTCAGTAAGGGTGAAG AAG |
| OY1410 | 150 | CGTCTAAATACTATGGATCCTTATTTGTACAATTCATCCA TACCAC |
| OY1411 | 151 | GGCGCGCCGAATTCTCGACACTGGATGGCGG |
| OY1412 | 152 | ATACGAAAATGTAAACATTTCCTATACTCGACTAGCGGC CGCTCCTCGCTGCAGACCTG |
| OY1414 | 153 | ATACGAAAATGTAAACATTTCCTATACTCGACTAGCGGC CTTTGGAGTTCAATGCGTCC |
| OY1415 | 154 | CTCGAGACGATACCTGAGTATTCCCACAG |
| OY1418 | 155 | TGTGGGTGGTCCTAAATGGGAGGTTTCAGGGTCCATAA AGC |
| OY1419 | 156 | GCGGCCGCTCCTCGCTGCAGACCTG |
| OY1420 | 157 | CTGCAGCGAGGAGCGGCCGCCTCAAGAAGATCCTTTGA TCTTTTCTAC |
| OY1421 | 158 | CCTATACTCGACTAGCGGCCCTTAAGCTAGCTGGCCAG GGCCC |
| OY1422 | 159 | TGGCGCAGCGATACCGCCGCGCACGCTG |
| OY1423 | 160 | GCGGCGGTATCGCTGCGCCAGGTCCGG |
| OY1424 | 161 | CTTAAGGGCCGCTAGTCGAG |
| OY1425 | 162 | GCACCGGACTGTAACGAGC |
| OY1426 | 163 | TGGTATCTTTCCTGTAAATGGAAAGTATTC |
| OY1427 | 164 | CTCGACTAGCGGCCCTTAAGGATCCAGCTTGCCTCGTC |
| OY1429 | 165 | CTCGACTAGCGGCCCTTAAGCCATGTATAATCATTTGCA TCC |
| OY1496 | 166 | GGCATTACCACCATATACATATCC |
| OY1497 | 167 | CTTGTCTACTAAAATCTGAATTGTCC |
| OY2172 | 187 | CCTATCTGAGGAAAGTATTCCTTCATGTCGACTTGTTTAT GTTCG |

Example 1: Construction of Plasmid Vectors pYGT51

Plasmid pYGT5I was synthesized by GeneArt and contains a *Bacillus cereus* GAPN-2 gene codon optimized for *S. cerevisiae*.

pYGT162

Plasmid pYGT162 was synthesized by GeneArt and contains a *Candida intermedia* GXF1 gene codon optimized for *S. cerevisiae* flanked by a TEF1 promoter and a CYC1 terminator based on *S. cerevisiae* S288C. The transporter encoded by GXF1 is based on the transporter from Leandro et. Al. (2006, *Biochem. J.* 395, 543-549).

pYGT164

Plasmid pYGT164 was synthesized by GeneArt and contains a *Bos taurus* xylose isomerase gene (AZM80432 encoding the xylose isomerase of SEQ ID NO: 168) codon optimized for *S. cerevisiae*.

pFYD01

The KanMX cassette was designed based on the publication and plasmid pFA6a from Wach et al. (1994, *Yeast* 10: 1793-1808) and was synthesized by GeneArt delivered on a ColE1-based plasmid.

pFYD02

The NatR cassette was designed based on the publications of Krügel et al. (1993, *Gene* 127: 127-131), and Goldstein and McCusker (1999, *Yeast* 15: 1541-1553). NAT1 was derived from plasmid pHN15 (unpublished; nat1 Accession No. X73149). The plasmid containing the NatR cassette was synthesized by GeneArt.

pFYD03

The KanMX cassette from pFYD01 was PCR amplified using primers OY818 and OY819. The amplification reaction was performed using Phusion® Hot Start Flex DNA Polymerase (New England Biolabs) according to the manufacturer's instructions. The PCR was composed of 1 µL pFYD01 (diluted to ~5 ng/µL), 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 30 seconds; 30 cycles each at 98° C. for 10 seconds, 55° C. for 30 seconds and 72° C. for 2 minutes 30 s; and one cycle at 72° C. for 10 minutes. Following thermocycling, the PCR product was purified using 1% agarose gel electrophoresis in TBE buffer and the band corresponding to the expected product size was excised from the gel and purified using an Illustra GFX PCR DNA and Gel Band Purification Kit (GE Healthcare Life Sciences) according to the manufacturer's instructions. The PCR product was cloned into NotI-digested pJaL1258 (See, U.S. Pat. No. 9,574,199) using an In-Fusion® HD EcoDry™ Cloning Kit (Clontech Laboratories, Inc.) in a total volume of 10 µL composed of 2 µL pJaL1258 NotI fragment, 5 µL PCR product and 3 µL H$_2$O. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD03.

pFYD04

Plasmid pFYD04 was constructed using the approach described for pFYD03 except that pFYD02 was used as the PCR template.

pFYD07

Plasmid pFYD07 was constructed by cloning PCR products derived from pFYD02 and pYGT68 (a plasmid from Prof. Jens Nielsen, Chalmers) into PacI/AscI digested pFYD03. The PCR products were generated using primer sets OY608+OY619, OY620+OY633 and OY618+OY621, respectively. pFYD02 was used as template for PCR reactions with the first two primer set, whereas pYGT68 was used as template for PCR with the primer set OY618+OY621. The PCRs were composed of 1 µL plasmid DNA as template (diluted to ~5 ng/µL), 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 30 seconds; 30 cycles each at 98° C. for 10 seconds, 55° C. for 30 seconds and 72° C. for 2 minutes 30 s; and one cycle at 72° C. for 10 minutes. Following thermocycling, the PCR products were purified using 2% agarose gel electrophoresis in TBE buffer and the bands corresponding to the expected product size were excised from the gel and purified using an Illustra GFX PCR DNA and Gel Band Purification Kit (GE Healthcare Life Sciences) according to the manufacturer's instructions. The PCR products were cloned into PacI/AscI digested pFYD03 using an In-Fusion® HD EcoDry™ Cloning Kit (Clontech Laboratories, Inc.) in a total volume of 10 µL composed of 2 µL PacI/AscI pFYD03 fragment and a 2-molar excess of each PCR product. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD07.

pFYD08

Plasmid pFYD08 was constructed by cloning PCR products derived from pFYD02 and pYGT51 into PacI/AscI digested pFYD04. The PCR products were generated using primer sets OY608+OY614, OY617+OY633 and OY615+OY616, respectively. pFYD02 was used as template for PCR reactions with the first two primer sets, whereas pYGT51 was used as template for PCR with the primer set OY615+OY616. The PCRs were composed of 1 µL plasmid DNA as template (diluted to ~5 ng/µL), 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 30 seconds; 30 cycles each at 98° C. for 10 seconds, 55° C. for 30 seconds and 72° C. for 2 minutes 30 s; and one cycle at 72° C. for 10 minutes. Following thermocycling, the PCR products were purified using 2% agarose gel electrophoresis in TBE buffer and the bands corresponding to the expected product size were excised from the gel and purified using an Illustra GFX PCR DNA and Gel Band Purification Kit (GE Healthcare Life Sciences) according to the manufacturer's instructions. The PCR products were cloned into PacI/AscI digested pFYD03 using an In-Fusion® HD EcoDry™ Cloning Kit (Clontech Laboratories, Inc.) in a total volume of 10 µL composed of 2 µL PacI/AscI pFYD04 fragment and a 2-molar excess of each PCR product. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion patter was confirmed to be correct by DNA sequencing and designated pFYD08.

pFYD243

Plasmid pFYD243 was constructed by cloning PCR products derived from pFYD80 (FIG. 5) into a 7558 bp HindIII/NheI fragment of pJaL1258. The PCR products were generated using primer sets OY95+OY74, OY76+OY77 and OY80+OY96, respectively. The PCRs were composed of 1 µL plasmid DNA as template (diluted to ~5 ng/µL), 1×HF buffer, 200 µM of each dNTP, 500 nM forward primer, 500 nM reverse primer and 1 unit of Phusion® Hot Start Flex DNA Polymerase. For PCRs with the primer sets OY95+OY74 and OY80+OY96, the following program was used: the reactions were incubated in a Bio-Rad C1000 Touch™ Thermal Cycler (Bio-Rad Laboratories) programmed for 1 cycle at 98° C. for 3 minutes; 35 cycles each at 98° C. for 15 seconds, 60° C. for 30 seconds and 72° C. for 30 seconds; and one cycle at 72° C. for 5 minutes. For PCR with the primer set OY76+OY77, the following program was used: the reactions were incubated in a Bio-Rad C1000 Touch™ Thermal Cycler (Bio-Rad Laboratories) programmed for 1 cycle at 98° C. for 3 minutes; 35 cycles each at 98° C. for 15 seconds, 50° C. for 30 seconds and 72° C. for 1 minute; and one cycle at 72° C. for 5 minutes. Following thermocycling, the PCR products were purified using 2% agarose gel electrophoresis in TBE buffer and the bands corresponding to the expected product size were excised from the gel and purified using an Illustra GFX PCR DNA and Gel Band Purification Kit (GE Healthcare Life Sciences) according to the manufacturer's instructions. The PCR products were cloned into HindIII/NheI digested pJaL1258 (7558 bp) using an In-Fusion® HD EcoDry™ Cloning Kit (Clontech Laboratories, Inc.) in a total volume of 10 µL composed of 2 µL HindIII/NheI pJaL1258 fragment (7558 bp) and a 2-molar excess of each PCR product. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD243.

pFYD280

Figure 15:
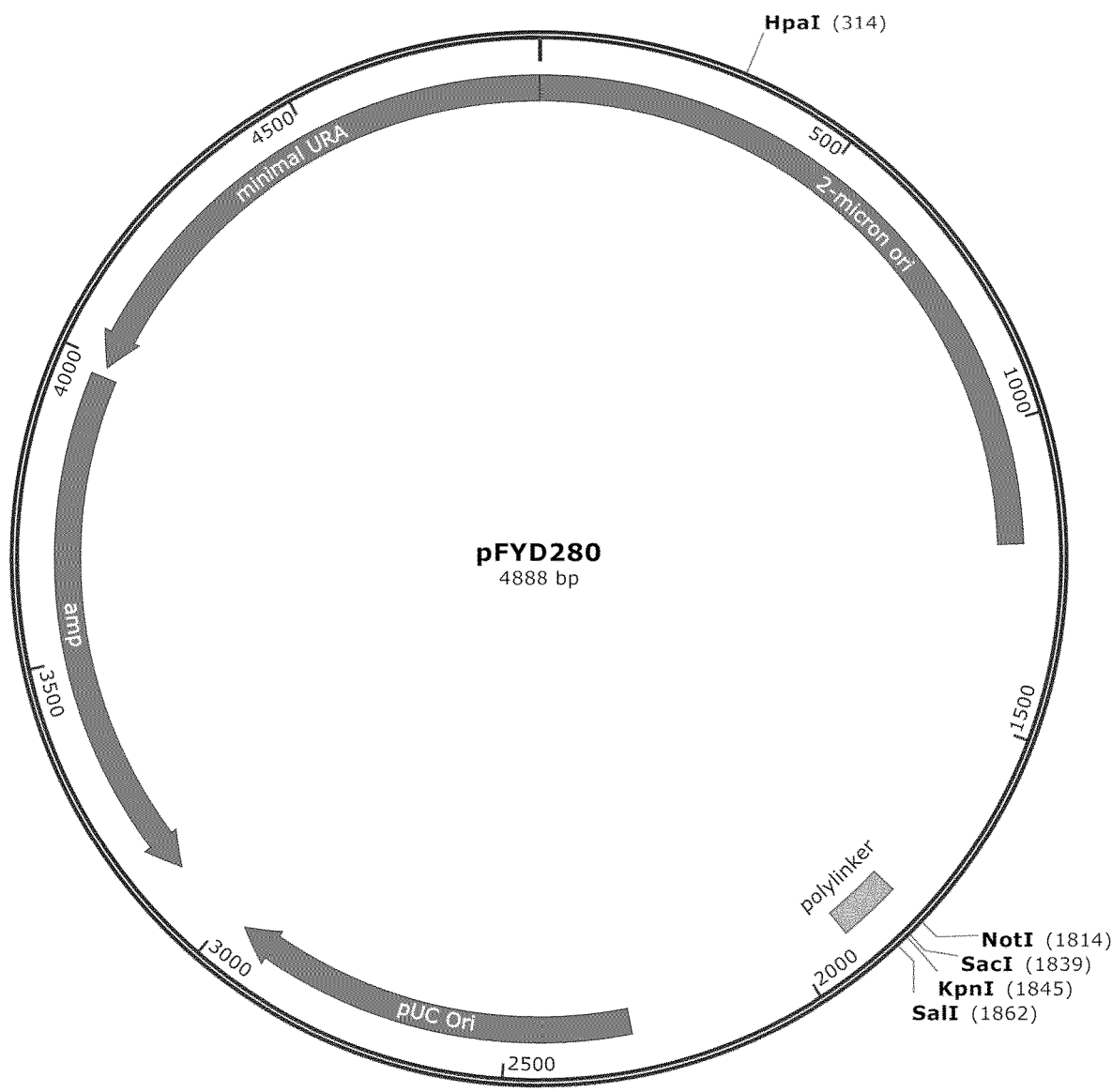
FIG. 15 shows a plasmid map of pFYD280.

The partial 2-micron plasmid pFYD280 (FIG. 15) was constructed by insertion of a 152 bp polylinker containing multiple cloning sites into AgeI/NheI digested pMiBg261 (4785 bp fragment). The polylinker was synthesized as a DNA string by GeneArt. The polylinker and pMiBg261 AgeI/NheI were assembled using an In-Fusion® HD EcoDry™ Cloning Kit (Clontech Laboratories, Inc.) in a total volume of 10 µL composed of approx. 50 ng pMiBg261 AgeI/NheI (4785 bp fragment) and a 2-molar excess of the polylinker. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD280 (FIG. 15).

pFYD400

Figure 6:
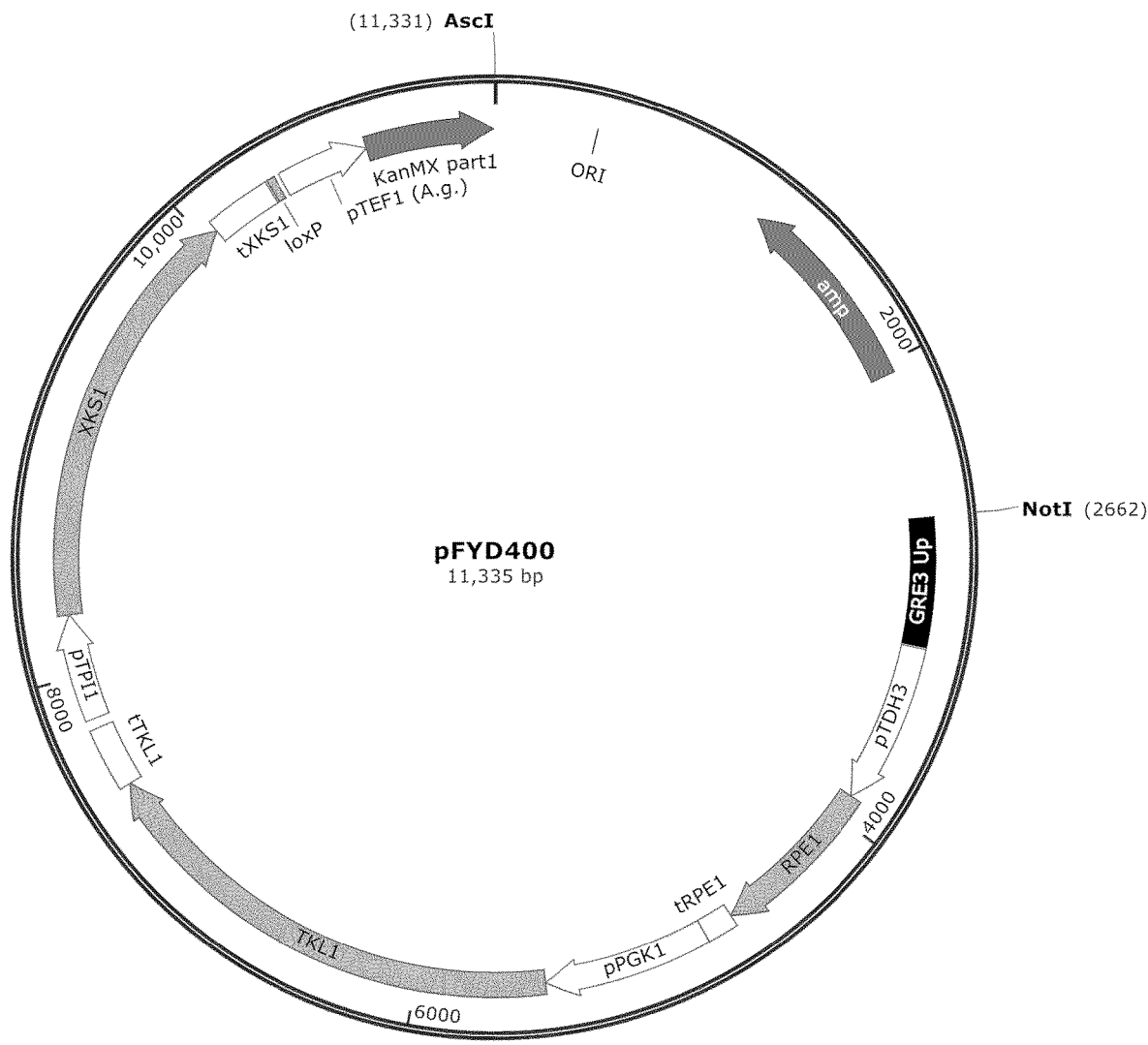
FIG. 6 shows a plasmid map of pFYD400.

Plasmid pFYD400 (FIG. 6) was constructed by cloning three PCR products (corresponding to the TPI1 promoter, XKS1 gene and a partial KanMX cassette) into AscI-digested pFYD402. The PCR products containing the TPI1 promoter, the XKS1 gene and the partial KanMX cassette were generated using primer sets OY710+OY711, OY721+OY722 and OY1130+OY1135, respectively, using YGT40 genomic DNA as template for the first two PCRs and pFYD07 DNA as template for the last PCR. The PCRs were composed of 50 ng genomic DNA or 5 ng plasmid DNA as template, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, the PCR products were purified using 1% agarose gel electrophoresis in TBE buffer and the bands corresponding to the expected product sizes were excised from the gel and purified using an Illustra GFX PCR DNA and Gel Band Purification Kit (GE Healthcare Life Sciences) according to the manufacturer's instructions. The PCR products were cloned into AscI-digested pFYD402 using an In-Fusion® HD EcoDry™ Cloning Kit (Clontech Laboratories, Inc.) in a total volume of 10 µL composed of 50 ng linearized plasmid and a 2-molar excess of each PCR product. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD400 (FIG. 6).

pFYD401

Figure 7:
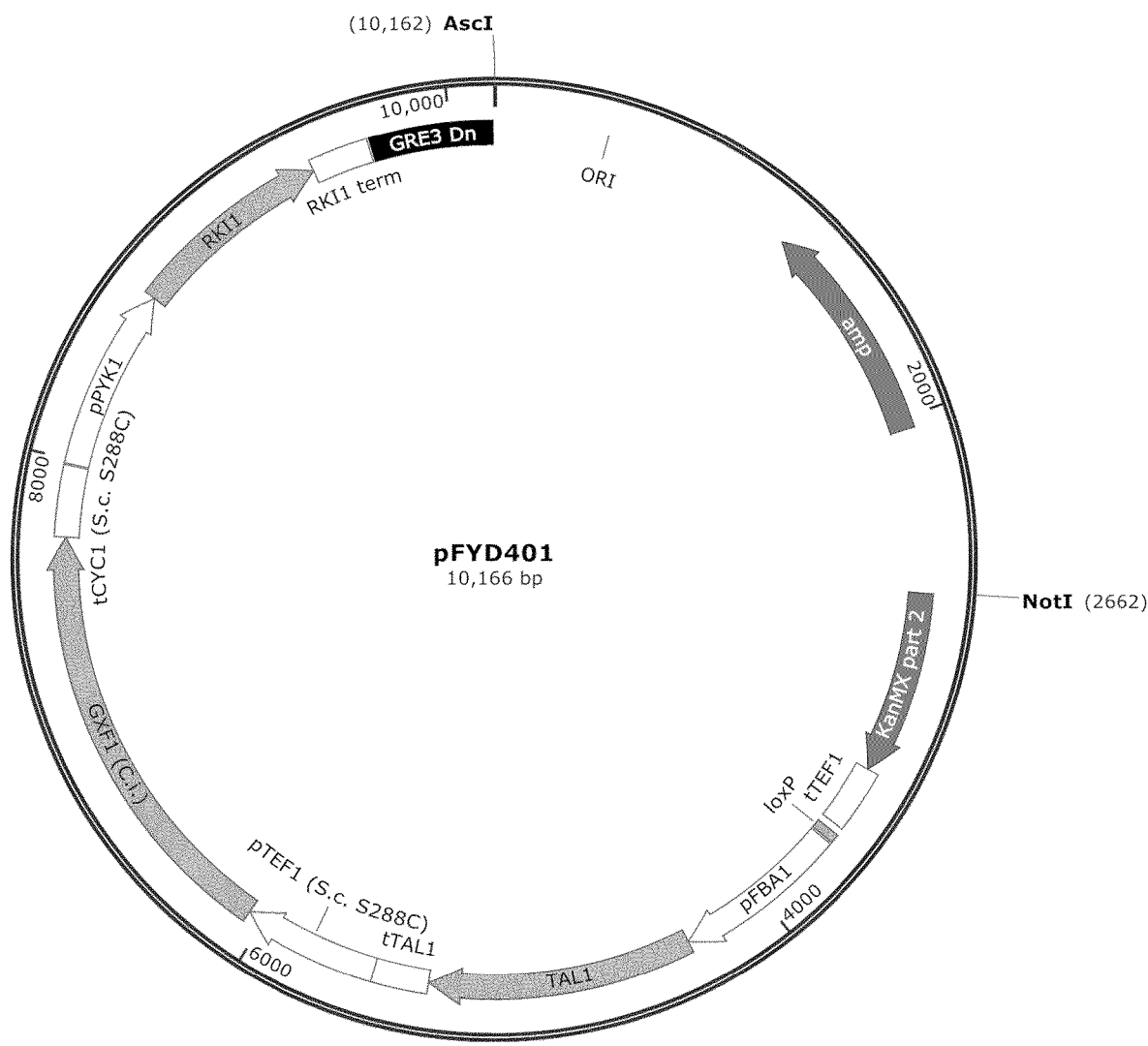
FIG. 7 shows a plasmid map of pFYD401.

Plasmid pFYD401 (FIG. 7) was constructed by cloning three PCR products (corresponding to the PYK1 promoter, the RKI1 gene and a region downstream of the GRE3 gene) into AscI-digested pFYD403. The PCR products containing the PYK1 promoter, the RKI1 gene and the downstream flank for the GRE3 gene were generated using primer sets OY735+OY736, OY729+OY730 and OY748+OY1137, respectively, using YGT40 genomic DNA as template. The PCRs were composed of 50 ng genomic DNA, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, the PCR products were purified using 1% agarose gel electrophoresis in TBE buffer and the bands corresponding to the expected product sizes were excised from the gel and purified using an Illustra GFX PCR DNA and Gel Band Purification Kit (GE Healthcare Life Sciences) according to the manufacturer's instructions. The PCR products were cloned into AscI-digested pFYD403 using an In-Fusion® HD EcoDry™ Cloning Kit (Clontech Laboratories, Inc.) in a total volume of 10 µL composed of 50 ng linearized plasmid and a 2-molar excess of each PCR product. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD401 (FIG. 7).

pFYD402

Plasmid pFYD402 was constructed from six PCR products (corresponding to a 2650 bp fragment of pJaL1258, a DNA region upstream of GRE3 for integration, the TDH3 promoter, the RPE1 gene, the PGK1 promoter and the TKL1 gene). The PCR products containing the pJal1258 fragment, the GRE3 upstream flank, the TDH3 promoter, the RPE1 gene, the PGK1 promoter and the TKL1 gene were amplified using primer sets OY1132+OY1133, OY1134+OY745, OY719+OY720, OY732+OY733, OY712+OY713 and OY723+OY1139, respectively. pFYD07 was used as template for the first PCR whereas YGT40 genomic DNA was used as template for the other PCRs. The PCRs were composed of 5 ng plasmid DNA or 50 ng genomic DNA, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, the PCR products were purified using 1% agarose gel electrophoresis in TBE buffer and the bands corresponding to the expected product sizes were excised from the gel and purified using an Illustra GFX PCR DNA and Gel Band Purification Kit (GE Healthcare Life Sciences) according to the manufacturer's instructions. The PCR products were assembled using an In-Fusion® HD EcoDry™ Cloning Kit (Clontech Laboratories, Inc.) in a total volume of 10 µL composed of 50 ng of the PCR product from primer set OY1132+OY1133 and a 2-molar excess of the other PCR products. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD402.

pFYD403

Plasmid pFYD403 was constructed from five PCR products (corresponding to a 2650 bp fragment of pJaL1258, a partial KanMX cassette, the FBA1 promoter, the TAL1 gene and a TEF1 promoter-driven GXF1 cassette). The PCR products containing the pJal1258 fragment, the partial KanMX cassette, the FBA1 promoter, the TAL1 gene and the TEF1 promoter-driven GXF1 cassette were amplified using primer sets OY1132+OY1133, OY1168+OY1197, OY1198+OY715, OY726+OY727 and OY1039+OY1140, respectively. pFYD07 was used as template for the first PCR, YGT40 genomic DNA was used as template for the next three PCRs and pYGT162 was used as template for the last PCR. The PCRs were composed of 5 ng plasmid DNA or 50 ng genomic DNA, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, the PCR products were purified using 1% agarose gel electrophoresis in TBE buffer and the bands corresponding to the expected product sizes were excised from the gel and purified using an Illustra GFX PCR DNA and Gel Band Purification Kit (GE Healthcare Life Sciences) according to the manufacturer's instructions. The PCR products were assembled using an In-Fusion® HD EcoDry™ Cloning Kit (Clontech Laboratories, Inc.) in a total volume of 10 µL composed of 50 ng of PCR product from primer set OY1132+OY1133 and a 2-molar excess of the other PCR products. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD403.

pFYD406

Plasmid pFYD406 was constructed from six PCR products generated using primer sets OY1151+OY1152, OY1148+OY1153, OY1154+OY1155, OY1156+OY1143, OY1157+OY1158 and OY1132+OY1133, respectively, using pFYD243, pFYD03, pYGT164, pFYD03, YGT40 and pFYD07 as template, respectively. The PCRs were composed of 5 ng plasmid DNA or 50 ng genomic DNA, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, the PCR products were purified using 1% agarose gel electrophoresis in TBE buffer and the bands corresponding to the expected product sizes were excised from the gel and purified using an Illustra GFX PCR DNA and Gel Band Purification Kit (GE Healthcare Life Sciences) according to the manufacturer's instructions. The PCR products were assembled using an In-Fusion® HD EcoDry™ Cloning Kit (Clontech Laboratories, Inc.) in a total volume of 10 µL composed of 50 ng of PCR product from primer set OY1132+OY1133 and a 2-molar excess of the other PCR products. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD406.

pFYD486

The partial 2-micron plasmid pFYD486 containing a *Bos taurus* xylose isomerase coding sequence (AZM80432 encoding the xylose isomerase of SEQ ID NO: 168) from pFYD406 was constructed by cloning PCR products derived from pFYD406, corresponding to a TEF1 promoter, a xylose isomerase gene and a TEF1 terminator, into NotI/AscI digested pFYD280 (FIG. 15). The PCR products were generated using primer sets OY1169+OY1203, OY1211+OY1174 and OY1212+OY1213. The PCRs were composed of 5 ng pFYD406 plasmid DNA, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, the PCR products were purified using 1% agarose gel electrophoresis in TBE buffer and the bands corresponding to the expected product sizes were excised from the gel and purified using an Illustra GFX PCR DNA and Gel Band Purification Kit (GE Healthcare Life Sciences) according to the manufacturer's instructions. The PCR products were assembled using an In-Fusion® HD EcoDry™ Cloning Kit (Clontech Laboratories, Inc.) in a total volume of 10 µL composed of 50 ng of NotI/AscI digested pFYD280 (FIG. 15) and a 2-molar excess of each PCR product. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD486.

pFYD496

Plasmid pFYD496 was constructed by exchanging the TEF1 promoter driven the xylose isomerase gene in pFYD486 with a truncated TEF1 promoter. A truncated version of the TEF1 promoter was amplified from pFYD406 using 5 ng pFYD406 plasmid DNA as template, 11×HF buffer, 200 µM of each dNTP, 500 nM primer OY1209, 500 nM primer OY1203 and 1 unit of Phusion® Hot Start Flex DNA Polymerase. The reaction was incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, the PCR product was purified using 2% agarose gel electrophoresis in TBE buffer and the band corresponding to the expected product size was excised from the gel and purified using an Illustra GFX PCR DNA and Gel Band Purification Kit (GE Healthcare Life Sciences) according to the manufacturer's instructions. The PCR product was cloned into NotI/SalI/PstI digested pFYD486 using an In-Fusion® HD EcoDry™ Cloning Kit (Clontech Laboratories, Inc.) in a total volume of 10 µL composed of 50 ng of NotI/SalI/PstI digested pFYD486 and a 2-molar excess of the PCR product. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD496.

pFYD505

Plasmid pFYD505 was constructed using the approach described for pFYD496 except that an even shorter TEF1 promoter fragment with five mutations in the kozak region was amplified from pFYD406 using primer set OY1210+OY1207. A plasmid yielding the desired restriction enzyme digestion pattern was confirmed to be correct by DNA sequencing and designated pFYD505.

pFYD511

Plasmid pFYD511 was constructed from four PCR products generated using primer sets OY1132+OY1133, OY1214+OY1215, OY1216+OY1217, OY1226+OY1227 and OY1218+OY1219, respectively, using pFYD07 as template for the PCR with primer set OY1132+OY1133 and JG169 genomic DNA (WO2008/008967) PCRs with the remaining primer sets. The PCRs were composed of 5 ng plasmid DNA or 50 ng genomic DNA, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, the PCR products were purified using 1% agarose gel electrophoresis in TBE buffer and the bands corresponding to the expected product sizes were excised from the gel and purified using an Illustra GFX PCR DNA and Gel Band Purification Kit (GE Healthcare Life Sciences) according to the manufacturer's instructions. The PCR products were assembled using an In-Fusion® HD EcoDry™ Cloning Kit (Clontech Laboratories, Inc.) in a total volume of 10 µL composed of 50 ng of the product from the PCR using primer set OY1132+OY1133 and a 2-molar excess of the other PCR products. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD511.

pFYD616

Figure 8:
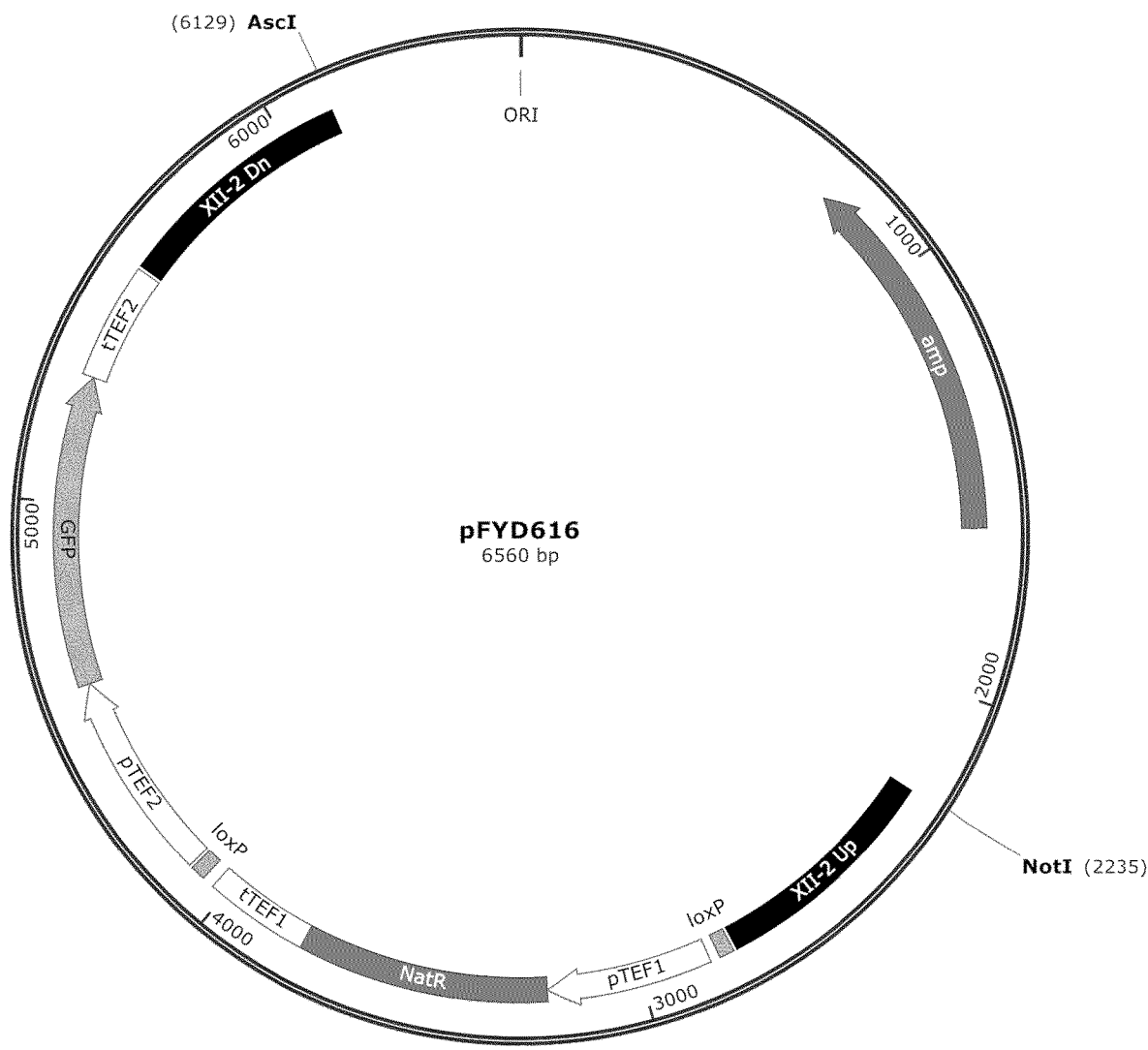
FIG. 8 shows a plasmid map of pFYD616.

Plasmid pFYD616 (FIG. 8) was constructed by insertion of a GFP gene into PacI/AsiSI digested pFYD511. The GFP gene was delivered by GeneArt as a synthetic DNA fragment. The GFP gene was cloned into pFYD511 PacI/AsiSI using an In-Fusion® HD EcoDry™ Cloning Kit (Clontech Laboratories, Inc.) in a total volume of 10 µL composed of 50 ng of PacI/AsiSI pFYD511 and a 2-molar excess of the GFP DNA fragment. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD616 (FIG. 8).

pFYD697

Plasmid pFYD697 carrying an inactive xylose isomerase gene was constructed by BsaBI/NdeI digestion of pFYD505 followed by Klenow treatment and ligation. The BsaBII/NdeI fragment corresponding to the plasmid backbone of pFYD505 and a partial xylose isomerase gene was isolated by 1% agarose gel electrophoresis in TBE buffer and purified using an Illustra GFX PCR DNA and Gel Band Purification Kit (GE Healthcare Life Sciences) according to the manufacturer's instructions. Next, the purified fragment was treated with DNA Polymerase I(Large (Klenow) Fragment) from New England Biolabs (cat. no. M0210S) to generate blunt ends according to the manufacturer's instructions. The blunt ends were then ligated together using the Quick Ligation™ Kit from New England Biolabs (cat. no. M2200S) and transformed into Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD697.

pFYD772

Figure 5:
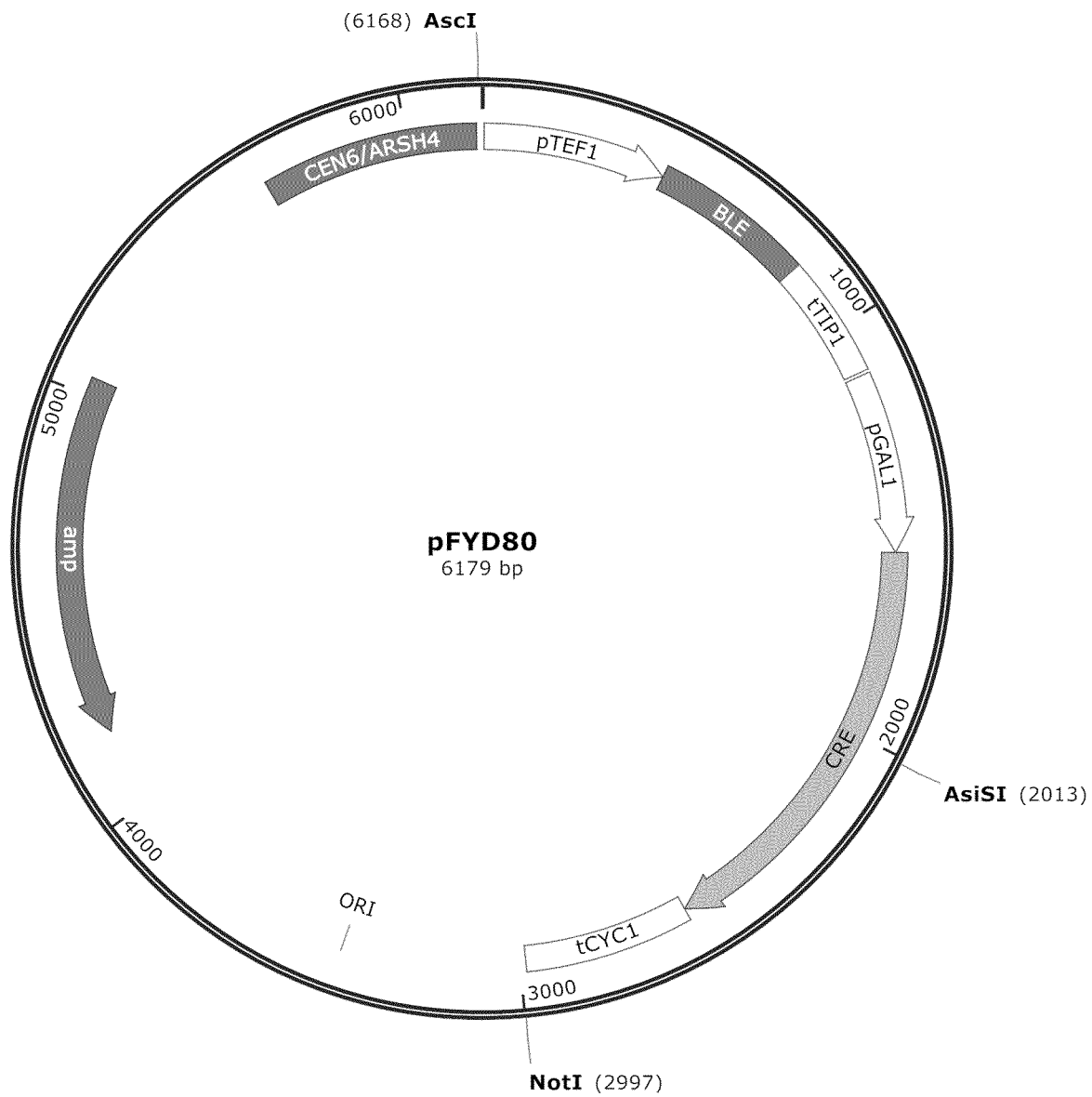
FIG. 5 shows a plasmid map of pFYD80.

Plasmid pFYD772 was constructed by insertion of a URA3 marker into AscI/AsiSI/NotI digested pFYD80 (FIG. 5). The URA3 marker including appropriate cloning sequences was PCR amplified from a synthetic DNA fragment supplied by GeneArt using primer set OY1275+OY1277. The PCR was composed of 5 ng DNA fragment as template, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, the PCR product was purified using 1% agarose gel electrophoresis in TBE buffer and the band corresponding to the expected product size was excised from the gel and purified using an Illustra GFX PCR DNA and Gel Band Purification Kit (GE Healthcare Life Sciences) according to the manufacturer's instructions. The PCR product was cloned into AscI/AsiSI/NotI digested pFYD80 (3171 bp) using an In-Fusion® HD EcoDry™ Cloning Kit (Clontech Laboratories, Inc.) in a total volume of 10 µL composed of 50 ng of AscI/AsiSI/NotI digested pFYD80 and a 2-molar excess of the PCR product. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion patter was confirmed to be correct by DNA sequencing and designated pFYD772.

pFYD776

Plasmid pFYD776, containing a galactose-inducible flippase cassette, was used to cure the FYD756 strain of its native 2-micron plasmid. The galactose-inducible flippase cassette was inserted as three PCR products into PacI/PmeI digested pFYD772. The PCR products were generated using primer sets OY1300+OY1319, OY1320+OY1321 and OY1322+OY1301, respectively, using pFYD80 (FIG. 5), pDB4164 (FIG. 9) and pFYD401 (FIG. 7) as template, respectively. The PCRs were composed of 5 ng plasmid DNA as template, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, the PCR products were purified using 1% agarose gel electrophoresis in TBE buffer and the bands corresponding to the expected product size were excised from the gel and purified using an Illustra GFX PCR DNA and Gel Band Purification Kit (GE Healthcare Life Sciences) according to the manufacturer's instructions. The PCR products were cloned into PacI/PmeI digested pFYD772 using an In-Fusion® HD EcoDry™ Cloning Kit (Clontech Laboratories, Inc.) in a total volume of 10 µL composed of 50 ng of PacI/PmeI digested pFYD772 and a 2-molar excess of each PCR product. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+amp plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD776.

pFYD839

Plasmid pFYD839 was synthesized by GeneArt and contains a synthetic TPI1 promoter and a synthetic TPI1 terminator. The promoter and terminator were based on the *S. cerevisiae* S288C but SNPs were introduced approximately every 20 bp to reduce homology to the corresponding TPI1 promoter and TPI1 terminator in JG169. The TPI1 promoter and terminator were later used to construct the mCherry expressing plasmid pFYD862.

pFYD840

Plasmid pFYD840 was synthesized by GeneArt and contains an *Ashbya gossypii* TPI 1 promoter and an *A. gossypii* terminator. The TPI1 promoter and terminator were later used to construct the mCherry expressing plasmid pFYD863.

pFYD844

Figure 9:
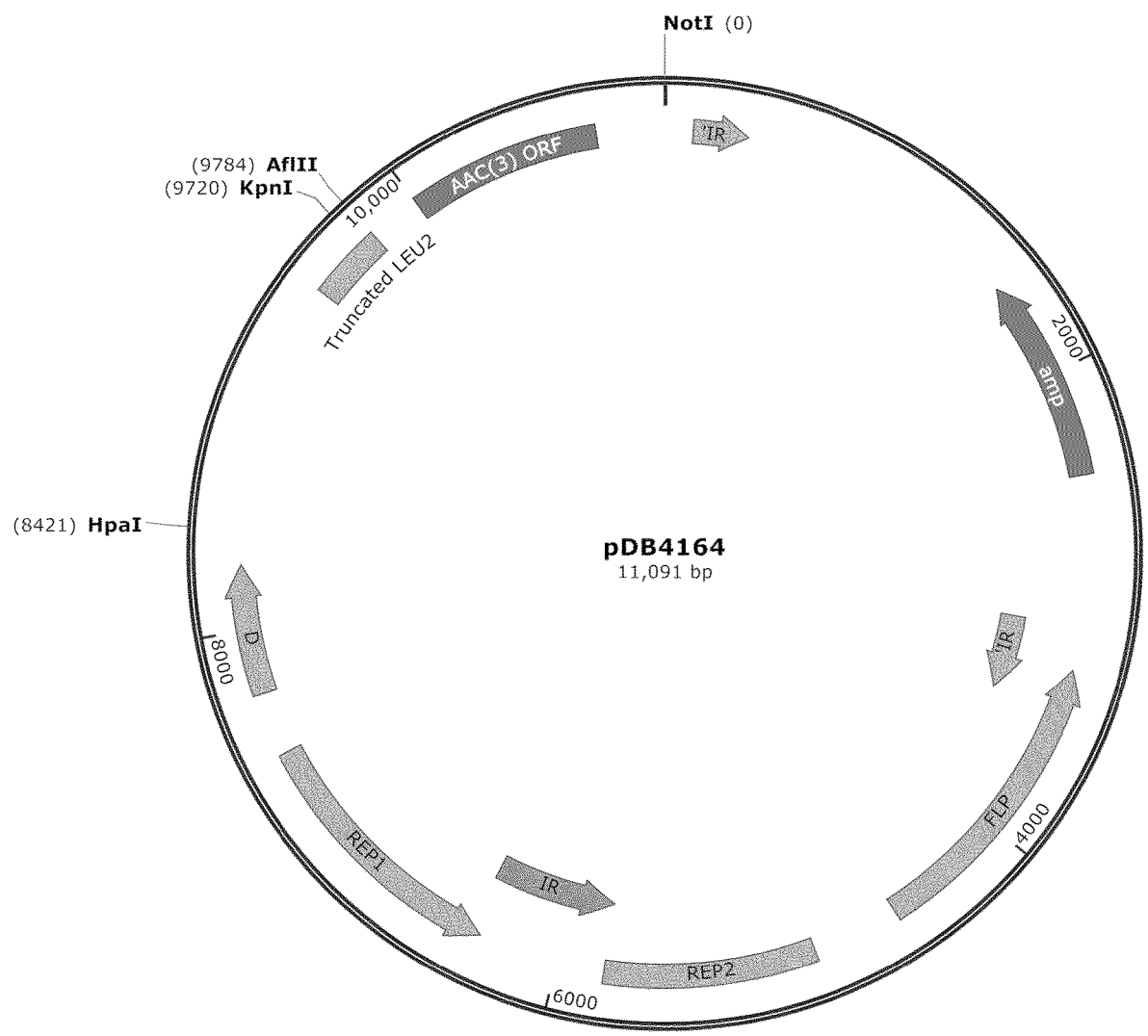
FIG. 9 shows a plasmid map of pDB4164.

The 2-micron plasmid pFYD844 was constructed by insertion of four PCR products into NotI/HpaI digested pDB4164 (FIG. 9). The PCR products were generated using primer sets OY1281+OY1282, OY1283+OY1284, OY1285+OY1366 and OY1376+OY1377, respectively, using pDB4164, a URA3 DNA string fragment, pFYD505 and pDB4164 as template, respectively. The PCRs were composed of 5 ng DNA as template, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 60° C. for 30 seconds and 72° C. for 1 minute; and one cycle at 72° C. for 5 minutes. Following thermocycling, the PCR products were purified using 1% agarose gel electrophoresis in TBE buffer and the bands corresponding to the expected product size were excised from the gel and purified using an Illustra GFX PCR DNA and Gel Band Purification Kit (GE Healthcare Life Sciences) according to the manufacturer's instructions. The PCR products were cloned into NotI/HpaI digested pDB4164 (8421 bp) using an In-Fusion® HD EcoDry™ Cloning Kit (Clontech Laboratories, Inc.) in a total volume of 10 µL composed of 50 ng of NotI/HpaI digested pDB4164 and a 2-molar excess of each PCR product. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+apramycin plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD844.

pFYD862

The 2-micron plasmid pFYD862 was constructed by insertion of a mCherry expression cassette into AscI/PflF1 digested pFYD844. The mCherry cassette was obtained as three PCR products generated with primer sets OY1334+OY1335, OY1409+OY1343 and OY1336+OY1375, respectively, using pFYD839, pDB5363 (provided by Albumedix™) and pFYD839 as template, respectively. The PCRs were composed of 5 ng plasmid DNA as template, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, the PCR products were purified using 2% agarose gel electrophoresis in TBE buffer and the bands corresponding to the expected product size were excised from the gel and purified using an Illustra GFX PCR DNA and Gel Band Purification Kit (GE Healthcare Life Sciences) according to the manufacturer's instructions. The PCR products were cloned into AscI/PflF1 digested pFYD844 (13291 bp) using an In-Fusion® HD EcoDry™ Cloning Kit (Clontech Laboratories, Inc.) in a total volume of 10 µL composed of 50 ng of AscI/PflF1 digested pFYD844 and a 2-molar excess of each PCR product. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+apramycin plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD862.

pFYD863

The 2-micron plasmid pFYD863 was constructed by insertion of a mCherry expression cassette into AscI/PflF1 digested pFYD844. The mCherry cassette was obtained as three PCR products generated with primer sets OY1330+OY1331, OY1342+OY1410 and OY1332+OY1374, respectively, using pFYD840, pDB5363 (provided by Albumedix™) and pFYD840 as template, respectively. The PCRs were composed of 5 ng plasmid DNA as template, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, the PCR products were purified using 2% agarose gel electrophoresis in TBE buffer and the bands corresponding to the expected product size were excised from the gel and purified using an Illustra GFX PCR DNA and Gel Band Purification Kit (GE Healthcare Life Sciences) according to the manufacturer's instructions. The PCR products were cloned into AscI/PflF1 digested pFYD844 (13291 bp) using an In-Fusion® HD EcoDry™ Cloning Kit (Clontech Laboratories, Inc.) in a total volume of 10 µL composed of 50 ng of AscI/PflF1 digested pFYD844 and a 2-molar excess of each PCR product. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+apramycin plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD863.

pFYD898

Figure 10:
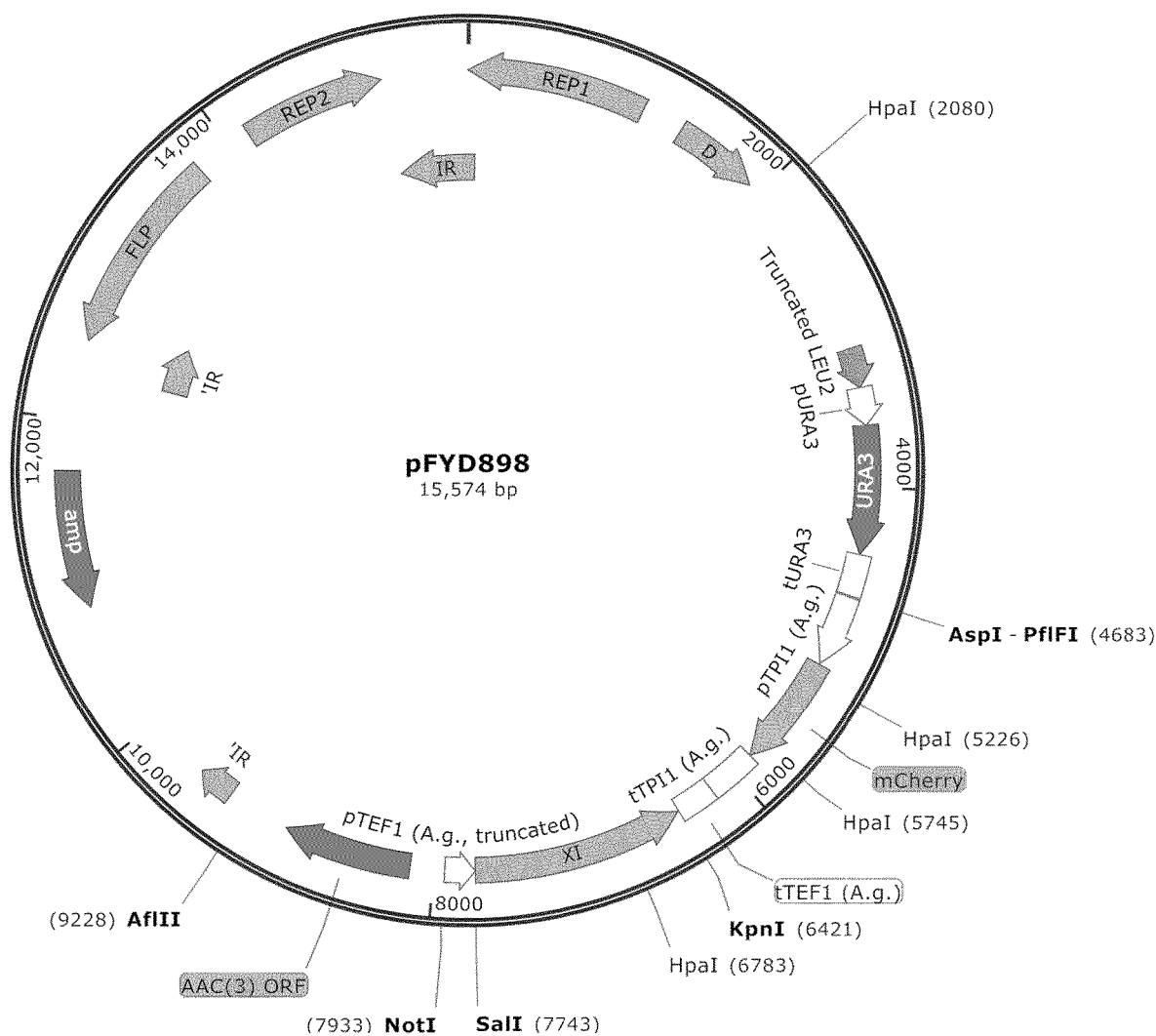
FIG. 10 shows a plasmid map of pFYD898.
Figure 11:
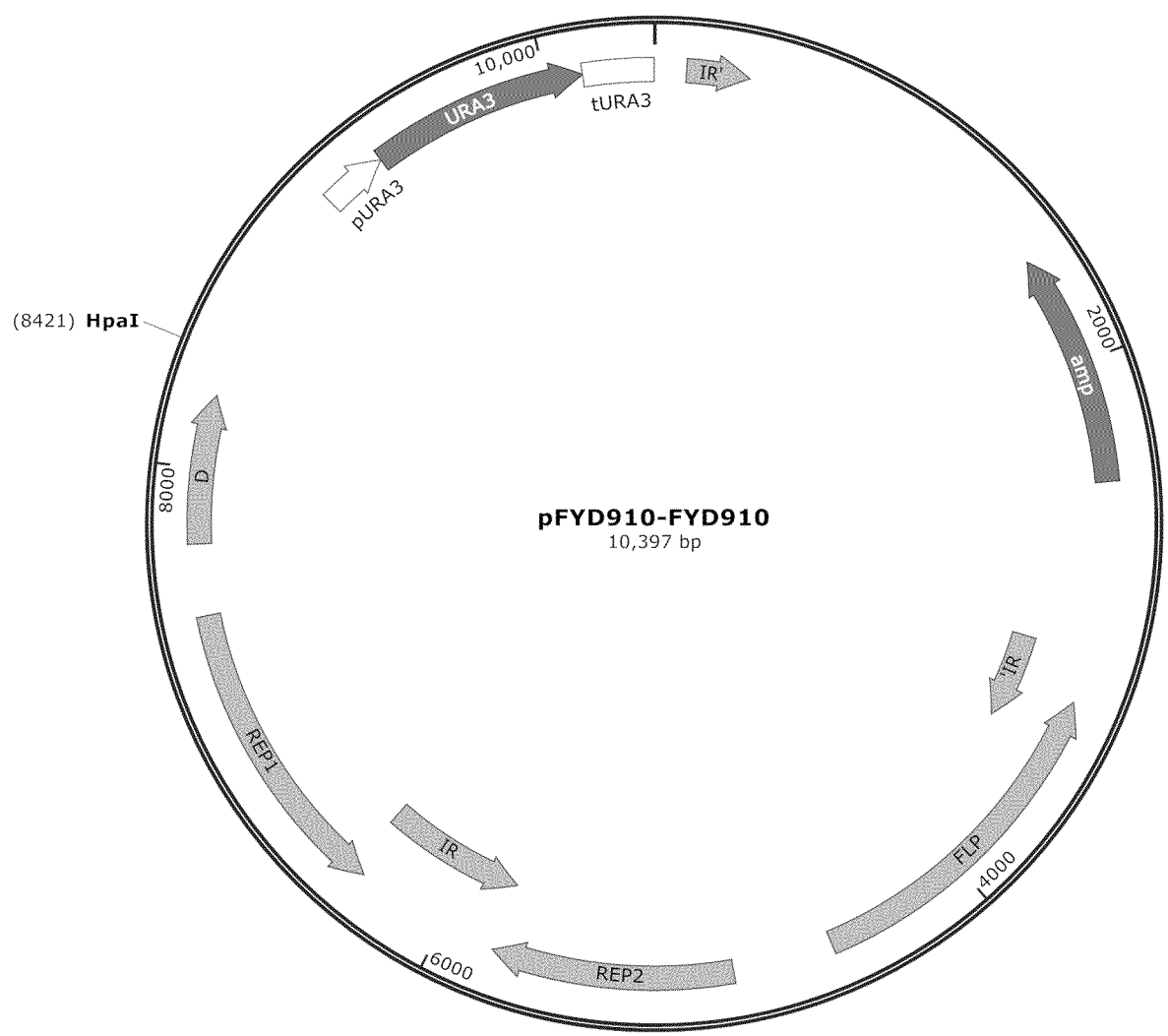
FIG. 11 shows a plasmid map of pFYD910.

It was discovered that yeast strains containing the 2-micron plasmids with the synthetic URA3 marker did not grow very well on minimal media. To overcome these issues different 2-micron plasmids were constructed in the FYD888 strain by gap-repair of a KpnI/NotI digested pDB4164 plasmid (FIG. 9) and multiple PCR products. The plasmid used as template for the construction of pFYD898 (FIG. 10) was obtained by gap-repair of KpnI/NotI digested pDB4164 with three PCR products. The PCR products were generated using primer sets OY1400+OY1401, OY1408+OY1407 and OY1411+OY1412, respectively, using YGT44, pFYD863 and pFYD844 as template, respectively. The PCRs were composed of 5 ng plasmid DNA as template, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, an aliquot of each PCR was loaded onto a 1% agarose gel to confirm that a single PCR product was obtained for each PCR. The remainder of each PCR and the KpnI/NotI digested pDB4164 was precipitated with 70% EtOH overnight at −20° C. and resuspended in MilliQ H₂O the next day. For the plasmid gap-repair, 50 fmol of KpnI/NotI digested pDB4164 was co-transformed with a 10× molar excess of each PCR product into competent FYD888 cells using the approach described by Gietz & Schiestl (2008) (a) except that 2×YPD media was used instead of 2×YPAD media. The transformation reaction was diluted 10× and 100× and 100 µL was plated onto SC-ura plates and incubated at 30° C. for 2-3 days. Four transformants were streaked for single colonies onto new SC-ura plates. DNA (plasmid and genomic DNA) was extracted from the transformants using the Master-Pure™ Yeast DNA Purification Kit (cat. no. MPY80010) from Epicentree. A total of two PCRs were prepared for each transformant using primer sets OY1418+OY1422 and OY1423+OY1419, respectively. An additional PCR containing an apramycin resistance marker was prepared from pDB4164 using primer set OY1420+OY1421. The PCRs were composed of 50 ng genomic DNA or 5 ng plasmid DNA as template, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 2 minutes; and one cycle at 72° C. for 5 minutes. Following thermocycling, the PCR products were purified using 1% agarose gel electrophoresis in TBE buffer and the bands corresponding to the expected product size were excised from the gel and purified using an Illustra GFX PCR DNA and Gel Band Purification Kit (GE Healthcare Life Sciences) according to the manufacturer's instructions. The PCR products were cloned into KpnI/NotI digested pDB4164 using an In-Fusion® HD EcoDry™ Cloning Kit (Clontech Laboratories, Inc.) in a total volume of 10 µL composed of 50 ng of KpnI/NotI digested pDB4164 and a 2-molar excess of each PCR product. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+apramycin plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD898 (FIG. 10).

pFYD899

Plasmid pFYD899 was constructed from pFYD898 (FIG. 10) by exchanging the xylose isomerase gene in pFYD898 with an inactive xylose isomerase gene PCR amplified from pFYD697. The PCR consisted of 5 ng plasmid DNA as template, 1×HF buffer, 200 µM of each dNTP, 500 nM primer OY1200, 500 nM primer OY1201 and 1 unit of Phusion® Hot Start Flex DNA Polymerase. The reaction was incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, the PCR product was purified using 1% agarose gel electrophoresis in TBE buffer and the PCR product was excised from the gel and purified using an Illustra GFX PCR DNA and Gel Band Purification Kit (GE Healthcare Life Sciences) according to the manufacturer's instructions. The PCR product was cloned into KpnI/SalI digested pFYD898 using an In-Fusion® HD EcoDry™ Cloning Kit (Clontech Laboratories, Inc.) in a total volume of 10 µL composed of 100 ng of KpnI/SalI digested pFYD898 and 25 ng of the PCR product. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+apramycin plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD899.
pFYD965

Figure 13:
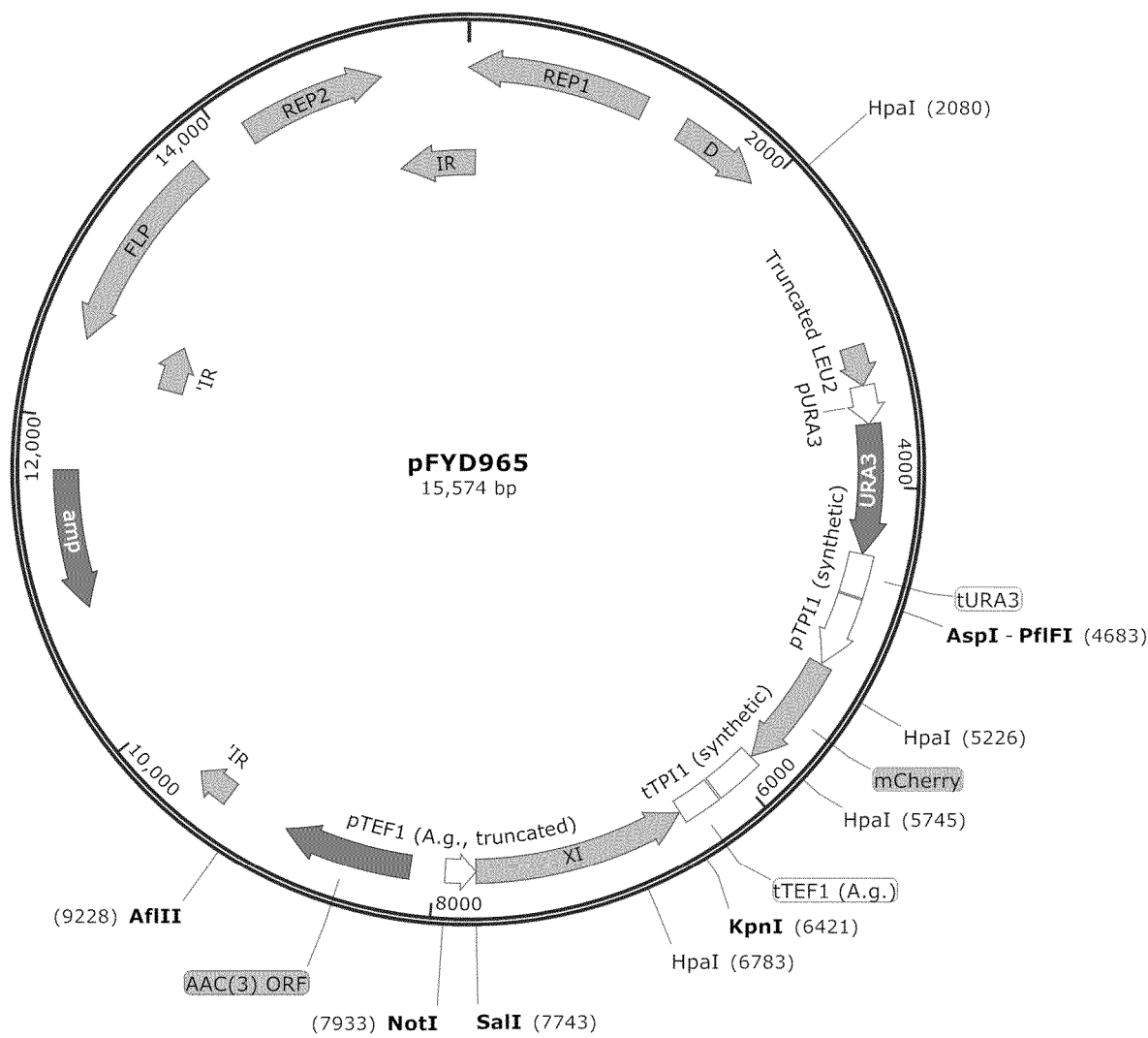
FIG. 13 shows a plasmid map of pFYD965.

The mCherry expression cassette on pFYD898 (FIG. 10) was exchanged with a PCR fragment containing the mCherry cassette from pFYD862 to create plasmid pFYD965 (FIG. 13). The PCR consisted of 5 ng pFYD862 plasmid DNA as template, 1×HF buffer, 200 µM of each dNTP, 500 nM primer OY1404, 500 nM primer OY1405 and 1 unit of Phusion® Hot Start Flex DNA Polymerase. The reaction was incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, the PCR product was purified using 1% agarose gel electrophoresis in TBE buffer and the PCR product was excised from the gel and purified using an Illustra GFX PCR DNA and Gel Band Purification Kit (GE Healthcare Life Sciences) according to the manufacturer's instructions. The PCR product was cloned into AscI/AspI digested pFYD898 using an In-Fusion® HD EcoDry™ Cloning Kit (Clontech Laboratories, Inc.) in a total volume of 10 µL composed of 100 ng of AscI/AspI pFYD898 fragment and a 2× molar excess of the PCR product. The reaction was incubated at 37° C. for 15 minutes, 50° C. for 15 minutes and then placed on ice. The reaction was used to transform Stellar™ Competent Cells (Clontech Laboratories, Inc.) according to the manufacturer's instructions. The transformation reaction was spread onto two LB+apramycin plates and incubated at 37° C. overnight. Putative transformant colonies were isolated from the selection plates and plasmid DNA was prepared from each one using a QIAprep 96 Turbo Kit (Qiagen) and screened for proper insertion of the fragments by digestion using appropriate restriction enzymes. A plasmid yielding the desired restriction enzyme digestion pattern was confirmed to be correct by DNA sequencing and designated pFYD965 (FIG. 13).
pFYD966

Figure 14:
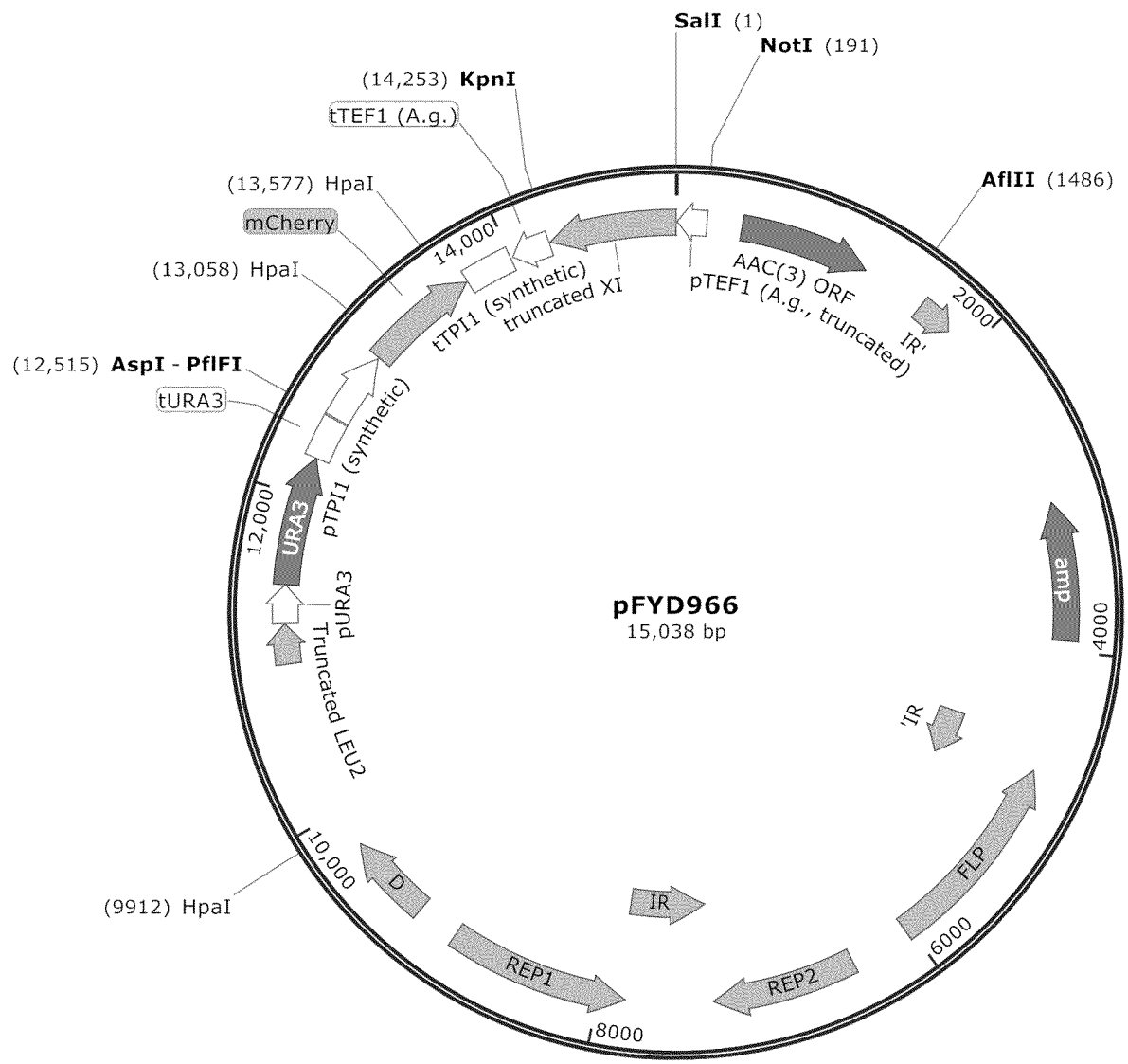
FIG. 14 shows a plasmid map of pFYD966.

The plasmid pFYD966 (FIG. 14) was constructed using the same approach as outlined for pFYD965 (FIG. 13) except that the mCherry cassette on pFYD899 was exchanged with the mCherry cassette from pFYD862. A plasmid yielding the desired restriction enzyme digestion pattern was confirmed to be correct by DNA sequencing and designated pFYD966 (FIG. 14).
Xylose Isomerase-Encoding Polynucleotide Strings Polynucleotides encoding various xylose isomerases (SEQ ID NOs: 2, 4, 6, 8, 10, 12, 14, 16, 18, 20, 22 and 24) were codon-optimized and synthesized by GeneArt. Each optimized sequence comprised the following:
  (1) To the 5' end was appended a sequence containing a 60 bp overlap GAP repair (GAPrep overlap). A BspQI site was included to cleave with in the GAPrep overlap. A nucleotide filler was included to ensure the integrity of the BspQI site after gene string synthesis and PCR.
  (2) To the 3' end was appended a sequence containing a TAA stop codon and a 60 bp overlap GAP repair (GAPrep overlap). A BspQI site was included to cleave within the GAPrep overlap. A nucleotide filler was included to ensure the integrity of the BspQI site after gene string synthesis and PCR.

PCR primer sites for primers OY198 and OY199 were included in all designs so that each string could be amplified to provide an approx. 1500 bp fragment for cloning. The synthesized products are shown as SEQ ID NOs: 169-180.
pFYD1049

Figure 16:
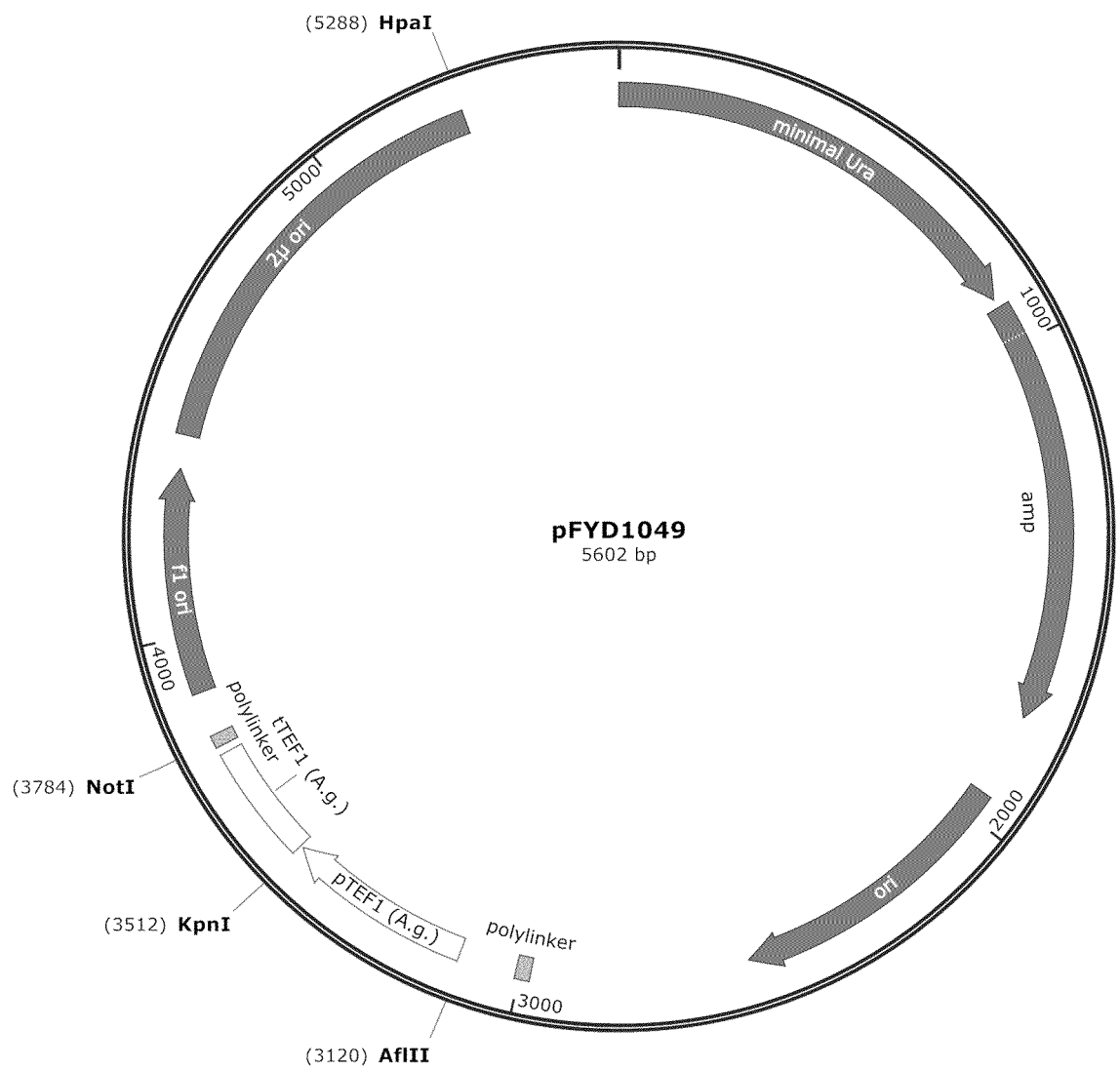
FIG. 16 shows a plasmid map of pFYD1049.

A 285 bp PCR fragment containing the TEF1 terminator from pFYD898 (using oligos OY239/OY240) and a 521 bp PCR fragment containing the TEF1 promoter (using oligos OY241/OY242) were cloned into the 4827 bp, EcoRI and HindIII linearized fragment of pFYD280 (FIG. 15) using an In-Fusion® HD EcoDry™ Cloning Kit (Clontech Laboratories, Inc.) according to manufacturer's instructions. A plasmid map of pFYD1049 is shown in FIG. 16.

Example 2: Construction of Recombinant Yeast Cells

FYD620

Strain *S. cerevisiae* FYD620 was constructed by transformation and integration of the pentose phosphate pathway (PPP) & GXF1 expression construct from pFYD400 (FIG. 6) and pFYD401 (FIG. 7) at the GRE3 locus in JG169. Competent JG169 cells were prepared according to the protocol described in Gietz & Schiestl (2007, *Nat. Protocols* Vol. 2. No. 1. (corrected online 20 Nov. 2008)) except that 2×YPD media was used instead of 2×YPAD media. The pFYD400 and pFYD401 plasmids were digested with NotI-HF and AscI and the DNA was precipitated with 70% (v/v) EtOH overnight at −20° C. The DNA was resuspended in MilliQ H2O and approx. 1 µg of each DNA fragment was used to transform competent JG169 cells. Following transformation, cells were pelleted at 13,000×g for 30 seconds. Cells were resuspended in 1 mL 2×YPD media and incubated at 30° C. in a thermomixer with shaking for 3 hours. Cells were spread onto YPD+200 µg/mL Geneticin (G418) plates and incubated at 30° C. for 2-3 days. Putative transformants were streaked on new YPD+200 µg/mL G418 plates and incubated at 30° C. for 2-3 days. Genomic DNA was extracted from six transformants using the MasterPure™ Yeast DNA Purification Kit (cat. no. MPY80010) from Epicentree. The genomic DNA was digested with 1) PacI/SphI or 2) HindIII-HF/NdeI and used for southern blotting. Correct integration of the combined PPP and GXF1 expression construct at the GRE3 locus was verified using two different probes corresponding to the GRE3 upstream flank and the GRE3 downstream flank. DNA for the GRE3 upstream and GRE3 downstream probes was PCR amplified with primer sets OY1134+OY745 and OY748+OY1137 using pFYD400 and pFYD401 plasmid DNA as template, respectively. The PCRs consisted of 5 ng plasmid DNA as template, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 30 cycles each at 98° C. for 10 seconds, 55° C. for 30 seconds and 72° C. for 1 minute; and one cycle at 72° C. for 5 minutes.

Following thermocycling, the PCR products were purified using 1% agarose gel electrophoresis in TBE buffer and the PCR products were excised from the gel and purified using an Illustra GFX PCR DNA and Gel Band Purification Kit (GE Healthcare Life Sciences) according to the manufacturer's instructions. Approximately 50 ng of each PCR fragment was used for radioactive labelling of the upstream and downstream probes, respectively. The probes were radioactively labelled with $^{32}$P.

DNA hybridization was carried out for 16 hours at 65° C. in a standard hybridization buffer of 10× Denhart's solution, 5×SSC, 0.02 M EDTA, 1% SDS, 0.15 mg/ml polyA RNA and 0.05 mg/ml yeast tRNA. After hybridization, the filters were washed in 2×SSC, 0.1% SDS at 65° C. twice and exposed to X-ray films. One transformant with the desired hybridization pattern for the two probes was selected and saved as FYD620.

FYD626

Strain S. cerevisiae FYD626 was obtained from FYD620 by removal of the KanMX resistance marker (flanked by loxP sites) present in the PPP and GXF1 expression construct using pFYD80 (FIG. 5). Competent FYD620 cells were prepared according to the protocol described in Gietz & Schiestl (2007, Nat. Protocols Vol. 2. No. 1. (corrected online 20 Nov. 2008)) and transformed with 1 μg of the pFYD80 plasmid carrying a Cre-recombinase expression cassette causing excision of the KanMX marker, which was flanked by loxP sites. Following transformation, cells were pelleted at 13,000×g for 30 seconds. Cells were resuspended in 1 mL YPD media and incubated at 30° C. in a thermomixer with shaking for 3 hours. Twenty μL and 200 μL aliquots of the cell suspension were plated onto YPD+200 μg/mL Zeocin plates and incubated at 30° C. for 2-3 days. Four transformants were re-streaked onto YPD+200 μg/mL Zeocin plates and incubated at 30° C. for 2-3 days. A small amount of colony material from each transformant was pooled and used to prepare a 10 ml YPD tube culture, which was incubated overnight at 30° C. Next day, serial dilutions of the culture were prepared and 100 μl from each dilution was spread onto YPD agar plates and incubated the plates at 30° C. for two days. A YPD plate with an appropriate number of colonies was picked and the colonies were replica-plated onto YPD+G418, YPD+Zeocin and YPD agar plates. The plates were incubated overnight at 30° C. Next day, the plates were inspected and colonies sensitive to both G418 (lost the KanMX marker) and Zeocin (lost the pFYD80 plasmid) were re-streaked onto YPD agar plates and incubated at 30° C. for two days. One of the transformants was saved as FYD626.

FYD714

Strain S. cerevisiae FYD714 was constructed by integration of the GFP expression cassette at the CHR XII-2 locus in FYD626. Competent FYD626 cells were prepared according to Gietz & Schiestl (2007, Nat. Protocols Vol. 2. No. 1. (corrected online 20 Nov. 2008)) except that 2×YPD media was used instead of 2×YPAD media. The pFYD616 plasmid (FIG. 8) was digested with AscI and NotI-HF and the DNA was precipitated with 70% (v/v) EtOH overnight at −20° C. The DNA was resuspended in MilliQ H$_2$O and approx. 1 μg of each DNA fragment was used to transform competent FYD626 cells. Following transformation, cells were pelleted at 13,000×g for 30 seconds. Cells were resuspended in 1 mL YPD media and incubated at 30° C. in a thermomixer with shaking for 3 hours. Ten μL and 100 μL cell suspension were spread onto two YPD+100 μg/mL ClonNat (NAT) agar plates and incubated at 30° C. for 2-3 days. Eight transformants were streaked on new YPD+100 μg/mL NAT plates and incubated at 30° C. for 2-3 days. Correct integration of the GFP expression cassette at the CHR XII-2 locus was verified by colony PCR using the Phire Plant Direct PCR Kit (Thermo Scientific). Colony material was collected using a small plastic inoculation loop (approx. 1 μL) and transferred to 20 μL Dilution buffer (provided with the kit). The samples were briefly vortexed and incubated for five minutes at room temperature and then centrifuged for 20 seconds in a microcentrifuge. Each 20 μL PCR consisted of 0.5 μL template, 1× Phire Plant PCR buffer (incl. dNTPs), 500 nM forward primer, 500 nM reverse primer, 0.4 μL Phire Hot Start II DNA Polymerase and MilliQ H$_2$O to a final volume of 20 μL. The reactions were incubated in a Bio-Rad C1000 Touch™ Thermal Cycler (Bio-Rad Laboratories) programmed for 1 cycle at 98° C. for 5 minutes; 40 cycles each at 98° C. for 5 seconds, 55° C. for 5 seconds and 72° C. for 30 seconds; and one cycle at 72° C. for 1 minute. The left side of integration was verified using primer set OY1263+OY1003 and the right flank was verified using primer set OY1254+OY1264. One transformant giving rise to the expected PCR products was saved as FYD714.

FYD756

Strain S. cerevisiae FYD756 was obtained from FYD714 by removal of the Nat resistance marker (flanked by loxP sites) present in the GFP expression construct using pFYD80 (FIG. 5). Competent FYD756 cells were prepared according to the protocol described in Gietz & Schiestl (2007, Nat. Protocols Vol. 2. No. 1. (corrected online 20 Nov. 2008)) and transformed with 1 μg of pFYD80. Following transformation, cells were pelleted at 13,000×g for 30 seconds. Cells were resuspended in 1 mL YPD media and incubated at 30° C. in a thermomixer with shaking for 3 hours. Twenty μL and 200 μL aliquots of the cell suspension were plated onto YPD+200 μg/mL Zeocin plates and incubated at 30° C. for 2-3 days. Four transformants were re-streaked onto YPD+ 200 μg/mL Zeocin plates and incubated at 30° C. for 2-3 days. A small amount of colony material from each transformant was pooled and used to prepare a 10 ml YPD tube culture, which was incubated overnight at 30° C. Next day, serial dilutions of the culture were prepared and 100 μl from each dilution was spread onto YPD agar plates and incubated the plates at 30° C. for two days. A YPD plate with an appropriate number of colonies was picked and the colonies were replica-plated onto YPD+NAT, YPD+Zeocin and YPD agar plates. The plates were incubated overnight at 30° C. Next day, the plates were inspected and colonies sensitive to both NAT (lost the NAT marker) and Zeocin (lost the pFYD80 plasmid) were re-streaked onto YPD agar plates and incubated at 30° C. for two days. One of the transformants was saved as FYD756.

FYD888

The cir$^0$ strain FYD888 was obtained by curing the FYD756 strain of its native 2-micron plasmid using the protocol outlined in Rose & Broach (1990, Processes in Enzymology, Vol. 185) except that the pFYD776 plasmid (URA3 selection marker) was used instead of pFV17. Competent FYD756 cells were prepared according to Gietz & Schiestl (2008) (a) except that 2×YPD media was used instead of 2×YPAD media. Competent cells were transformed with 1 μg pFYD776 plasmid. Following transformation, serial dilutions of the transformed cells were prepared and plated onto SD agar plates and incubated at 30° C. for 3-4 days. Eight transformants were picked and re-streaked onto SD agar plates and incubated at 30° C. for 3-4 days. Next, the transformants were streaked onto SG (galactose) agar plates and incubated at 30° C. for 4 days. The biggest colonies (one per transformant) were picked and re-streaked onto SG agar plates and incubated at 30° C. for 4 days. The transformants were re-streaked once more on SG agar plates and incubated at 30° C. for 4 days. In the morning two 10 ml YPD tube cultures were prepared by pooling colony material from four transformants per tube and incubated at 30° C. In the afternoon, the cultures were diluted 1000× in 10 ml fresh YPD and incubated at 30° C. overnight. Next day, serial dilutions were prepared for the overnight cultures and spread onto YPD agar plates and incubated at 30° C. for 1-2 days. A YPD plate with an appropriate number of colonies was picked and the colonies were replica-plated onto YPD and SD agar plates and incubated for 1-2 days. Four colonies, which grew on the YPD agar plate but not on the SD agar plate (should have lost the pFYD776 plasmid), were used to inoculate test tubes containing 10 ml YPD and incubated at 30° C. for two days. DNA (genomic and potential plasmid DNA) was extracted from the cultures using the MasterPure™ Yeast DNA Purification Kit (cat. no. MPY80010) from Epicentre®. The genomic DNA was digested with NdeI and used for souther blotting (FYD756 DNA was included as a positive control for the probes). Absence of the pFYD776 plasmid and the native 2-micron plasmid was verified using two different probes, 1) targeting the flippase gene (FLP) present on the native 2-micron plasmid as well as pFYD776 and 2) targeting the REP2 gene present on the native 2-micron plasmid. DNA for probe 1 and probe 2 was generated using primer sets OY60+OY61 and OY1305+OY1306, respectively, using pFYD776 and JG169 as template, respectively. The PCRs consisted of 5 ng pFYD776 plasmid DNA or 50 ng of JG169 DNA as template, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 30 cycles each at 98° C. for 10 seconds, 55° C. for 30 seconds and 72° C. for 1 minute; and one cycle at 72° C. for 5 minutes. Following thermocycling, the PCR products were purified using 1% agarose gel electrophoresis in TBE buffer and the PCR products were excised from the gel and purified using an Illustra GFX PCR DNA and Gel Band Purification Kit (GE Healthcare Life Sciences) according to the manufacturer's instructions. Approximately 50 ng of each PCR fragment was used for radioactive labelling of the probes, respectively. The probes were radioactively labelled with $^{32}P$.

DNA hybridization was carried out for 16 hours at 65° C. in a standard hybridization buffer of 10× Denhart's solution, 5×SSC, 0.02 M EDTA, 1% SDS, 0.15 mg/ml polyA RNA and 0.05 mg/ml yeast tRNA. After hybridization, the filters were washed in 2×SSC, 0.1% SDS at 65° C. twice and exposed to X-ray films. The parental strain for FYD888 (i.e. FYD756) was included as a control for detection of the native 2-micron plasmid (positive signal with both probes). A dilution of pFYD776 was added as a control for detection of the pFYD776 plasmid (only detection using the OY60+OY61 generated probe). All transformants had lost the native 2-micron plasmid and the pFYD776 plasmid. One of them was saved as FYD888.

FYD910

Strain *S. cerevisiae* FYD910 carrying a 2-micron plasmid with a URA3 selection marker was constructed by gap-repair of HpaI/NotI-HF digested pDB4164 (FIG. 9) and two PCR products in FYD888. The two PCR products used for gap-repair of HpaI/NotI-HF digested pDB4164 were amplified from YGT44 and pDB4164, respectively, using primer sets OY1402+OY1414 and OY1291+OY1415, respectively. The PCRs were composed of 50 ng genomic DNA or 5 ng plasmid DNA as template, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, an aliquot of each PCR was loaded onto a 1% agarose gel to confirm that a single PCR product was obtained for each PCR. The remainder of each PCR and the HpaI/NotI-HF digested pDB4164 was precipitated with 70% EtOH overnight at −20° C. and resuspended in MilliQ $H_2O$ the next day. For the plasmid gap-repair, 50 fmol of HpaI/NotI-HF digested pDB4164 was co-transformed with a 10× molar excess of each PCR product into competent FYD888 cells using the approach described by Gietz & Schiestl (2008) (a) except that 2×YPD media was used instead of 2×YPAD media. The transformation reaction was diluted 10× and 100× and 100 µL was plated onto SC-ura plates and incubated at 30° C. for 2-3 days. Four transformants were streaked for single colonies onto new SC-ura plates. One of the transformants was saved as FYD910.

FYD932

Figure 12:
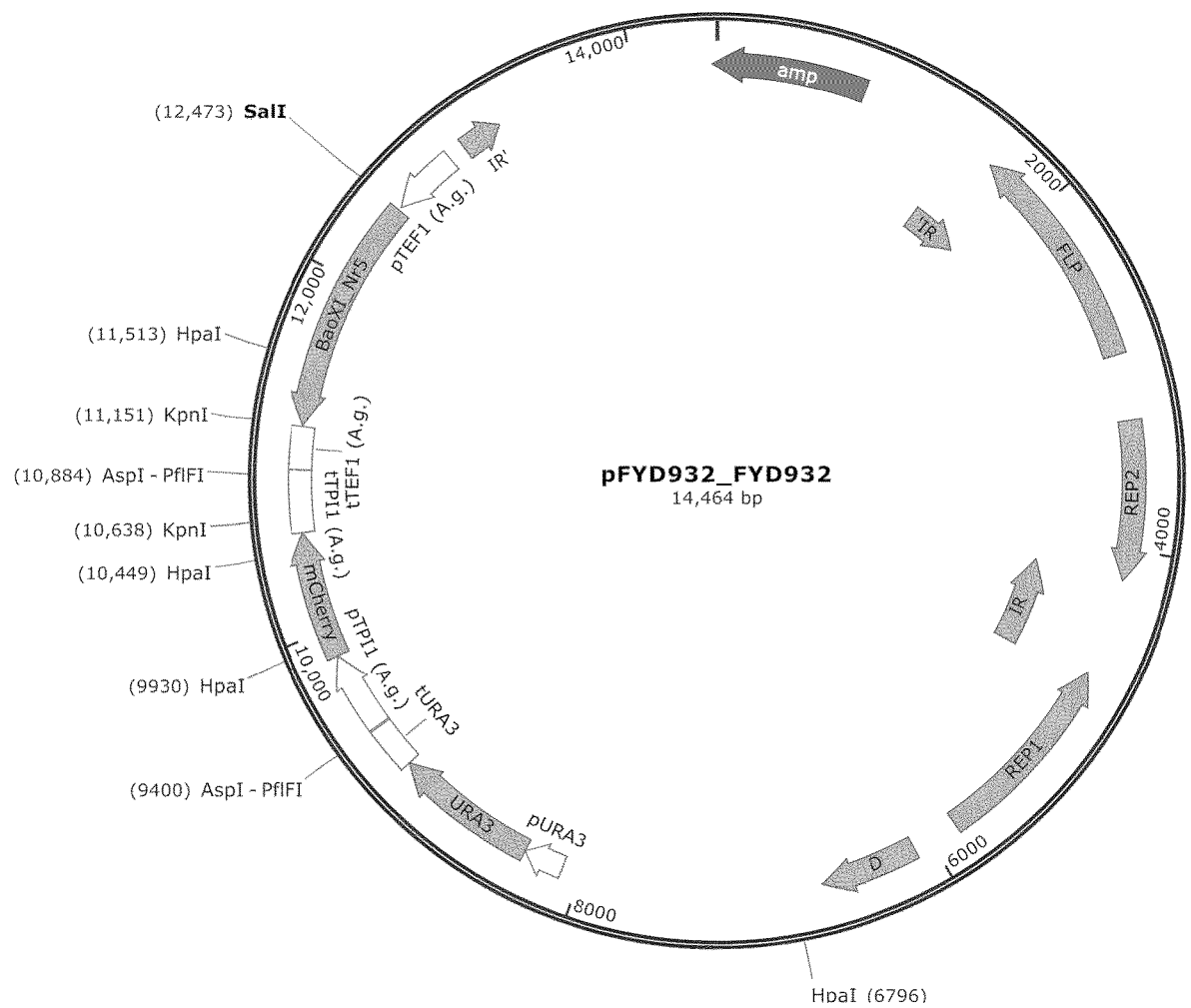
FIG. 12 shows a plasmid map of pFYD932.

The strain FYD932 expressing a *Bos taurus* xylose isomerase (AZM80432 encoding the xylose isomerase of SEQ ID NO: 168) from the pFYD932 plasmid (FIG. 12) was constructed by gap-repair of SalI/AflII digested pFYD898 (FIG. 10) with two PCR products in the cir⁰ strain FYD888. The PCR products were generated with primer sets OY1427+OY1426 and OY1424+OY1425 using pFYD486 and pFYD898 as template, respectively. The PCRs were composed of 5 ng plasmid DNA as template, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, an aliquot of each PCR was loaded onto a 1% agarose gel to confirm that a single PCR product was obtained for each reaction. The remainder of each PCR and the SalI/AflII digested pFYD898 was precipitated with 70% EtOH overnight at −20° C. and resuspended in MilliQ $H_2O$ the next day. Approximately 200 ng pFYD898 SalI/AflII was co-transformed with 1 µL of each PCR product into frozen FYD888 competent cells according to the process described by Gietz & Schiestl (2008) (b) except that 2×YPD media was used instead of 2×YPAD media. One hundred µL of undiluted transformation suspension and 100 µL 100× diluted transformation suspension were plated onto two SC-ura agar plates and incubated for 2-3 days at 30° C. Four transformants were re-streaked on SC-ura plates and one transformant was saved as FYD932.

FYD1137

Strain *S. cerevisiae* FYD1137 was generated by transformation of the GAL1 deletion construct from pFYD1090 (See, U.S. Ser. No. 62/430,690, entitled "Improved Processes for Production of Ethanol from Xylose-containing Cellulosic Substrates using Engineered Yeast Strains", the content of which is hereby incorporated by reference) into FYD888. Frozen competent cells of FYD888 (prepared according to Gietz & Schiestl (2007, *Nat. Protocols* Vol. 2. No. 1. (corrected online 20 Nov. 2008)) were transformed with approx. 1 µg NotI-HF/AscI digested pFYD1090. Following transformation, the cells were recovered in 1 mL YPD for 4 hrs at 30° C. with shaking. The cells were plated onto YPD plates containing 300 µg/mL hygromycin B and the plates were incubated at 30° C. for 2-3 days. Four transformants from each transformation were re-streaked on new selective plates and incubated at 30° C. Deletion of GAL1 was verified by streaking the transformants onto YPD agar plates and SG agar plates. As expected, none of the transformants could grow on the SG agar plates. One transformant was saved as FYD1137.

FYD1144

Strain *S. cerevisiae* FYD1144 was obtained from FYD1137 by removal of the hygromycin resistance marker (flanked by loxP sites) present in the GAL1 deletion construct using pFYD80 (FIG. 5). Competent FYD1137 cells were prepared according to the protocol described in Gietz & Schiestl (2008) (c) and transformed with 1 µg of pFYD80. Following transformation, cells were pelleted at 13,000×g for 30 seconds. Cells were resuspended in 1 mL YPD media and incubated at 30° C. in a thermomixer with shaking for 3 hours. Twenty µL and 200 µL aliquots of the cell suspension were plated onto YPD+200 µg/mL Zeocin plates and incubated at 30° C. for 2-3 days. Four transformants were re-streaked onto YPD+200 µg/mL Zeocin plates and incubated at 30° C. for 2-3 days. A small amount of colony material from each transformant was pooled and used to prepare a 10 ml YPD tube culture, which was incubated overnight at 30° C. In the morning, an aliquot of the culture was transferred to fresh media and incubated at 30° C. with shaking. In the afternoon, serial dilutions of the culture were prepared and 100 µl from each dilution was spread onto YPD agar plates and incubated the plates at 30° C. for two days. A YPD plate with an appropriate number of colonies was picked and the colonies were replica-plated onto YPD+ hygromycin B, YPD+Zeocin and YPD agar plates. The plates were incubated overnight at 30° C. Next day, the plates were inspected and colonies sensitive to both hygromycin B (lost the hyromycin B resistance marker) and Zeocin (lost the pFYD80 plasmid) were re-streaked onto YPD agar plates and incubated at 30° C. for two days. Genomic DNA was extracted from the transformants using the MasterPure™ Yeast DNA Purification Kit (cat. no. MPY80010) from Epicentre®. Correct excision of the hygromycin B resistance marker was verified by PCR using primer set OY1496+OY1497. The PCRs consisted of 0.5 µl genomic DNA as template, 1×DreamTaq Green buffer, 200 µM of each dNTP, 500 nM forward primer, 500 nM reverse primer, 0.5 unit of DreamTaq DNA Polymerase (Thermo Scientific) and MilliQ $H_2O$ to a final volume of 20 µl. The reactions were incubated in a Bio-Rad C1000 Touch™ Thermal Cycler (Bio-Rad Laboratories) programmed for 1 cycle at 95° C. for 5 minutes; 35 cycles each at 95° C. for 10 seconds, 55° C. for 30 seconds and 72° C. for 5.5 minutes; and one cycle at 72° C. for 10 minutes. The PCRs were subjected to 1% agarose gel electrophoresis in TBE. All transformants had the desired excision of the hygromycin B resistance marker. One of the transformants was saved as FYD1144.

FYD1159

Strain *S. cerevisiae* FYD1159 carrying a 2-micron plasmid with a URA3 selection marker was constructed by gap-repair of HpaI/NotI-HF digested pDB4164 (FIG. 9) and two PCR products in FYD1144. The two PCR products used for gap-repair of HpaI/NotI-HF digested pDB4164 were amplified from YGT44 and pDB4164, respectively, using primer sets OY1402+OY1414 and OY1291+OY1415, respectively. The PCRs were composed of 50 ng genomic DNA or 5 ng plasmid DNA as template, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, an aliquot of each PCR was loaded onto a 1% agarose gel to confirm that a single PCR product was obtained for each PCR. The remainder of each PCR and the HpaI/NotI-HF digested pDB4164 was precipitated with 70% EtOH overnight at −20° C. and resuspended in MilliQ $H_2O$ the next day. For the plasmid gap-repair, 50 fmol of HpaI/NotI-HF digested pDB4164 was co-transformed with a 10× molar excess of each PCR product into frozen competent FYD1144 cells using the approach described by Gietz & Schiestl (2008) (b) except that 2×YPD media was used instead of 2×YPAD media. The transformation reaction was diluted 10× and 100× and 100 µL was plated onto SC-ura plates and incubated at 30° C. for 2-3 days. Four transformants were streaked for single colonies onto new SC-ura plates. One of the transformants was saved as FYD1159.

FYD1181

Strain *S. cerevisiae* FYD1181 carrying a 2-micron plasmid expressing a *Bos taurus* xylose isomerase (AZM80432 encoding the xylose isomerase of SEQ ID NO: 168) driven by a truncated TEF1 promoter was constructed by gap-repair of SalI/AflII digested pFYD965 (FIG. 13) with two PCR products in the cir⁰ strain FYD1144. The PCR products were generated with primer sets OY1429+OY1426 and OY1424+OY1425 using pFYD486 and pFYD965 as template, respectively. The PCRs were composed of 5 ng plasmid DNA as template, 1×HF buffer, 200 µM of each dNTP, 500 nM forward primer, 500 nM reverse primer and 1 unit of Phusion® Hot Start Flex DNA Polymerase. The reactions were incubated in a Bio-Rad C1000 Touch™ Thermal Cycler (Bio-Rad Laboratories) programmed for 1 cycle at 98° C. for 3 minutes; 35 cycles each at 98° C. for 10 seconds, 55° C. for 30 seconds and 72° C. for 1 minute; and one cycle at 72° C. for 5 minutes. Following thermocycling, an aliquot of each PCR was loaded onto a 1% agarose gel to confirm that a single PCR product was obtained for each reaction. The remainder of each PCR and the SalI/AflII digested pFYD965 was precipitated with 70% EtOH overnight at −20° C. and resuspended in MilliQ $H_2O$ the next day. Approximately 200 ng pFYD965 SalI/AflII was co-transformed with 1 µL of each PCR product into frozen FYD1144 competent cells according to the process described by Gietz & Schiestl (2008) (b) except that 2×YPD media was used instead of 2×YPAD media. One hundred µL of undiluted transformation suspension and 100 µL 100× diluted transformation suspension were plated onto two SC-ura agar plates and incubated for 2-3 days at 30° C. Four transformants were re-streaked on SC-ura plates and one transformant was saved as FYD1181.

Xylose Isomerase-Encoding Strains Constructed by GAP-Repair with Partial 2µ Plasmid A PCR was conducted using primers OY198 and OY199 for each GeneArt xylose isomerase-encoding polynucleotide string supra to generate a band of approx. 1500 bp. A small 2 µl aliquot on subjected to gel electrophoresis to confirm size, and the remaining PCR product was column purified. This purified product is cleaved by BspQI (50° C.), and heat inactivated (80° C. for 20 min.).

Prior to GAP repair the plasmid pFYD1049 (FIG. 16) was linearized with Acc651. To prevent self-ligation due to sticky ends digested vector was treated with 1 unit T4 DNA Polymerase (NEB) per microgram DNA and incubate 15 minutes at 12° C. The reaction was stopped by adding EDTA to a final concentration of 10 mM and heating to 75° C. for 20 minutes.

For each GAP repair reaction 200 ng of linearized vector was added to competent yeast cells (prepared according to the protocol described in Gietz & Schiesti (2008)) and about 15-50 ng of additional PCR products. 50 µL was plated on SD plates selecting for uracil prototrophs.

Xylose Isomerase-Encoding Strains Constructed by GAP-Repair with Full 2μ Plasmid Containing mCherry GAP-repair was performed using plasmid pFYD965 (FIG. 13) linearized with SalI/AflII to yield a 14089 bp fragment and 299 bp PCR fragment from pFYD496 with primers OY1429/OY2172 as well as PCR product of the GeneArt xylose isomerase-encoding polynucleotide string encoding the xylose isomerase of SEQ ID NO: 22. Four colonies were selected (FYD1144-1, FYD1144-2, FYD1144-3, FYD1144-4).

Example 3: Xylose Growth Experiments

Anaerobic Growth

Strains were cultivated overnight in liquid SD and incubated with 200 rpm shaking at 30° C. Samples (0.5 mL) were harvested in Eppendorf tubes, washed and re-suspend two times in 0.5 mL SX2-media. $OD_{600}$ measurements were taken, the culture was diluted to OD=1 and a series produced of factor 10 serial dilutions in a microtiter plate. 2 μL samples were spotted of each dilution in succession to produce a dilution series on xylose-containing SX2 plates. All plates were placed in sealed jars with oxygen depleting Oxoid satchets AneroGen.

Figure 2:
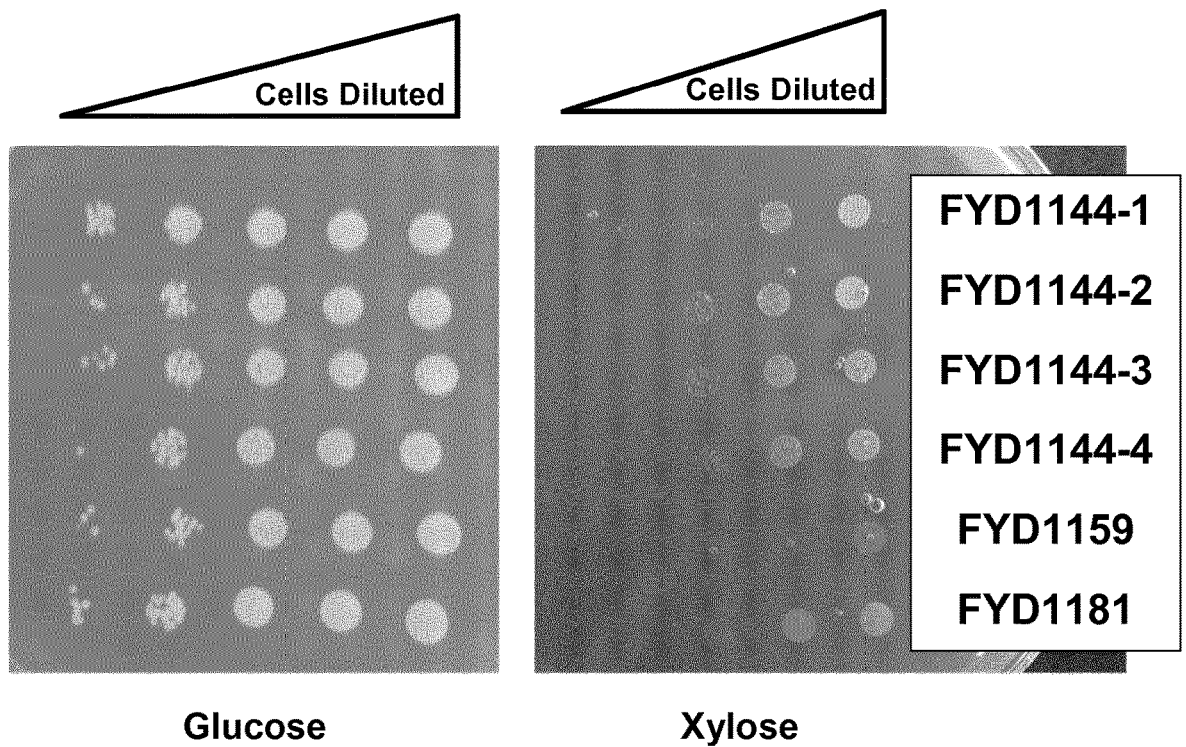
FIG. 2 shows anaerobic cell growth experiments after three weeks on glucose-containing SD plates (left) and xylose-containing SX2 plates (right) at 30° C., as described in Example 3.

As shown in FIG. 1, of the several xylose isomerase-encoding strains constructed by GAP-repair with partial 2μ plasmid (supra), strain 5 (encoding the xylose isomerase of SEQ ID NO: 22) and strain FYD932 (encoding the xylose isomerase of SEQ ID NO: 168) show exceptional growth on xylose compared to the remaining strains. As shown in FIG. 2, the corresponding strains constructed by GAP-repair with full 2ρ plasmid encoding the xylose isomerase of SEQ ID NO: 22 (FYD1144-1 through FYD1144-4) likewise showed exceptional growth on both glucose and xylose relative to the negative control strain (FYD1159, which showed strong growth only on glucose).

Aerobic Growth

Strains were cultivated overnight in liquid SD and incubated with 200 rpm shaking at 30° C. Samples (0.5 mL) were harvested in Eppendorf tubes, washed and re-suspend two times in 0.5 mL SX2-media. $OD_{600}$ measurements were taken, the culture was diluted to OD=1 and a series produced of factor 10 serial dilutions in a microtiter plate. 2 μL samples were spotted of each dilution in succession to produce a dilution series on xylose-containing SX2 plates. All plates were incubated in air permeable boxes.

Figure 3:
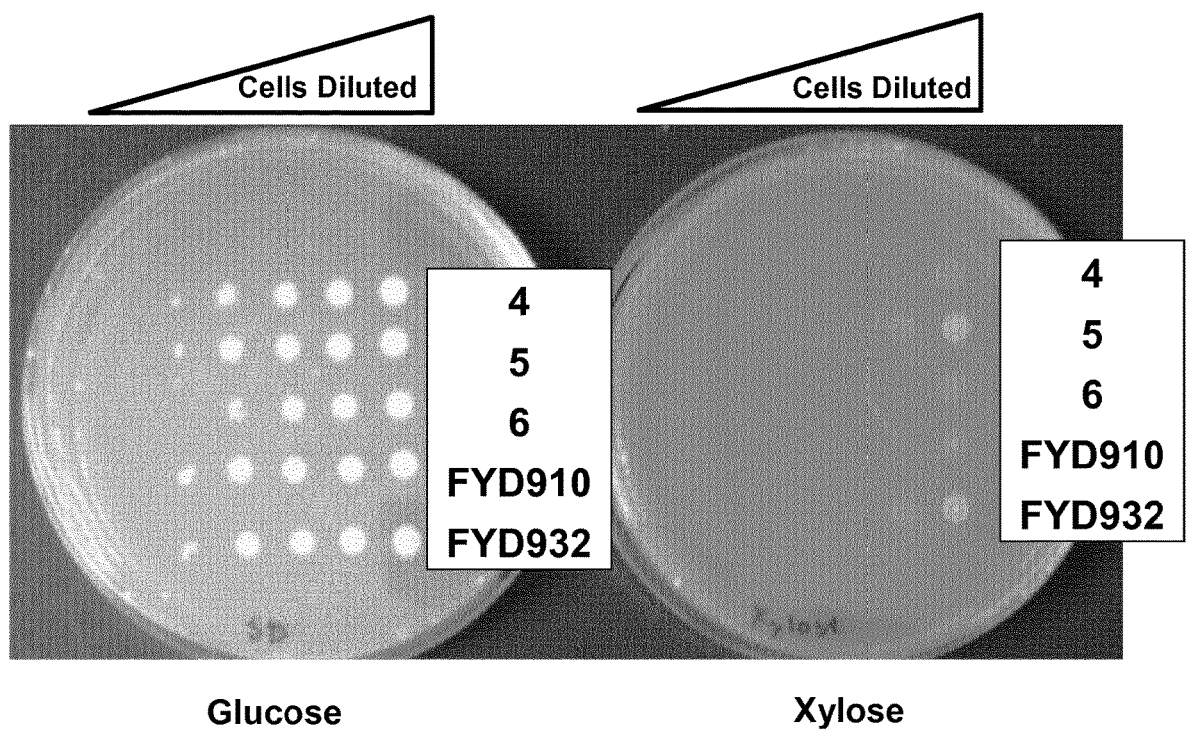
FIG. 3 shows aerobic cell growth experiments after 3 days on glucose-containing SD plates (left) and xylose-containing SX2 plates (right), as described in Example 3. Rows 4-6 correspond to xylose isomerase-encoding strains constructed by GAP-repair with partial 2µ plasmid (expressing the XIs of SEQ ID NOs: 14, 22 and 8, respectively), as described in Example 2.

As shown in FIG. 3, of the several xylose isomerase-encoding strains constructed by GAP-repair with partial 2μ plasmid (supra), strain 5 (encoding the xylose isomerase of SEQ ID NO: 22) and strain FYD932 (encoding the xylose isomerase of SEQ ID NO: 168) show exceptional growth on both glucose and xylose plates, whereas the remaining strains were capable of strong growth only on glucose.

Figure 4:
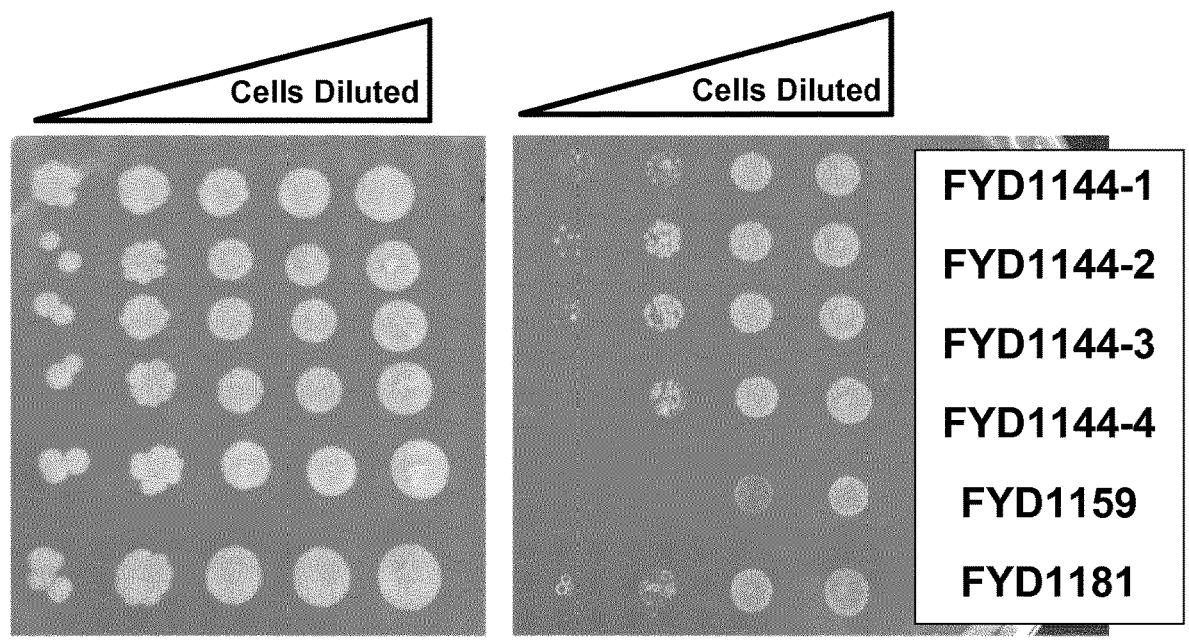
FIG. 4 shows aerobic cell growth experiments after 17 days on glucose-containing SD plates (left) and xylose-containing SX2 plates (right) at 30° C., as described in Example 3.

As shown in FIG. 4, of the xylose isomerase-encoding strains constructed by GAP-repair with partial 2μ plasmid (supra), strain 5 (encoding the xylose isomerase of SEQ ID NO: 22) and strain FYD932 (encoding the xylose isomerase of SEQ ID NO: 168) show superior growth on xylose compared to the remaining strains. As shown in FIG. 4, the corresponding strains constructed by GAP-repair with full 2μ plasmid encoding the xylose isomerase of SEQ ID NO: 22 (1144-1 through 1144-4) likewise showed exceptional growth on both glucose and xylose relative to the negative control strain (FYD1159, which showed strong growth only on glucose).

Although the foregoing has been described in some detail by way of illustration and example for the purposes of clarity of understanding, it is apparent to those skilled in the art that any equivalent aspect or modification may be practiced. Therefore, the description and examples should not be construed as limiting the scope of the invention.

The invention claimed is:

1. A recombinant yeast cell comprising a heterologous polynucleotide encoding a polypeptide having at least 95% sequence identity to SEQ ID NO: 22; and wherein the polypeptide has xylose isomerase activity.

2. The recombinant cell of claim 1, wherein the heterologous polynucleotide encodes a polypeptide that differs by no more than ten amino acids from SEQ ID NO: 22.

3. The recombinant cell of claim 1, wherein the heterologous polynucleotide encodes a polypeptide having an amino acid sequence comprising or consisting of the amino acid sequence of SEQ ID NO: 22.

4. The recombinant cell of claim 1, wherein the heterologous polynucleotide comprises a coding sequence having at least 95% sequence identity to SEQ ID NO: 21.

5. The recombinant cell of claim 4, wherein the heterologous polynucleotide has a coding sequence that consists of SEQ ID NO: 21.

6. The recombinant cell of claim 1, further comprising a heterologous polynucleotide encoding one or more polypeptides selected from:

a xylulokinase (XK);

a hexose transporter (e.g., HXT1, HXT2, HXT3, HXT4, HXT5, HXT6, HXT7, or GAL2);

a ribulose 5 phosphate 3-epimerase (RPE1);

a ribulose 5 phosphate isomerase (RKI1);

a transketolase (TKL1); and a transaldolase (TAL1).

7. The recombinant cell of claim 1, further comprise a disruption to an endogenous gene encoding a glycerol 3-phosphate dehydrogenase (GPD) and/or a glycerol 3-phosphatase (GPP).

8. The recombinant cell of claim 1, which is a *Saccharomyces, Rhodotorula, Schizosaccharomyces, Kluyveromyces, Pichia, Hansenula, Rhodosporidium, Candida, Yarrowia, Lipomyces, Cryptococcus*, or Dekkera sp. cell.

9. The recombinant cell of claim 1, which is a *Saccharomyces cerevisiae* cell.

10. The recombinant cell of claim 1, wherein the cell is capable of growing on xylose.

11. The recombinant cell of claim 1, wherein the recombinant cell has a higher growth rate on xylose compared to the same cell without the heterologous polynucleotide encoding a xylose isomerase.

12. The recombinant cell of claim 1, wherein the strain has a higher xylose consumption compared to the same cell without the heterologous polynucleotide encoding a xylose isomerase.

13. The recombinant cell of claim 1, wherein the strain has a higher ethanol production compared to the same cell without the heterologous polynucleotide encoding a xylose isomerase.

14. A process for producing ethanol, comprising cultivating the recombinant cell of claim 1 in a fermentable medium under suitable conditions to produce ethanol.

15. The process of claim 14, wherein cultivation is conducted under low oxygen conditions.

16. The process of claim 14, wherein an increased amount of xylose is consumed when compared to the process using an identical cell without the heterologous polynucleotide encoding a xylose under the same conditions.

17. The process of claim 14, wherein the process results in higher ethanol yield when compared to the process using an identical cell without the heterologous polynucleotide encoding a xylose isomerase under the same conditions.

18. The process of claim 14, comprising recovering the fermentation product from the fermentation.

19. The process of claim 14, comprising saccharifying a cellulosic and/or starch-containing material with an enzyme composition to produce the fermentable medium.

20. The recombinant cell of claim 1, wherein the heterologous polynucleotide encodes a polypeptide having at least 97% sequence identity to SEQ ID NO: 22.

21. The recombinant cell of claim 1, wherein the heterologous polynucleotide encodes a polypeptide having at least 98% sequence identity to SEQ ID NO: 22.

22. The recombinant cell of claim 1, wherein the heterologous polynucleotide encodes a polypeptide having at least 99% sequence identity to SEQ ID NO: 22.

23. The recombinant cell of claim 1, wherein the heterologous polynucleotide encodes a polypeptide that differs by no more than five amino acids from SEQ ID NO: 22.

24. The recombinant cell of claim 1, wherein the heterologous polynucleotide encodes a polypeptide that differs by no more than three amino acids from SEQ ID NO: 22.

* * * * *